(12) United States Patent
Worley et al.

(10) Patent No.: US 10,914,749 B2
(45) Date of Patent: *Feb. 9, 2021

(54) BIOMARKERS OF COGNITIVE DYSFUNCTION

(71) Applicant: THE JOHNS HOPKINS UNIVERSITY, Baltimore, MD (US)

(72) Inventors: Paul F. Worley, Baltimore, MD (US); DeSheng Xu, Lutherville-Timonium, MD (US); Meifang Xiao, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,008

(22) Filed: Feb. 1, 2019

(65) Prior Publication Data
US 2019/0353668 A1    Nov. 21, 2019

Related U.S. Application Data

(63) Continuation of application No. 15/511,860, filed as application No. PCT/US2015/050884 on Sep. 18, 2015, now Pat. No. 10,222,386.
(Continued)

(51) Int. Cl.
*A61K 39/395* (2006.01)
*A61K 51/10* (2006.01)
(Continued)

(52) U.S. Cl.
CPC ......... *G01N 33/6896* (2013.01); *C07K 16/18* (2013.01); *G01N 33/53* (2013.01);
(Continued)

(58) Field of Classification Search
None
See application file for complete search history.

(56) References Cited

U.S. PATENT DOCUMENTS

4,816,567 A    3/1989  Cabilly et al.
4,981,785 A    1/1991  Nayak
(Continued)

FOREIGN PATENT DOCUMENTS

WO    2000056934 A1    9/2000
WO    2001031580 A2    5/2001
(Continued)

OTHER PUBLICATIONS

Ruczinski, et al., Logic Regression. J Comp Graph Stat, 12, 475-511, 2012.
(Continued)

*Primary Examiner* — Aurora M Fontainhas
(74) *Attorney, Agent, or Firm* — DLA Piper LLP (US)

(57) ABSTRACT

The present invention relates to the field of cognitive function. More specifically, the present invention provides compositions and methods useful for assessing cognitive dysfunction/function in Alzheimer's disease and other diseases of cognition. In one embodiment, the method comprises the steps of (a) reducing heterocomplexes comprising NPTX1 and NPTX2 present in a biological sample obtained from the patient into NPTX1 and NPTX2 monomers; (b) covalently modifying the thiol groups of the NPTX1 and NPTX2 monomers to prevent re-formation of NPTX1/NPTX2 heterocomplexes; (c) detecting NPTX2 in the sample; and (d) assessing cognitive function in the patient by comparing NPTX2 detected in the sample to a control.

29 Claims, 51 Drawing Sheets

Specification includes a Sequence Listing.

Related U.S. Application Data

(60) Provisional application No. 62/219,867, filed on Sep. 17, 2015, provisional application No. 62/052,612, filed on Sep. 19, 2014.

(51) Int. Cl.
| | |
|---|---|
| C07K 16/18 | (2006.01) |
| C07K 16/38 | (2006.01) |
| G01N 33/58 | (2006.01) |
| C12N 5/079 | (2010.01) |
| G01N 33/68 | (2006.01) |
| G01N 33/566 | (2006.01) |
| G01N 33/53 | (2006.01) |
| G06F 19/00 | (2018.01) |

(52) U.S. Cl.
CPC ....... *G01N 33/566* (2013.01); *G01N 33/6851* (2013.01); *G01N 2800/2821* (2013.01); *G01N 2800/2835* (2013.01); *G06F 19/00* (2013.01)

(56) References Cited

U.S. PATENT DOCUMENTS

| | | | |
|---|---|---|---|
| 5,225,539 | A | 6/1993 | Winter |
| 5,242,828 | A | 9/1993 | Bergstrom et al. |
| 5,270,163 | A | 12/1993 | Gold et al. |
| 5,358,691 | A | 10/1994 | Clark et al. |
| 5,475,096 | A | 12/1995 | Gold et al. |
| 5,545,806 | A | 8/1996 | Lonberg et al. |
| 5,545,807 | A | 8/1996 | Surani et al. |
| 5,567,588 | A | 10/1996 | Gold et al. |
| 5,569,825 | A | 10/1996 | Lonberg et al. |
| 5,595,877 | A | 1/1997 | Gold et al. |
| 5,625,126 | A | 4/1997 | Lonberg et al. |
| 5,633,425 | A | 5/1997 | Lonberg et al. |
| 5,637,459 | A | 6/1997 | Burke et al. |
| 5,641,870 | A | 6/1997 | Rinderknecht et al. |
| 5,660,985 | A | 8/1997 | Pieken et al. |
| 5,661,016 | A | 8/1997 | Lonberg et al. |
| 5,670,637 | A | 9/1997 | Gold et al. |
| 5,683,867 | A | 11/1997 | Biesecker et al. |
| 5,696,249 | A | 12/1997 | Gold et al. |
| 5,707,796 | A | 1/1998 | Gold et al. |
| 5,719,060 | A | 2/1998 | Hutchens et al. |
| 5,750,373 | A | 5/1998 | Garrard et al. |
| 5,866,434 | A | 2/1999 | Massey et al. |
| 5,885,530 | A | 3/1999 | Babson et al. |
| 6,011,020 | A | 1/2000 | Gold et al. |
| 6,090,545 | A | 7/2000 | Wohlstadter et al. |
| 6,140,045 | A | 10/2000 | Wohlstadter et al. |
| 6,159,750 | A | 12/2000 | Edmonds |
| 6,207,369 | B1 | 3/2001 | Wohlstadter et al. |
| 6,225,047 | B1 | 5/2001 | Hutchens et al. |
| 6,319,670 | B1 | 11/2001 | Sigal et al. |
| 6,329,209 | B1 | 12/2001 | Wagner et al. |
| 6,362,011 | B1 | 3/2002 | Massey et al. |
| 6,413,783 | B1 | 7/2002 | Wohlstadter et al. |
| 6,537,749 | B2 | 3/2003 | Kuimelis et al. |
| 6,673,533 | B1 | 1/2004 | Wohlstadter et al. |
| 6,919,173 | B2 | 7/2005 | Tsionsky et al. |
| 6,977,722 | B2 | 12/2005 | Wohlstadter et al. |
| 7,036,946 | B1 | 5/2006 | Mosier |
| 7,052,861 | B2 | 5/2006 | Massey et al. |
| 7,288,410 | B2 | 10/2007 | Tsionsky et al. |
| 7,491,540 | B2 | 2/2009 | Tsionsky et al. |
| 7,497,997 | B2 | 3/2009 | Glezer et al. |
| 2001/0021534 | A1 | 9/2001 | Wohlstadter et al. |
| 2002/0086335 | A1 | 6/2002 | Massey et al. |
| 2002/0137234 | A1 | 9/2002 | Wohlstadter et al. |
| 2002/0138208 | A1 | 9/2002 | Paulse et al. |
| 2002/0193950 | A1 | 12/2002 | Edward et al. |
| 2003/0003460 | A1 | 1/2003 | Sigal et al. |
| 2003/0004402 | A1 | 3/2003 | Hitt et al. |
| 2003/0055615 | A1 | 3/2003 | Zhang et al. |
| 2003/0113713 | A1 | 6/2003 | Glezer et al. |
| 2003/0124572 | A1 | 7/2003 | Umek et al. |
| 2004/0022677 | A1 | 2/2004 | Wohlstater et al. |
| 2005/0052646 | A1 | 3/2005 | Wohlstadter et al. |
| 2005/0142033 | A1 | 6/2005 | Glezer et al. |
| 2006/0019319 | A1 | 1/2006 | Billadeau et al. |
| 2006/0172340 | A1 | 8/2006 | Wohlstadter et al. |
| 2009/0065357 | A1 | 3/2009 | Glezer et al. |
| 2009/0170121 | A1 | 7/2009 | Tsionsky et al. |
| 2010/0093557 | A1 | 4/2010 | Kumble |
| 2010/0190656 | A1 | 7/2010 | Li et al. |
| 2011/0282820 | A1 | 7/2011 | Seeburger, et al. |
| 2013/0337479 | A1 | 12/2013 | Uchida et al. |

FOREIGN PATENT DOCUMENTS

| | | | |
|---|---|---|---|
| WO | 2001036626 | A2 | 5/2001 |
| WO | 2003048768 | A2 | 12/2003 |
| WO | 2008-020435 | A2 | 2/2008 |
| WO | 2016044697 | A1 | 3/2016 |

OTHER PUBLICATIONS

Friedman, et al., Regularized Discriminant Analysis. J Am Stat Assoc, 84, 165-175, 1989.
Breiman, Random Forests. Machine Learning, 45, 5-31, 2001.
Jain, et al., Statistical pattern recognition: a review. IEEE Transactions on Pattern Analysis and Machine Intelligence, 22, 4-27, 2000.
Al-Lazikani, et al., Standard conformations for the canonical structures of immunoglobulins. J Mol Biol, 273, 927-948, 1997.
Kohler, et al., Continuous cultures of fused cells secreting antibody of predefined specificity. Nature, 256, 495-497, 1975.
McCafferty, et al., Phage antibodies: filamentous phage displaying antibody variable domains. Nature, 348, 552-554, 1990.
Clarkson, et al., Making antibody fragments using phage display libraries. Nature, 352, 624-628, 1991.
Marks, et al., By-passing immunization. Human antibodies from V-gene libraries displayed on phage. J Mol Biol, 222, 581-597, 1991.
Jones, et al., Replacing the complementarity-determining regions in a human antibody with those from a mouse. Nature, 321, 522-525, 1986.
Riechmann, et al., Reshaping human antibodies for therapy. Nature, 332, 323-327, 1988.
Verhoeyen, et al., Reshaping human antibodies: grafting an antilysozyme activity. Science, 239, 1534-1536, 1988.
Boerner, et al., Production of antigen-specific human monoclonal antibodies from in vitro-primed human splenocytes. J Immunol, 147, 86-95, 1991.
Vaughan, et al. Human Antibodies with Sub-nanomolar Affinities Isolated from a Large Non-immunized Phage Display Library Nature Biotech, 14, 309-314, 1996.
Sheets, et al., Efficient construction of a large nonimmune phage antibody library: The production of high-affinity human single-chain antibodies to protein antigens. PNAS, 95, 6157-6162, 1998.
Hoogenboom, et al., By-passing immunisation. Human antibodies from synthetic repertoires of germline VH gene segments rearranged in vitro. J Mol Biol, 227, 381-388, 1992.
Morimoto, et al., Single-step purification of F(ab')2 fragments of mouse monoclonal antibodies (immunoglobulins G1) by hydrophobic interaction high performance liquid chromatography using TSKgel Phenyl-5PW. J Biochem Biophys Methods, 24, 107-117, 1992.
Brennan, et al., Preparation of bispecific antibodies by chemical recombination of monoclonal immunoglobulin G1 fragments. Science, 229, 81-83, 1985.
Borchelt, et al., Accelerated amyloid deposition in the brains of transgenic mice coexpressing mutant presenilin 1 and amyloid precursor proteins. Neuron, 19, 939-945, 1997.
Xu, et al., Narp and NP1 form heterocomplexes that function in developmental and activity-dependent synaptic plasticity. Neuron, 39, 513-528, 2003.
Cho, et al., mGluR1/5-dependent long-term depression requires the regulated ectodomain cleavage of neuronal pentraxin NPR by TACE. Neuron, 57, 858-871, 2008.

(56) References Cited

OTHER PUBLICATIONS

Cai, et al., BACE1 is the major beta-secretase for generation of Abeta peptides by neurons. Nat Neurosci, 4, 233-234, 2001.
Wu, et al., Arc/Arg3.1 regulates an endosomal pathway essential for activity-dependent β-amyloid generation. Cell, 147, 615-628, 2011.
Chang, et al., Narp regulates homeostatic scaling of excitatory synapses on parvalbumin-expressing interneurons. Nat Neurosci, 13, 1090-1097, 2010.
Tsui, et al., Narp, a novel member of the pentraxin family, promotes neurite outgrowth and is dynamically regulated by neuronal activity. J Neurosci 16, 2463 (Apr. 15, 1996).
O'Brien, et al., Synaptically targeted narp plays an essential role in the aggregation of AMPA receptors at excitatory synapses in cultured spinal neurons. J Neurosci 22, 4487 (Jun. 1, 2002).
O'Brien, et al., Synaptic clustering of AMPA receptors by the extracellular immediate-early gene product Narp. Neuron 23, 309, 1999.
Hu, et al., Homeostatic scaling requires group I mGluR activation mediated by Homer1a. Neuron, 68, 1128-1142, 2010.
Kandel, et al., The molecular and systems biology of memory. Cell, 157, 163-186, 2014.
Marton, et al., Homer 1a and mGluR5 phosphorylation in reward-sensitive metaplasticity: A hypothesis of neuronal selection and bidirectional synaptic plasticity. Brain Research, 1628, 17-28, 2015.
Shepherd, et al., Arc/Arg3.1 mediates homeostatic synaptic scaling of AMPA receptors. Neuron, 52, 475-484, 2006.
Worley, et al., Solving the Mystery of Memory. Cerebrum, 2014, 2.
Vassar, et al., The beta-secretase enzyme BACE1 as a therapeutic target for Alzheimer's disease. Alzheimers Res Ther 3, 20, doi:10.1186/alzrt82 (2011).
Kamenetz, et al., APP processing and synaptic function. Neuron 37, 925-937 (2003).
Cirrito, et al., Synaptic activity regulates interstitial fluid amyloid-beta levels in vivo. Neuron 48, 913-922 (2005).
Bero, et al., Neuronal activity regulates the regional vulnerability to amyloid-beta deposition. Nature neuroscience 14, 750-756, doi:10.1038/nn.2801 (2011).
Sia, et al., Interaction of the N-terminal domain of the AMPA receptor GluR4 subunit with the neuronal pentraxin NP1 mediates GluR4 synaptic recruitment. Neuron 55, 87-102 (2007).
Selkoe, et al., Presenilin: running with scissors in the membrane. Cell 131, 215-221 (2007).
Jonsson, et al., A mutation in APP protects against Alzheimer's disease and age-related cognitive decline. Nature 488, 96-99, doi:10.1038/nature11283 (2012).
Cirrito, et al., Endocytosis is required for synaptic activity-dependent release of amyloid-beta in vivo. Neuron 58, 42-51, doi:10.1016/j.neuron.2008.02.003 (2008).
Sperling, et al., Amyloid deposition is associated with impaired default network function in older persons without dementia. Neuron 63, 178-188, doi:10.1016/j.neuron.2009.07.003 (2009).
Buckner, et al., Cortical hubs revealed by intrinsic functional connectivity: mapping, assessment of stability, and relation to Alzheimer's disease. The Journal of neuroscience : the official journal of the Society for Neuroscience 29, 1860-1873, doi:10.1523/JNEUROSCI.5062-08.2009 (2009).
Emsley, et al., Structure of pentameric human serum amyloid P component. Nature 367, 338-345 (1994).
Stetefeld, et al., Modulation of agrin function by alternative splicing and Ca2+ binding. Structure 12, 503-515, doi:10.1016/j.str.2004.02.001 (2004).

Hohenester, et al., Domain structure and organisation in extracellular matrix proteins. Matrix Biol 21, 115-128 (2002).
Omeis, et al., Mouse and human neuronal pentraxin 1 (NPTX1): conservation, genomic structure, and chromosomal localization. Genomics 36, 543-545 (1996).
Dodds, et al., Neuronal pentraxin receptor, a novel putative integral membrane pentraxin that interacts with neuronal pentraxin 1 and 2 and taipoxin-associated calcium-binding protein 49. The Journal of biological chemistry 272, 21488-21494 (1997).
Vassar, et al., Beta-secretase cleavage of Alzheimer's amyloid precursor protein by the transmembrane aspartic protease BACE. Science (New York, N.Y 286, 735-741 (1999).
Driscoll, et al., Asymptomatic Alzheimer's disease: a prodrome or a state of resilience? Curr Alzheimer Res 8, 330-335 (2011).
Buckner, et al., Molecular, structural, and functional characterization of Alzheimer's disease: evidence for a relationship between default activity, amyloid, and memory. The Journal of neuroscience : the official journal of the Society for Neuroscience 25, 7709-7717, 2005.
Nelson, et al., Alzheimer's-type neuropathology in the precuneus is not increased relative to other areas of neocortex across a range of cognitive impairment. Neuroscience letters 450, 336-339, doi:10.1016/j.eulet.2008.11.006 (2009).
Buzsaki, et al., Temporal structure in spatially organized neuronal ensembles: a role for interneuronal networks. Curr Opin Neurobiol 5, 504-510 (1995).
Klausberger, et al., Neuronal diversity and temporal dynamics: the unity of hippocampal circuit operations. Science (New York, N.Y 321, 53-57, doi:10.1126/science.1149381 (2008).
McBain, et al., Presynaptic plasticity: targeted control of inhibitory networks. Curr Opin Neurobiol 19, 254-262, doi:10.1016/j.conb.2009.05.008 (2009).
Turrigiano, Homeostatic synaptic plasticity: local and global mechanisms for stabilizing neuronal function. Cold Spring Harb Perspect Biol 4, a005736, doi:10.1101/cshperspect.a005736 (2012).
Chowdhury, et al., Arc/Arg3.1 interacts with the endocytic machinery to regulate AMPA receptor trafficking. Neuron 62, 445-459 (2006).
Park, et al., Elongation factor 2 and fragile X mental retardation protein control the dynamic translation of Arc/Arg3.1 essential for mGluR-LTD. Neuron 59, 70-83 (2008).
Yu, et al., Obligatory role for the immediate early gene NARP in critical period plasticity. Neuron 79, 335-346, 2013.
Verret, et al., Inhibitory interneuron deficit links altered network activity and cognitive dysfunction in Alzheimer model. Cell 149, 708-721, doi:10.1016/j.cell.2012.02.046 (2012).
Fagan, et al., Upcoming candidate cerebrospinal fluid biomarkers of Alzheimer's disease. Biomark Med 6, 455-476, 2012.
Spellman, et al., Development and evaluation of a multiplexed mass spectrometry based assay for measuring candidate peptide biomarkers in Alzheimer's Disease. Proteomics Clin Appl, 9, 715-731, 2015.
Osera, et al., Pentraxins and Alzheimer's disease: At the interface between biomarkers and pharmacological targets. Ageing Res Rev, 11, 189-198, 2012.
Yin, et al., Neuronal pentraxin receptor in cerebrospinal fluid as a potential biomarker for neurodegenerative diseases. Brain Research, 1265, 158-170, 2009.
Moran, L. B. et al., "Neuronal pentraxin II is highly upregulated in Parkinson's disease and a novel component of Lewy bodies", Acta Neuropathologica, Apr. 2008, vol. 115, No. 4, pp. 471-478.
Strauss, J. et al., "Association study of early-immediate genes in childhood-onset mood disorders and suicide attempt", Psychiatry Research, May 15, 2012, vol. 197, Nos. 1-2, pp. 49-54.

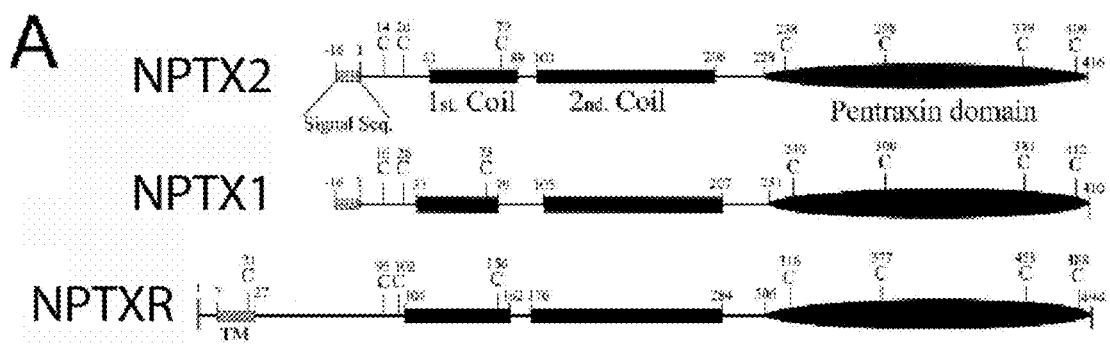
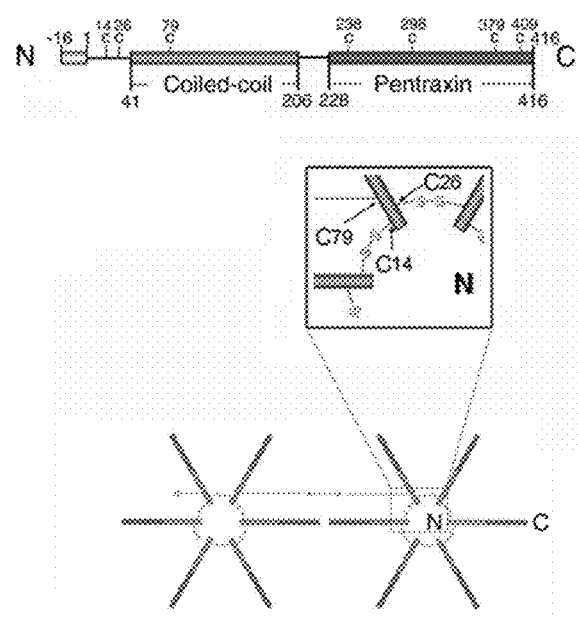
FIG. 12A
FIG. 12B

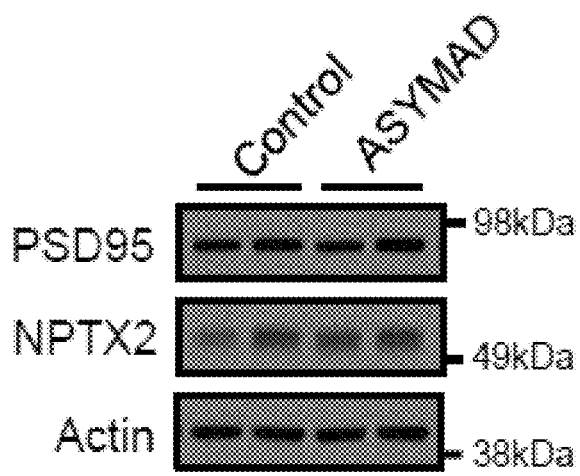
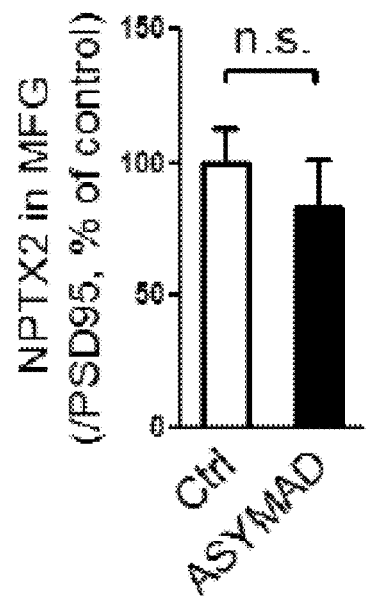
FIG. 17E  FIG. 17F
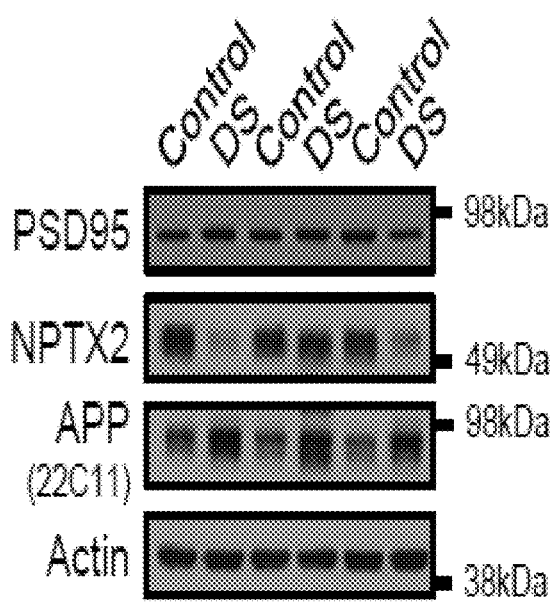
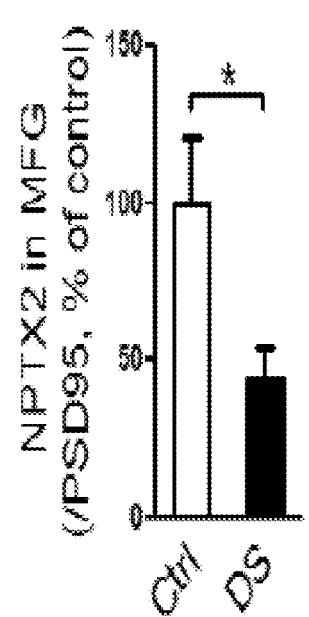
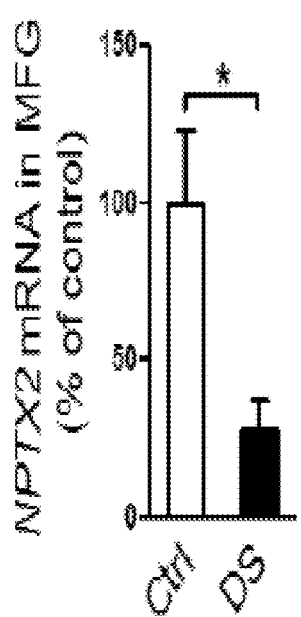
FIG. 17G  FIG. 17H  FIG. 17I

Fear Conditioning

Contextual Memory

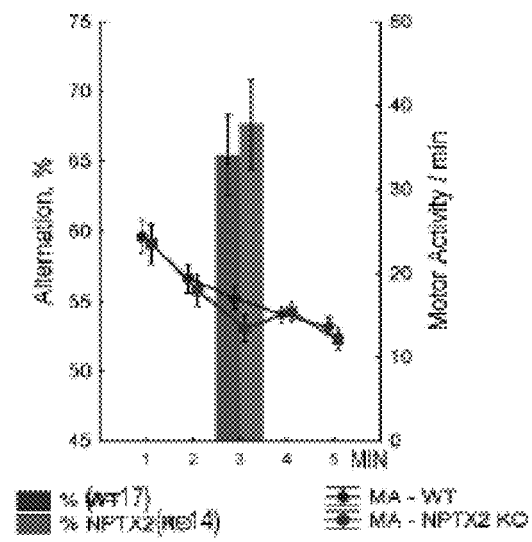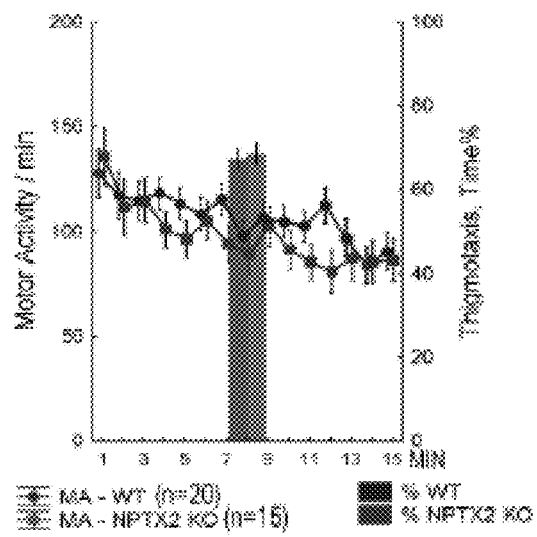
FIG. 26A
FIG. 26B
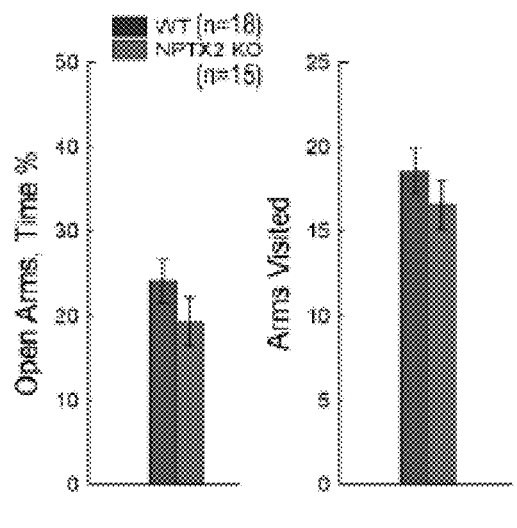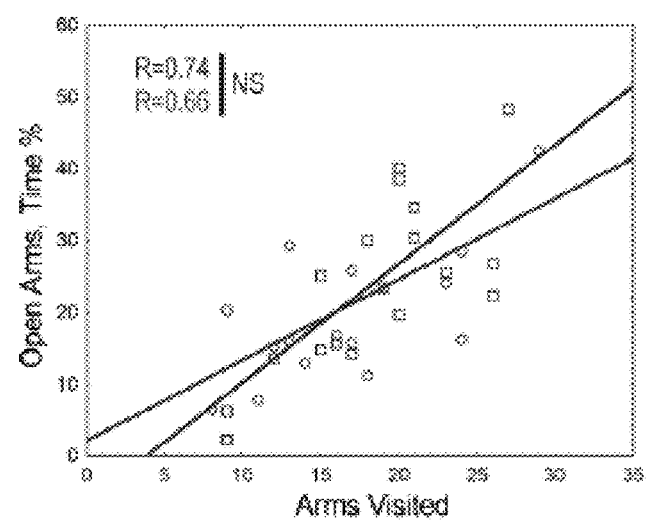
FIG. 26C

SEQUENCE LISTING

<160> NUMBER OF SEQ ID NOS: 37

<210> SEQ ID NO 1
<211> LENGTH: 33
<212> TYPE: DNA
<213> ORGANISM: Artificial Sequence
<220> FEATURE:
<223> OTHER INFORMATION: synthetic HA sequence

<400> SEQUENCE: 1
gagccctacc catacgatgt tccagattac gct                33

<210> SEQ ID NO 2
<211> LENGTH: 33
<212> TYPE: DNA
<213> ORGANISM: Artificial Sequence
<220> FEATURE:
<223> OTHER INFORMATION: synthetic HA sequence

<400> SEQUENCE: 2
ccggccagcg taatctggaa catcgtatgg gta                33

<210> SEQ ID NO 3
<211> LENGTH: 24
<212> TYPE: DNA
<213> ORGANISM: Artificial Sequence
<220> FEATURE:
<223> OTHER INFORMATION: Primer for generation of GST-NPTX1 pentraxin
      domain fusion construct

<400> SEQUENCE: 3
cgacccggag acaagtttca gctg                24

<210> SEQ ID NO 4
<211> LENGTH: 29
<212> TYPE: DNA
<213> ORGANISM: Artificial Sequence
<220> FEATURE:
<223> OTHER INFORMATION: Primer for generation of GST-NPTX1 pentraxin
      domain fusion construct

<400> SEQUENCE: 4
gcagaattct taaatttctc aactccttc                29

<210> SEQ ID NO 5
<211> LENGTH: 20
<212> TYPE: DNA
<213> ORGANISM: Artificial Sequence
<220> FEATURE:
<223> OTHER INFORMATION: NPTX2 forward primer

<400> SEQUENCE: 5
cgcgcagcgc gaggccatcc                20

<210> SEQ ID NO 6
<211> LENGTH: 20
<212> TYPE: DNA
<213> ORGANISM: Artificial Sequence
<220> FEATURE:
<223> OTHER INFORMATION: NPTX2 reverse primer

<400> SEQUENCE: 6
tgcctctcca gctcccccag                20

<210> SEQ ID NO 7
<211> LENGTH: 18

-continued

```
<212> TYPE: DNA
<213> ORGANISM: Artificial Sequence
<220> FEATURE:
<223> OTHER INFORMATION: NPTX2 forward primer

<400> SEQUENCE: 7
catcgagctg ctcatcaa                                                 18

<210> SEQ ID NO 8
<211> LENGTH: 19
<212> TYPE: DNA
<213> ORGANISM: Artificial Sequence
<220> FEATURE:
<223> OTHER INFORMATION: NPTX2 reverse primer

<400> SEQUENCE: 8
ctgctcttgt ccaaggatc                                                19

<210> SEQ ID NO 9
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 9
agaaggctgg ggctcatttg                                               20

<210> SEQ ID NO 10
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 10
aggggccatc cacagtcttc                                               20

<210> SEQ ID NO 11
<211> LENGTH: 431
<212> TYPE: PRT
<213> ORGANISM: Homo sapiens
<220> FEATURE:
<221> NAME/KEY: MISC_FEATURE
<222> LOCATION: (1)..(431)
<223> OTHER INFORMATION: Human NPTX2
<220> FEATURE:
<221> NAME/KEY: SIGNAL
<222> LOCATION: (1)..(16)
<220> FEATURE:
<221> NAME/KEY: MISC_FEATURE
<222> LOCATION: (48)..(59)
<223> OTHER INFORMATION: Epitope used to produce monoclonal antibodies

<400> SEQUENCE: 11

Met Leu Ala Leu Leu Ala Ala Ser Val Ala Leu Ala Val Ala Ala Gly
1               5                   10                  15

Ala Gln Asp Ser Pro Ala Pro Gly Ser Arg Phe Val Cys Thr Ala Leu
                20                  25                  30

Pro Pro Glu Ala Val His Ala Gly Cys Pro Leu Pro Ala Met Pro Met
            35                  40                  45

Gln Gly Gly Ala Gln Ser Pro Glu Glu Glu Leu Arg Ala Ala Val Leu
        50                  55                  60

Gln Leu Arg Glu Thr Val Val Gln Gln Lys Glu Thr Leu Gly Ala Gln
65                  70                  75                  80
```

```
Arg Glu Ala Ile Arg Glu Leu Thr Gly Lys Leu Ala Arg Cys Glu Gly
                85                  90                  95

Leu Ala Gly Gly Lys Ala Arg Gly Ala Gly Thr Gly Lys Asp Thr
            100                 105                 110

Met Gly Asp Leu Pro Arg Asp Pro Gly His Val Val Glu Gln Leu Ser
            115                 120                 125

Arg Ser Leu Gln Thr Leu Lys Asp Arg Leu Glu Ser Leu Glu His Gln
        130                 135                 140

Leu Arg Ala Asn Val Ser Asn Ala Gly Leu Pro Gly Asp Phe Arg Glu
145                 150                 155                 160

Val Leu Gln Gln Arg Leu Gly Glu Leu Glu Arg Gln Leu Leu Arg Lys
                165                 170                 175

Val Ala Glu Leu Glu Asp Glu Lys Ser Leu Leu His Asn Glu Thr Ser
            180                 185                 190

Ala His Arg Gln Lys Thr Glu Ser Thr Leu Asn Ala Leu Leu Gln Arg
        195                 200                 205

Val Thr Glu Leu Glu Arg Gly Asn Ser Ala Phe Lys Ser Pro Asp Ala
    210                 215                 220

Phe Lys Val Ser Leu Pro Leu Arg Thr Asn Tyr Leu Tyr Gly Lys Ile
225                 230                 235                 240

Lys Lys Thr Leu Pro Glu Leu Tyr Ala Phe Thr Ile Cys Leu Trp Leu
                245                 250                 255

Arg Ser Ser Ala Ser Pro Gly Ile Gly Thr Pro Phe Ser Tyr Ala Val
            260                 265                 270

Pro Gly Gln Ala Asn Glu Ile Val Leu Ile Glu Trp Gly Asn Asn Pro
        275                 280                 285

Ile Glu Leu Leu Ile Asn Asp Lys Val Ala Gln Leu Pro Leu Phe Val
    290                 295                 300

Ser Asp Gly Lys Trp His His Ile Cys Val Thr Trp Thr Thr Arg Asp
305                 310                 315                 320

Gly Met Trp Glu Ala Phe Gln Asp Gly Glu Lys Leu Gly Thr Gly Glu
                325                 330                 335

Asn Leu Ala Pro Trp His Pro Ile Lys Pro Gly Gly Val Leu Ile Leu
            340                 345                 350

Gly Gln Glu Gln Asp Thr Val Gly Gly Arg Phe Asp Ala Thr Gln Ala
        355                 360                 365

Phe Val Gly Glu Leu Ser Gln Phe Asn Ile Trp Asp Arg Val Leu Arg
    370                 375                 380

Ala Gln Glu Ile Val Asn Ile Ala Asn Cys Ser Thr Asn Met Pro Gly
385                 390                 395                 400

Asn Ile Ile Pro Trp Val Asp Asn Asn Val Asp Val Phe Gly Gly Ala
                405                 410                 415

Ser Lys Trp Pro Val Glu Thr Cys Glu Glu Arg Leu Leu Asp Leu
            420                 425                 430

<210> SEQ ID NO 12
<211> LENGTH: 432
<212> TYPE: PRT
<213> ORGANISM: Rattus norvegicus
<220> FEATURE:
<221> NAME/KEY: MISC_FEATURE
<222> LOCATION: (1)..(432)
<223> OTHER INFORMATION: Rat NPTX2

<400> SEQUENCE: 12

Met Leu Ala Leu Leu Thr Ala Gly Val Ala Leu Ala Val Ala Ala Gly
```

-continued

```
1               5                   10                  15
Gln Ala Gln Asp Asn Pro Ile Pro Gly Ser Arg Phe Val Cys Thr Ala
                20                  25                  30
Leu Pro Pro Glu Ala Ala Arg Ala Gly Cys Pro Leu Pro Ala Met Pro
                35                  40                  45
Met Gln Gly Gly Ala Leu Ser Pro Glu Glu Leu Arg Ala Ala Val
 50                  55                  60
Leu Gln Leu Arg Glu Thr Val Gln Gln Lys Glu Thr Leu Gly Ala
 65                  70                  75                  80
Gln Arg Glu Ala Ile Arg Glu Leu Thr Ser Lys Leu Ala Arg Cys Glu
                85                  90                  95
Gly Leu Ala Gly Gly Lys Ala Arg Gly Thr Gly Ala Thr Gly Lys Asp
                100                 105                 110
Thr Met Gly Asp Leu Pro Arg Asp Pro Gly His Val Val Glu Gln Leu
                115                 120                 125
Ser Arg Ser Leu Gln Thr Leu Lys Asp Arg Leu Glu Ser Leu Glu Leu
                130                 135                 140
Gln Leu His Thr Asn Ala Ser Asn Ala Gly Leu Pro Ser Asp Phe Arg
145                 150                 155                 160
Glu Val Leu Gln Arg Arg Leu Gly Glu Leu Glu Arg Gln Leu Leu Arg
                165                 170                 175
Lys Val Ala Glu Leu Glu Asp Glu Lys Ser Leu Leu His Asn Glu Thr
                180                 185                 190
Ser Ala His Arg Gln Lys Thr Glu Asn Thr Leu Asn Ala Leu Leu Gln
                195                 200                 205
Arg Val Thr Glu Leu Glu Arg Gly Asn Ser Ala Phe Lys Ser Pro Asp
                210                 215                 220
Ala Phe Lys Val Ser Leu Pro Leu Arg Thr Asn Tyr Leu Tyr Gly Lys
225                 230                 235                 240
Ile Lys Lys Thr Leu Pro Glu Leu Tyr Ala Phe Thr Ile Cys Leu Trp
                245                 250                 255
Leu Arg Ser Ser Ala Ser Pro Gly Ile Gly Thr Pro Phe Ser Tyr Ala
                260                 265                 270
Val Pro Gly Gln Ala Asn Glu Ile Val Leu Ile Glu Trp Gly Asn Asn
                275                 280                 285
Pro Ile Glu Leu Leu Ile Asn Asp Lys Val Ala Gln Leu Pro Leu Phe
                290                 295                 300
Val Ser Asp Gly Lys Trp His His Ile Cys Ile Thr Trp Thr Thr Arg
305                 310                 315                 320
Asp Gly Met Trp Glu Ala Phe Gln Asp Gly Glu Lys Leu Gly Thr Gly
                325                 330                 335
Glu Asn Leu Ala Pro Trp His Pro Ile Lys Pro Gly Gly Val Leu Ile
                340                 345                 350
Leu Gly Gln Glu Gln Asp Thr Val Gly Gly Arg Phe Asp Ala Thr Gln
                355                 360                 365
Ala Phe Val Gly Glu Leu Ser Gln Phe Asn Ile Trp Asp Arg Val Leu
                370                 375                 380
Arg Ala Gln Glu Ile Ile Asn Ile Ala Asn Cys Ser Thr Asn Met Pro
385                 390                 395                 400
Gly Asn Ile Ile Pro Trp Val Asp Asn Val Asp Val Phe Gly Gly
                405                 410                 415
Ala Ser Lys Trp Pro Val Glu Thr Cys Glu Glu Arg Leu Leu Asp Leu
                420                 425                 430
```

<210> SEQ ID NO 13
<211> LENGTH: 429
<212> TYPE: PRT
<213> ORGANISM: Mus musculus
<220> FEATURE:
<221> NAME/KEY: MISC_FEATURE
<222> LOCATION: (1)..(429)
<223> OTHER INFORMATION: Mouse NPTX2

<400> SEQUENCE: 13

```
Met Leu Ala Leu Leu Thr Val Gly Val Ala Leu Ala Val Ala Ala Gly
  1               5                  10                  15

Arg Ala Gln Asp Ser Pro Ile Pro Gly Ser Arg Phe Val Cys Thr Ala
                 20                  25                  30

Leu Pro Pro Glu Ala Ala Arg Ala Gly Cys Pro Leu Pro Ala Met Pro
             35                  40                  45

Met Gln Gly Gly Ala Leu Ser Pro Glu Glu Leu Arg Ala Ala Val
 50                  55                  60

Leu Gln Leu Arg Glu Thr Val Val Gln Gln Lys Glu Thr Leu Gly Ala
 65                  70                  75                  80

Gln Arg Glu Ala Ile Arg Glu Leu Thr Gly Lys Leu Ala Arg Cys Glu
                 85                  90                  95

Gly Leu Ala Gly Gly Lys Ala Arg Gly Thr Gly Lys Asp Thr Met Gly
            100                 105                 110

Asp Leu Pro Arg Asp Pro Gly His Val Val Glu Gln Leu Ser Arg Ser
            115                 120                 125

Leu Gln Thr Leu Lys Asp Arg Leu Glu Ser Leu Glu Leu Gln Leu Arg
130                 135                 140

Thr Asn Val Ser Asn Ala Gly Leu Pro Ser Asp Phe Arg Glu Val Leu
145                 150                 155                 160

Gln Arg Arg Leu Gly Glu Leu Glu Arg Gln Leu Leu Arg Lys Val Ala
                165                 170                 175

Glu Leu Glu Asp Glu Lys Ser Leu Leu His Asn Glu Thr Ser Ala His
            180                 185                 190

Arg Gln Lys Thr Glu Ser Thr Leu Asn Ala Leu Leu Gln Arg Val Thr
            195                 200                 205

Glu Leu Glu Arg Gly Asn Ser Ala Phe Lys Ser Pro Asp Ala Phe Lys
210                 215                 220

Val Ser Leu Pro Leu Arg Thr Asn Tyr Leu Tyr Gly Lys Ile Lys Lys
225                 230                 235                 240

Thr Leu Pro Glu Leu Tyr Ala Phe Thr Ile Cys Leu Trp Leu Arg Ser
                245                 250                 255

Ser Ala Ser Pro Gly Ile Gly Thr Pro Phe Ser Tyr Ala Val Pro Gly
            260                 265                 270

Gln Ala Asn Glu Ile Val Leu Ile Glu Trp Gly Asn Asn Pro Ile Glu
            275                 280                 285

Leu Leu Ile Asn Asp Lys Val Ala Gln Leu Pro Leu Phe Val Ser Asp
290                 295                 300

Gly Lys Trp His His Ile Cys Ile Thr Trp Thr Thr Arg Asp Gly Met
305                 310                 315                 320

Trp Glu Ala Phe Gln Asp Gly Glu Lys Leu Gly Thr Gly Glu Asn Leu
                325                 330                 335

Ala Pro Trp His Pro Ile Lys Pro Gly Gly Val Leu Ile Leu Gly Gln
            340                 345                 350
```

Glu Gln Asp Thr Val Gly Gly Arg Phe Asp Ala Thr Gln Ala Phe Val
            355                 360                 365

Gly Glu Leu Ser Gln Phe Asn Ile Trp Asp Arg Val Leu Arg Ala Gln
        370                 375                 380

Glu Ile Ile Asn Ile Ala Asn Cys Ser Thr Asn Met Pro Gly Asn Ile
385                 390                 395                 400

Ile Pro Trp Val Asp Asn Asn Val Asp Val Phe Gly Gly Ala Ser Lys
                405                 410                 415

Trp Pro Val Glu Thr Cys Glu Glu Arg Leu Leu Asp Leu
            420                 425

<210> SEQ ID NO 14
<211> LENGTH: 431
<212> TYPE: PRT
<213> ORGANISM: Homo sapiens
<220> FEATURE:
<221> NAME/KEY: MISC_FEATURE
<222> LOCATION: (29)..(29)
<223> OTHER INFORMATION: Mutated NPTX2 used as standard protein to
      prevent aggregation. Amino acid 29 mutated from cysteine to
      serine.
<220> FEATURE:
<221> NAME/KEY: MISC_FEATURE
<222> LOCATION: (41)..(41)
<223> OTHER INFORMATION: Mutated NPTX2 used as standard protein to
      prevent aggregation. Amino acid 41 mutated from cysteine to
      serine.
<220> FEATURE:
<221> NAME/KEY: MISC_FEATURE
<222> LOCATION: (94)..(94)
<223> OTHER INFORMATION: Mutated NPTX2 used as standard protein to
      prevent aggregation. Amino acid 94 mutated from cysteine to
      serine.

<400> SEQUENCE: 14

Met Leu Ala Leu Leu Ala Ala Ser Val Ala Leu Ala Val Ala Ala Gly
1               5                   10                  15

Ala Gln Asp Ser Pro Ala Pro Gly Ser Arg Phe Val Ser Thr Ala Leu
            20                  25                  30

Pro Pro Glu Ala Val His Ala Gly Ser Pro Leu Pro Ala Met Pro Met
        35                  40                  45

Gln Gly Gly Ala Gln Ser Pro Glu Glu Leu Arg Ala Ala Val Leu
    50                  55                  60

Gln Leu Arg Glu Thr Val Val Gln Gln Lys Glu Thr Leu Gly Ala Gln
65                  70                  75                  80

Arg Glu Ala Ile Arg Glu Leu Thr Gly Lys Leu Ala Arg Ser Glu Gly
            85                  90                  95

Leu Ala Gly Gly Lys Ala Arg Gly Ala Gly Ala Thr Gly Lys Asp Thr
        100                 105                 110

Met Gly Asp Leu Pro Arg Asp Pro Gly His Val Val Glu Gln Leu Ser
    115                 120                 125

Arg Ser Leu Gln Thr Leu Lys Asp Arg Leu Glu Ser Leu Glu His Gln
130                 135                 140

Leu Arg Ala Asn Val Ser Asn Ala Gly Leu Pro Gly Asp Phe Arg Glu
145                 150                 155                 160

Val Leu Gln Gln Arg Leu Gly Glu Leu Glu Arg Gln Leu Leu Arg Lys
            165                 170                 175

Val Ala Glu Leu Glu Asp Glu Lys Ser Leu Leu His Asn Glu Thr Ser
        180                 185                 190

Ala His Arg Gln Lys Thr Glu Ser Thr Leu Asn Ala Leu Leu Gln Arg
    195                 200                 205

```
Val Thr Glu Leu Glu Arg Gly Asn Ser Ala Phe Lys Ser Pro Asp Ala
    210                 215                 220

Phe Lys Val Ser Leu Pro Leu Arg Thr Asn Tyr Leu Tyr Gly Lys Ile
225                 230                 235                 240

Lys Lys Thr Leu Pro Glu Leu Tyr Ala Phe Thr Ile Cys Leu Trp Leu
                245                 250                 255

Arg Ser Ser Ala Ser Pro Gly Ile Gly Thr Pro Phe Ser Tyr Ala Val
                260                 265                 270

Pro Gly Gln Ala Asn Glu Ile Val Leu Ile Glu Trp Gly Asn Asn Pro
            275                 280                 285

Ile Glu Leu Leu Ile Asn Asp Lys Val Ala Gln Leu Pro Leu Phe Val
        290                 295                 300

Ser Asp Gly Lys Trp His His Ile Cys Val Thr Trp Thr Thr Arg Asp
305                 310                 315                 320

Gly Met Trp Glu Ala Phe Gln Asp Gly Glu Lys Leu Gly Thr Gly Glu
                325                 330                 335

Asn Leu Ala Pro Trp His Pro Ile Lys Pro Gly Gly Val Leu Ile Leu
                340                 345                 350

Gly Gln Glu Gln Asp Thr Val Gly Gly Arg Phe Asp Ala Thr Gln Ala
            355                 360                 365

Phe Val Gly Glu Leu Ser Gln Phe Asn Ile Trp Asp Arg Val Leu Arg
370                 375                 380

Ala Gln Glu Ile Val Asn Ile Ala Asn Cys Ser Thr Asn Met Pro Gly
385                 390                 395                 400

Asn Ile Ile Pro Trp Val Asp Asn Asn Val Asp Val Phe Gly Gly Ala
                405                 410                 415

Ser Lys Trp Pro Val Glu Thr Cys Glu Glu Arg Leu Leu Asp Leu
                420                 425                 430

<210> SEQ ID NO 15
<211> LENGTH: 432
<212> TYPE: PRT
<213> ORGANISM: Homo sapiens
<220> FEATURE:
<221> NAME/KEY: MISC_FEATURE
<222> LOCATION: (1)..(432)
<223> OTHER INFORMATION: Human NPTX1
<220> FEATURE:
<221> NAME/KEY: MISC_FEATURE
<222> LOCATION: (95)..(106)
<223> OTHER INFORMATION: Epitope used to produce monoclonal antibodies

<400> SEQUENCE: 15

Met Pro Ala Gly Arg Ala Ala Arg Thr Cys Ala Leu Leu Ala Leu Cys
1               5                   10                  15

Leu Leu Gly Ala Gly Ala Gln Asp Phe Gly Pro Thr Arg Phe Ile Cys
            20                  25                  30

Thr Ser Val Pro Val Asp Ala Asp Met Cys Ala Ala Ser Val Ala Ala
            35                  40                  45

Gly Gly Ala Glu Glu Leu Arg Ser Ser Val Leu Gln Leu Arg Glu Thr
50                  55                  60

Val Leu Gln Gln Lys Glu Thr Ile Leu Ser Gln Lys Glu Thr Ile Arg
65                  70                  75                  80

Glu Leu Thr Ala Lys Leu Gly Arg Cys Glu Ser Gln Ser Thr Leu Asp
                85                  90                  95

Pro Gly Ala Gly Glu Ala Arg Ala Gly Gly Gly Arg Lys Gln Pro Gly
            100                 105                 110
```

Ser Gly Lys Asn Thr Met Gly Asp Leu Ser Arg Thr Pro Ala Ala Glu
            115                 120                 125

Thr Leu Ser Gln Leu Gly Gln Thr Leu Gln Ser Leu Lys Thr Arg Leu
        130                 135                 140

Glu Asn Leu Glu Gln Tyr Ser Arg Leu Asn Ser Ser Gln Thr Asn
145                 150                 155                 160

Ser Leu Lys Asp Leu Leu Gln Ser Lys Ile Asp Glu Leu Glu Arg Gln
            165                 170                 175

Val Leu Ser Arg Val Asn Thr Leu Glu Glu Gly Lys Gly Pro Arg
        180                 185                 190

Asn Asp Thr Glu Glu Arg Val Lys Ile Glu Thr Ala Leu Thr Ser Leu
            195                 200                 205

His Gln Arg Ile Ser Glu Leu Glu Lys Gly Gln Lys Asp Asn Arg Pro
        210                 215                 220

Gly Asp Lys Phe Gln Leu Thr Phe Pro Leu Arg Thr Asn Tyr Met Tyr
225                 230                 235                 240

Ala Lys Val Lys Lys Ser Leu Pro Glu Met Tyr Ala Phe Thr Val Cys
            245                 250                 255

Met Trp Leu Lys Ser Ser Ala Thr Pro Gly Val Gly Thr Pro Phe Ser
        260                 265                 270

Tyr Ala Val Pro Gly Gln Ala Asn Glu Leu Val Leu Ile Glu Trp Gly
            275                 280                 285

Asn Asn Pro Met Glu Ile Leu Ile Asn Asp Lys Val Ala Lys Leu Pro
        290                 295                 300

Phe Val Ile Asn Asp Gly Lys Trp His His Ile Cys Val Thr Trp Thr
305                 310                 315                 320

Thr Arg Asp Gly Val Trp Glu Ala Tyr Gln Asp Gly Thr Gln Gly Gly
            325                 330                 335

Ser Gly Glu Asn Leu Ala Pro Tyr His Pro Ile Lys Pro Gln Gly Val
        340                 345                 350

Leu Val Leu Gly Gln Glu Gln Asp Thr Leu Gly Gly Gly Phe Asp Ala
            355                 360                 365

Thr Gln Ala Phe Val Gly Glu Leu Ala His Phe Asn Ile Trp Asp Arg
        370                 375                 380

Lys Leu Thr Pro Gly Glu Val Tyr Asn Leu Ala Thr Cys Ser Thr Lys
385                 390                 395                 400

Ala Leu Ser Gly Asn Val Ile Ala Trp Ala Glu Ser His Ile Glu Ile
            405                 410                 415

Tyr Gly Gly Ala Thr Lys Trp Thr Phe Glu Ala Cys Arg Gln Ile Asn
        420                 425                 430

<210> SEQ ID NO 16
<211> LENGTH: 432
<212> TYPE: PRT
<213> ORGANISM: Mus musculus
<220> FEATURE:
<221> NAME/KEY: MISC_FEATURE
<222> LOCATION: (1)..(430)
<223> OTHER INFORMATION: Mouse NPTX1
<220> FEATURE:
<221> NAME/KEY: MISC_FEATURE
<222> LOCATION: (95)..(106)
<223> OTHER INFORMATION: Epitope used to produce monoclonal antibodies

<400> SEQUENCE: 16

Met Leu Ala Gly Arg Ala Ala Arg Thr Cys Ala Leu Leu Ala Leu Cys
1               5                   10                  15

```
Leu Leu Gly Ser Gly Ala Gln Asp Phe Gly Pro Thr Arg Phe Ile Cys
            20                  25                  30

Thr Ser Val Pro Val Asp Ala Asp Met Cys Ala Ala Ser Val Ala Ala
        35                  40                  45

Gly Gly Ala Glu Glu Leu Arg Ser Asn Val Leu Gln Leu Arg Glu Thr
    50                  55                  60

Val Leu Gln Gln Lys Glu Thr Ile Leu Ser Gln Lys Glu Thr Ile Arg
65                  70                  75                  80

Glu Leu Thr Thr Lys Leu Gly Arg Cys Glu Ser Gln Ser Thr Leu Asp
                85                  90                  95

Ser Gly Pro Gly Glu Ala Arg Ser Gly Gly Arg Lys Gln Pro Gly
            100                 105                 110

Ser Gly Lys Asn Thr Met Gly Asp Leu Ser Arg Thr Pro Ala Ala Glu
            115                 120                 125

Thr Leu Ser Gln Leu Gly Gln Thr Leu Gln Ser Leu Lys Thr Arg Leu
    130                 135                 140

Glu Asn Leu Glu Gln Tyr Ser Arg Leu Asn Ser Ser Ser Gln Thr Asn
145                 150                 155                 160

Ser Leu Lys Asp Leu Leu Gln Ser Lys Ile Asp Asp Leu Glu Arg Gln
                165                 170                 175

Val Leu Ser Arg Val Asn Thr Leu Glu Glu Gly Lys Gly Gly Pro Lys
            180                 185                 190

Asn Asp Thr Glu Glu Arg Ala Lys Ile Glu Ser Ala Leu Thr Ser Leu
            195                 200                 205

His Gln Arg Ile Ser Glu Leu Glu Lys Gly Gln Lys Asp Asn Arg Pro
    210                 215                 220

Gly Asp Lys Phe Gln Leu Thr Phe Pro Leu Arg Thr Asn Tyr Met Tyr
225                 230                 235                 240

Ala Lys Val Lys Lys Ser Leu Pro Glu Met Tyr Ala Phe Thr Val Cys
                245                 250                 255

Met Trp Leu Lys Ser Ser Ala Ala Pro Gly Val Gly Thr Pro Phe Ser
            260                 265                 270

Tyr Ala Val Pro Gly Gln Ala Asn Glu Leu Val Leu Ile Glu Trp Gly
            275                 280                 285

Asn Asn Pro Met Glu Ile Leu Ile Asn Asp Lys Val Ala Lys Leu Pro
290                 295                 300

Phe Val Ile Asn Asp Gly Lys Trp His His Ile Cys Val Thr Trp Thr
305                 310                 315                 320

Thr Arg Asp Gly Val Trp Glu Ala Tyr Gln Asp Gly Thr Gln Gly Gly
                325                 330                 335

Asn Gly Glu Asn Leu Ala Pro Tyr His Pro Ile Lys Pro Gln Gly Val
            340                 345                 350

Leu Val Leu Gly Gln Glu Gln Asp Thr Leu Gly Gly Phe Asp Ala
    355                 360                 365

Thr Gln Ala Phe Val Gly Glu Leu Ala His Phe Asn Ile Trp Asp Arg
    370                 375                 380

Lys Leu Thr Pro Gly Glu Val Tyr Asn Leu Ala Thr Cys Ser Ser Lys
385                 390                 395                 400

Ala Leu Ser Gly Asn Val Ile Ala Trp Ala Glu Ser Gln Ile Glu Ile
                405                 410                 415

Phe Gly Gly Ala Thr Lys Trp Thr Phe Glu Ala Cys Arg Gln Ile Asn
            420                 425                 430
```

<210> SEQ ID NO 17
<211> LENGTH: 12
<212> TYPE: PRT
<213> ORGANISM: Artificial Sequence
<220> FEATURE:
<223> OTHER INFORMATION: Epitope/synthetic peptide from human NPTX2 used
      to produce monoclonal antibodies

<400> SEQUENCE: 17

Met Gln Gly Gly Ala Gln Ser Pro Glu Glu Glu Leu
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Epitope/synthetic peptide used to produce NPTX1
      monoclonal antibodies

<400> SEQUENCE: 18

Leu Asp Pro Gly Ala Gly Glu Ala Arg Ala Gly Gly
1               5                   10

<210> SEQ ID NO 19
<211> LENGTH: 27
<212> TYPE: DNA
<213> ORGANISM: Artificial Sequence
<220> FEATURE:
<223> OTHER INFORMATION: NPTX2 forward primer

<400> SEQUENCE: 19
gcaaggatcc caagcccagg ataaccc                                          27

<210> SEQ ID NO 20
<211> LENGTH: 30
<212> TYPE: DNA
<213> ORGANISM: Artificial Sequence
<220> FEATURE:
<223> OTHER INFORMATION: NPTX2 reverse primer

<400> SEQUENCE: 20
catgtcgact catgcactgt tgcctctctc                                       30

<210> SEQ ID NO 21
<211> LENGTH: 21
<212> TYPE: RNA
<213> ORGANISM: Artificial Sequence
<220> FEATURE:
<223> OTHER INFORMATION: Mut NPTX2

<400> SEQUENCE: 21
ucucuucuca ucugguccga a                                                21

<210> SEQ ID NO 22
<211> LENGTH: 22
<212> TYPE: RNA
<213> ORGANISM: Artificial Sequence
<220> FEATURE:
<223> OTHER INFORMATION: WT NPTX2

<400> SEQUENCE: 22
ucucuucuca ucuggugcca aa                                               22

<210> SEQ ID NO 23
<211> LENGTH: 23

```
<212> TYPE: RNA
<213> ORGANISM: Artificial Sequence
<220> FEATURE:
<223> OTHER INFORMATION: miR-96

<400> SEQUENCE: 23
ucguuuuuac acgaucacgg uuu                                            23

<210> SEQ ID NO 24
<211> LENGTH: 22
<212> TYPE: RNA
<213> ORGANISM: Artificial Sequence
<220> FEATURE:
<223> OTHER INFORMATION: miR-1271

<400> SEQUENCE: 24
acucacgaac gauccacggu uc                                             22

<210> SEQ ID NO 25
<211> LENGTH: 24
<212> TYPE: RNA
<213> ORGANISM: Artificial Sequence
<220> FEATURE:
<223> OTHER INFORMATION: miR-182

<400> SEQUENCE: 25
ucacacucaa gaugguaacg guuu                                           24

<210> SEQ ID NO 26
<211> LENGTH: 123
<212> TYPE: PRT
<213> ORGANISM: Artificial Sequence
<220> FEATURE:
<223> OTHER INFORMATION: Heavy chain VH sequence; mouse anti-NPTX1 McAb
      Clone 30#

<400> SEQUENCE: 26

Gln Val Thr Leu Lys Glu Ser Gly Pro Gly Ile Leu Lys Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Lys Phe Tyr Asn Pro Ser
    50                  55                  60

Leu Lys Ser Gln Leu Thr Val Ser Lys Asp Ala Ser Arg Asn Gln Val
65                  70                  75                  80

Phe Leu Lys Ile Thr Ser Val Asp Thr Ala Asp Ser Ala Thr Tyr Tyr
                85                  90                  95

Cys Ala Arg Arg Pro Tyr Gly Tyr Gly Asp Tyr Tyr Ala Leu Asp Tyr
            100                 105                 110

Trp Gly Pro Gly Thr Ser Val Thr Val Ser Ser
        115                 120

<210> SEQ ID NO 27
<211> LENGTH: 112
<212> TYPE: PRT
<213> ORGANISM: Artificial Sequence
<220> FEATURE:
<223> OTHER INFORMATION: Light chain VL sequence; mouse anti-NPTX1 McAb
      Clone 30#

<400> SEQUENCE: 27
```

-continued

Asn Ile Met Met Thr Gln Ser Pro Ser Ser Leu Ala Val Ser Ala Gly
1               5                   10                  15

Glu Lys Val Thr Met Ser Cys Lys Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Asn Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Leu Ser Ser Tyr Thr Phe Gly Gly Gly Thr Lys Leu Glu Ile Lys
            100                 105                 110

<210> SEQ ID NO 28
<211> LENGTH: 114
<212> TYPE: PRT
<213> ORGANISM: Artificial Sequence
<220> FEATURE:
<223> OTHER INFORMATION: Heavy chain VH sequence; mouse anti-NPTX2 McAb
      Clone 1#

<400> SEQUENCE: 28

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ala Met His Trp Val Lys Gln Ala Pro Gly Lys Gly Leu Lys Trp Met
        35                  40                  45

Gly Trp Ile Asn Thr Glu Thr Gly Val Thr Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Thr Ala Thr Tyr Phe Cys
                85                  90                  95

Ala Arg Glu Arg Tyr Gly Asp Trp Gly Gln Gly Thr Thr Leu Thr Val
            100                 105                 110

Ser Ser

<210> SEQ ID NO 29
<211> LENGTH: 112
<212> TYPE: PRT
<213> ORGANISM: Artificial Sequence
<220> FEATURE:
<223> OTHER INFORMATION: Light chain VL sequence; mouse anti-NPTX2 McAb
      Clone 1#

<400> SEQUENCE: 29

Asp Ile Val Met Ser Gln Ser Pro Ser Ser Leu Ala Val Ser Val Gly
1               5                   10                  15

Glu Lys Ile Thr Met Ser Cys Lys Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr

```
                65                  70                  75                  80
Ile Ser Ser Val Lys Ala Glu Asp Leu Ala Val Tyr Tyr Cys Gln Gln
                85                  90                  95

Tyr Tyr Thr Tyr Pro Thr Phe Gly Gly Gly Thr Lys Val Glu Ile Lys
            100                 105                 110

<210> SEQ ID NO 30
<211> LENGTH: 114
<212> TYPE: PRT
<213> ORGANISM: Artificial Sequence
<220> FEATURE:
<223> OTHER INFORMATION: Heavy chain VH sequence; mouse anti-NPTX2 McAb
      Clone 14#

<400> SEQUENCE: 30

Gln Ile Gln Leu Val Gln Ser Gly Pro Glu Leu Arg Lys Pro Gly Glu
1               5                   10                  15

Thr Val Lys Ile Ser Cys Lys Ala Ser Gly Tyr Thr Phe Thr Asp Tyr
            20                  25                  30

Ala Met His Trp Val Lys Gln Ala Pro Gly Lys Gly Leu Lys Trp Met
        35                  40                  45

Gly Trp Ile Asn Thr Gly Thr Gly Met Thr Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Thr Leu Lys Asn Glu Asp Thr Ala Thr Tyr Phe Cys
                85                  90                  95

Ala Arg Glu Arg Tyr Gly Asp Trp Gly Gln Gly Thr Ser Leu Thr Val
            100                 105                 110

Ser Ser

<210> SEQ ID NO 31
<211> LENGTH: 112
<212> TYPE: PRT
<213> ORGANISM: Artificial Sequence
<220> FEATURE:
<223> OTHER INFORMATION: Light chain VL sequence; mouse anti-NPTX2 McAb
      Clone 14#

<400> SEQUENCE: 31

Asp Ile Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Thr Phe Pro Thr Phe Gly Gly Gly Thr Lys Val Glu Ile Lys
            100                 105                 110

<210> SEQ ID NO 32
<211> LENGTH: 142
<212> TYPE: PRT
<213> ORGANISM: Artificial Sequence
```

<220> FEATURE:
<223> OTHER INFORMATION: Signal peptide plus heavy chain VH sequence;
    mouse anti-NPTX1 McAb Clone 30#
<220> FEATURE:
<221> NAME/KEY: SIGNAL
<222> LOCATION: (1)..(19)

<400> SEQUENCE: 32

Met Gly Arg Leu Thr Phe Ser Phe Leu Leu Ile Val Pro Ala Tyr
1               5                   10                  15

Val Leu Ser Gln Val Thr Leu Lys Glu Ser Gly Pro Gly Ile Leu Lys
            20                  25                  30

Pro Ser Gln Thr Leu Ser Leu Thr Cys Ser Phe Ser Gly Phe Ser Leu
            35                  40                  45

Ser Thr Ser Gly Met Gly Val Gly Trp Ile Arg Gln Pro Ser Gly Lys
    50                  55                  60

Gly Leu Glu Trp Leu Ala His Ile Trp Trp Asp Asp Lys Phe Tyr
65                  70                  75                  80

Asn Pro Ser Leu Lys Ser Gln Leu Thr Val Ser Lys Asp Ala Ser Arg
                85                  90                  95

Asn Gln Val Phe Leu Lys Ile Thr Ser Val Thr Ala Asp Ser Ala
            100                 105                 110

Thr Tyr Tyr Cys Ala Arg Arg Pro Tyr Gly Tyr Gly Asp Tyr Tyr Ala
            115                 120                 125

Leu Asp Tyr Trp Gly Pro Gly Thr Ser Val Thr Val Ser Ser
            130                 135                 140

<210> SEQ ID NO 33
<211> LENGTH: 136
<212> TYPE: PRT
<213> ORGANISM: Artificial Sequence
<220> FEATURE:
<223> OTHER INFORMATION: Signal peptide and light chain VL sequence;
    mouse anti-NPTX1 McAb clone 30#
<220> FEATURE:
<221> NAME/KEY: SIGNAL
<222> LOCATION: (1)..(24)

<400> SEQUENCE: 33

Met Gly Phe Lys Met Glu Ser Gln Thr Gln Val Phe Leu Ser Leu Leu
1               5                   10                  15

Leu Trp Val Ser Gly Thr Cys Gly Asn Ile Met Met Thr Gln Ser Pro
            20                  25                  30

Ser Ser Leu Ala Val Ser Ala Gly Glu Lys Val Thr Met Ser Cys Lys
            35                  40                  45

Ser Ser Gln Ser Val Leu Tyr Ser Ser Asn Gln Lys Asn Tyr Leu Ala
    50                  55                  60

Trp Tyr Gln Gln Lys Pro Gly Gln Ser Pro Lys Leu Leu Ile Asn Trp
65                  70                  75                  80

Ala Ser Thr Arg Glu Ser Gly Val Pro Asp Arg Phe Thr Gly Ser Gly
            85                  90                  95

Ser Gly Thr Asp Phe Thr Leu Thr Ile Ser Ser Val Gln Ala Glu Asp
            100                 105                 110

Leu Ala Val Tyr Tyr Cys His Gln Tyr Leu Ser Ser Tyr Thr Phe Gly
            115                 120                 125

Gly Gly Thr Lys Leu Glu Ile Lys
            130                 135

<210> SEQ ID NO 34

```
<211> LENGTH: 133
<212> TYPE: PRT
<213> ORGANISM: Artificial Sequence
<220> FEATURE:
<223> OTHER INFORMATION: Signal peptide and heavy chain VH sequence;
      mouse anti-NPTX2 McAb Clone 1#
<220> FEATURE:
<221> NAME/KEY: SIGNAL
<222> LOCATION: (1)..(19)

<400> SEQUENCE: 34

Met Asp Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asp Tyr Ala Met His Trp Val Lys Gln Ala Pro Gly Lys Gly Leu
    50                  55                  60

Lys Trp Met Gly Trp Ile Asn Thr Glu Thr Gly Val Thr Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Thr Leu Lys Asn Glu Asp Thr Ala Thr
            100                 105                 110

Tyr Phe Cys Ala Arg Glu Arg Tyr Gly Asp Trp Gly Gln Gly Thr Thr
        115                 120                 125

Leu Thr Val Ser Ser
    130

<210> SEQ ID NO 35
<211> LENGTH: 132
<212> TYPE: PRT
<213> ORGANISM: Artificial Sequence
<220> FEATURE:
<223> OTHER INFORMATION: Signal peptide and light chain VL sequence;
      mouse anti-NPTX2 McAb clone 1#
<220> FEATURE:
<221> NAME/KEY: SIGNAL
<222> LOCATION: (1)..(20)

<400> SEQUENCE: 35

Met Glu Ser Gln Thr Gln Val Leu Met Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Val Gly Glu Lys Ile Thr Met Ser Cys Lys Ser Ser Gln Ser
        35                  40                  45

Leu Leu Tyr Ser Ser Asn Gln Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Lys Ala Glu Asp Leu Ala Val Tyr
            100                 105                 110

Tyr Cys Gln Gln Tyr Tyr Thr Tyr Pro Thr Phe Gly Gly Gly Thr Lys
        115                 120                 125

Val Glu Ile Lys
    130
```

```
<210> SEQ ID NO 36
<211> LENGTH: 133
<212> TYPE: PRT
<213> ORGANISM: Artificial Sequence
<220> FEATURE:
<223> OTHER INFORMATION: Signal peptide and heavy chain VH sequence;
      mouse anti-NPTX2 McAb clone 14#
<220> FEATURE:
<221> NAME/KEY: SIGNAL
<222> LOCATION: (1)..(19)

<400> SEQUENCE: 36

Met Asp Trp Val Trp Thr Leu Leu Phe Leu Met Ala Ala Ala Gln Ser
1               5                   10                  15

Ile Gln Ala Gln Ile Gln Leu Val Gln Ser Gly Pro Glu Leu Arg Lys
            20                  25                  30

Pro Gly Glu Thr Val Lys Ile Ser Cys Lys Ala Ser Gly Tyr Thr Phe
        35                  40                  45

Thr Asp Tyr Ala Met His Trp Val Lys Gln Ala Pro Gly Lys Gly Leu
    50                  55                  60

Lys Trp Met Gly Trp Ile Asn Thr Gly Thr Gly Met Thr Thr Tyr Ala
65                  70                  75                  80

Asp Asp Phe Lys Gly Arg Phe Ala Phe Ser Leu Glu Thr Ser Ala Ser
                85                  90                  95

Thr Ala Tyr Leu Gln Ile Asn Thr Leu Lys Asn Glu Asp Thr Ala Thr
            100                 105                 110

Tyr Phe Cys Ala Arg Glu Arg Tyr Gly Asp Trp Gly Gln Gly Thr Ser
        115                 120                 125

Leu Thr Val Ser Ser
    130

<210> SEQ ID NO 37
<211> LENGTH: 130
<212> TYPE: PRT
<213> ORGANISM: Artificial Sequence
<220> FEATURE:
<223> OTHER INFORMATION: Signal peptide and light chain VL sequence;
      mouse anti-NPTX2 McAb clone 14#
<220> FEATURE:
<221> NAME/KEY: SIGNAL
<222> LOCATION: (1)..(18)

<400> SEQUENCE: 37

Met Lys Leu Pro Val Arg Leu Leu Val Leu Trp Val Ser Gly Thr
1               5                   10                  15

Cys Gly Asp Ile Val Met Ser Gln Ser Pro Ser Ser Leu Ala Val Ser
            20                  25                  30

Val Gly Glu Lys Ile Thr Met Ser Cys Lys Ser Ser Gln Ser Leu Leu
        35                  40                  45

Tyr Ser Ser Asn Gln Lys Asn Tyr Leu Ala Trp Tyr Gln Gln Lys Pro
    50                  55                  60

Gly Gln Ser Pro Lys Leu Leu Ile Tyr Trp Ala Ser Thr Arg Glu Ser
65                  70                  75                  80

Gly Val Pro Asp Arg Phe Thr Gly Ser Gly Ser Gly Thr Asp Phe Thr
                85                  90                  95
```

```
Leu Thr Ile Ser Ser Val Lys Ala Glu Asp Leu Ala Val Tyr Tyr Cys
            100                 105                 110

Gln Gln Tyr Tyr Thr Phe Pro Thr Phe Gly Gly Gly Thr Lys Val Glu
        115                 120                 125

Ile Lys
    130
```

BIOMARKERS OF COGNITIVE DYSFUNCTION

CROSS-REFERENCE TO RELATED APPLICATIONS

This application is a Continuation of U.S. patent application Ser. No. 15/511,860, filed Mar. 16, 2017, which is a 35 U.S.C. § 371 U.S. national entry of International Application PCT/US2015/050884, having an international filing date of Sep. 18, 2015, which claims the benefit of U.S. Provisional Application No. 62/219,867, filed Sep. 17, 2015, and U.S. Provisional Application No. 62/052,612, filed Sep. 19, 2014, the content of each of the aforementioned applications is herein incorporated by reference in their entireties.

STATEMENT OF GOVERNMENTAL INTEREST

This invention was made with government support under grant no. NS039156, awarded by the National Institutes of Health. The government has certain rights in the invention.

FIELD OF THE INVENTION

The present invention relates to the field of cognitive function. More specifically, the present invention provides compositions and methods useful for assessing cognitive dysfunction/function in Alzheimer's disease and other diseases of cognition.

INCORPORATION-BY-REFERENCE OF MATERIAL SUBMITTED ELECTRONICALLY

This application contains a sequence listing. It has been submitted electronically via EFS-Web as an ASCII text file entitled "P12095-03_ST25.txt." The sequence listing is 42,807 bytes in size, and was created on Sep. 18, 2015. It is hereby incorporated by reference in its entirety.

BACKGROUND OF THE INVENTION

Alzheimer's disease (AD) results in progressive loss of cognitive function. The most prevalent model of AD posits that amyloid peptide (AB) accumulates at synapses and prevents synaptic function required for information processing, storage and recovery. The histological hallmarks of AD are amyloid plaque, created by deposition of AB, and tangles created by deposition of hyper phosphorylated tau protein. Therapeutic approaches for AD focus on reduction of Aβ generation or deposition by inhibition of enzymes that generate Aβ or by approaches that increase the clearance of Aβ. Other strategies focus on molecular pathways involved in inflammation. Recent advances in brain imaging using PIB or related tracers allow for an assessment of amyloid load in brain of patients. The diagnosis of AD is also supported by measures of Aβ40/42 and phosphor tau in the cerebrospinal fluid, however, the magnitude of changes in these markers is modest, and not highly diagnostic in individual patients. With the advent of new therapies for AD there is a major need for simple markers that can be related to the disease pathogenesis and that are sufficiently robust to be useful for diagnosis and monitoring of treatment success.

SUMMARY OF THE INVENTION

The present invention is based, at least in part, on the discovery that neuronal pentraxin 2 (NPTX2) protein, which is normally present in the CSF, declines by several fold in patients with Alzheimer's disease. NPTX2 reduction occurs in association with a reduction of NPTX1, a co-functional protein that binds and regulates BACE1 activity. Reductions of NPTX1 and NPTX2 correlate with a standard assay of cognitive failure. Importantly, NPTX1 and NPTX2 reductions in CSF do not correlate with the current best markers including Aβ42 or ptau, which indicates that NPTX1/NPTX2 monitor a distinct pathophysiological process. Indeed, the present invention provides an orthogonal assay that can be used to stratify patients. Brain tissue levels of NPTX2 are also dramatically reduced in patients with AD. Because the molecular function of this protein family is mechanistically linked to activity of BACE I in rodent models and adaptation to altered brain activity, CSF levels are closely tied to AD pathogenesis. Thus, in certain embodiments, the NPTX2 biomarker is useful in the differential diagnosis of AD and in monitoring clinical course in combination with therapies. NPTX1 also declines in patients with Alzheimer's disease and other diseases of cognition. In particular embodiments, the biomarkers described herein can be used in assays designed to assess cognitive dysfunction/function in patients at risk for, having or likely to develop AD or other diseases of cognition.

In one aspect, the present invention relates to kits. In particular embodiments, the kits are useful for assessing, evaluating, determining, and/or measuring cognitive function in a patient. The patient may be suspected of having, has or is at risk of having cognitive dysfunction. In certain embodiments, the kit can be used to evaluate the effectiveness of a therapeutic treatment on cognitive function in a patient. In other embodiments, the kits are useful as a diagnostic test. Cognitive function/dysfunction in Alzheimer's Disease (AD) and other diseases or conditions of cognition can be evaluated including, but not limited to dementia, Parkinson's Disease (PD), down syndrome, schizophrenia, HIV-related dementia. Other diseases and conditions that can be evaluated using the methods and compositions of the present invention include brain injury (traumatic, subclinical and the like) as well as concussions and long term effects thereof.

Thus, in one embodiment, a kit comprises a binding agent or molecule that binds NPTX2. In another embodiment, a kit comprises a binding agent or molecule that binds NPTX1. In a specific embodiment, a kit comprises an antibody that specifically binds NPTX1 and/or an antibody that specifically binds NPTX2. The kit can further comprise an agent for reducing heterocomplexes comprising NPTX1 and NPTX2 present in a biological sample obtained from a patient into NPTX1 and NPTX2 monomers. In a further embodiment, the kit further comprises an agent that covalently modifies the thiol groups of the NPTX1 and NPTX2 monomers to prevent re-formation or re-aggregation of NPTX1/NPTX2 heterocomplexes. The kits of the present invention can further comprise instructions on using the kit to detect NPTX1 and/or NPTX2 by testing a biological sample obtained from a patient suspected of having, having or at risk of having cognitive dysfunction. The kits can be used to establish a baseline of cognitive function and assessed periodically, for example, during treatment or at a later time when cognitive function/dysfunction needs to be addressed (e.g., post-concussion or traumatic brain injury).

In a specific embodiment, a kit comprises (a) an antibody that specifically binds NPTX2; (b) an agent for reducing heterocomplexes comprising NPTX1 and NPTX2 present in a biological sample obtained from a patient into NPTX1 and NPTX2 monomers; and (c) an agent for covalently modifying the NPTX1 and NPTX2 monomers to prevent re-formation of NPTX1/NPTX2 heterocomplexes. The agent of step (b) can comprise a disulfide bond reducing agent including, for example, dithiothreitol (DTT), mercaptoethanol (beta-ME) and Tris(2-Carboxyethyl)-phosphine (TCEP); however, it is understood that any agent that separates the heterocomplexes into monomers can be used. In certain embodiments, the agent of step (c) covalently modifies the thiol groups of the NPTX1 and NPTX2 monomers. The agent can be a molecule or compound that reacts with thiols and modifies cysteine residues in the marker protein. For example, the thiol group blocker of step (c) can include, but is not limited to, N-ehtylmaleimide (NEM) and methyl methanethiosulfonate (MMTS). It is understood, however, that any agent that blocks re-formation of the NPTX1 and NPTX2 monomers into heterocomplexes, whether through thiol group blocking or not, can be used. It is contemplated that, in some embodiments, the agent can modify, bind, block, or react with one or both of NPTX1 and NPTX2 to prevent re-formation of heterocomplexes. In some embodiments, the agent blocks or prevents re-formation, through covalent modification (via thiol group blocking, for example) or by another mechanism, of the NPTX1 and NPTX2 monomers into heterocomplexes.

The kits of the present invention can further comprise a substrate. In another embodiment, the kit can comprise a positive control. In a specific embodiment, the positive control comprises a standard protein comprising the amino acid sequence of SEQ ID NO:11. In particular embodiments, the kit comprises a detection reagent. In a specific embodiment, the kit comprises a secondary antibody. In a more specific embodiment, the secondary agent is conjugated to a detection agent. In certain embodiments, the binding molecules can comprise a detection reagent. In one embodiment, an antibody can be biotinylated and the detection reagent can be, for example, avidin conjugated to horseradish peroxidase (HRP) and the like.

In particular embodiments, a binding agent or molecule comprises an antibody that specifically binds an epitope of NPTX2, wherein the epitope comprises SEQ ID NO:17. In a specific embodiment, a binding agent or molecule comprises the antibody produced by the hybridoma deposited under ATCC Accession No. PTA-122270. In an alternative embodiment, a binding agent or molecule comprises the antibody produced by the hybridoma deposited under ATCC Accession No. PTA-122271. The kits of the present invention can also comprise a binding molecule or agent that specifically binds NPTX1. In a specific embodiment, a binding agent or molecule that specifically binds NPTX1 comprises an antibody. In a more specific embodiment, the antibody specifically binds an epitope of NPTX1, wherein the epitope comprises SEQ ID NO:18. In an even more specific embodiment, the antibody comprises the antibody produced by the hybridoma deposited under ATCC Accession No. PTA-122269.

In another aspect, the present invention provides methods for assessing cognitive dysfunction in a patient. In one embodiment, the method comprises the steps of (a) reducing heterocomplexes comprising NPTX1 and NPTX2 present in a biological sample obtained from the patient into NPTX1 and NPTX2 monomers; (b) covalently modifying the thiol groups of the NPTX1 and NPTX2 monomers to prevent re-formation of NPTX1/NPTX2 heterocomplexes; (c) detecting NPTX2 in the sample; and (d) assessing cognitive function in the patient by comparing NPTX2 detected in the sample to a control. In a non-limiting embodiment, the control can be NPTX2 levels in age-matched controls. In a specific embodiment, detection step (c) further comprises detecting NPTX1 in the sample and assessment step (d) further comprises assessing cognitive function in the patient by comparing NPTX1 and NPTX2 detected in the sample to a control. In another specific embodiment, reducing step (a) comprises incubating the biological sample with DTT. In a further embodiment, covalent modification step (b) comprises incubating the biological sample with NEM. As discussed herein, it is contemplated that any method of separating or breaking up heterocomplexes into NPTX1 and NPTX2 monomers can be used (e.g., a reducing agent). In addition, it is contemplated that any method of preventing or blocking reformation of NPTX1 and NPTX2 monomers into heterocomplexes can be used (e.g., thiol group blockers).

In one embodiment, the biological sample is cerebrospinal fluid (CSF). In other embodiments, the biological sample comprises blood, plasma, serum or urine.

In particular embodiments, the detection of NPTX1 and/or NPTX2 can be accomplished using an enzyme linked immunosorbent assay (ELISA). In one embodiment, the ELISA comprises using the anti-NPTX2 monoclonal antibody produced by the hybridoma deposited under ATCC Accession No. PTA-122270. In another embodiment, the ELISA comprises using the anti-NPTX2 monoclonal antibody produced by the hybridoma deposited under ATCC Accession No. PTA-122271. In yet another embodiment, the ELISA comprises using the anti-NPTX1 monoclonal antibody produced by the hybridoma deposited under ATCC Accession No. PTA-122269.

In certain embodiments, the ELISA comprises using a standard protein having the amino acid sequence shown in SEQ ID NO:11. In a further embodiment, the ELISA comprises using an antibody that recognizes an epitope of NPTX2, wherein the epitope comprises SEQ ID NO:17. In yet another embodiment, the ELISA comprises using an antibody that recognizes an epitope of NPTX1, wherein the epitope comprises SEQ ID NO:18.

In a specific embodiment, the present invention provides a method comprising the steps of (a) reducing heterocomplexes comprising NPTX1 and NPTX2 present in a CSF sample obtained from the patient into NPTX1 and NPTX2 monomers; (b) covalently modifying the thiol groups of the NPTX1 and NPTX2 monomers to prevent re-formation of NPTX1/NPTX2 heterocomplexes; and detecting NPTX1 and/or NPTX2 in the sample using an ELISA. In a specific embodiment, reducing step (a) comprises incubating the biological sample with DTT. In another specific embodiment, covalent modification step (b) comprises incubating the biological sample with NEM.

In another embodiment, the ELISA comprises using the anti-NPTX2 monoclonal antibody produced by the hybridoma deposited under ATCC Accession No. PTA-122270. Alternatively, or in addition, the ELISA can comprise using the anti-NPTX2 monoclonal antibody produced by the hybridoma deposited under ATCC Accession No. PTA-122271. In a further embodiment, the ELISA comprises using the anti-NPTX1 monoclonal antibody produced by the hybridoma deposited under ATCC Accession No. PTA-122269. The ELISA can also comprise using a standard protein having the amino acid sequence shown in SEQ ID NO:11. In particular embodiments, the ELISA comprises using an antibody that recognizes an epitope of NPTX2, wherein the epitope comprises SEQ ID NO:17. In certain embodiments, the ELISA comprises using an antibody that recognizes an epitope of NPTX1, wherein the epitope comprises SEQ ID NO:18.

The method can further comprise providing a report showing the detected NPTX1 and/or NPTX2 levels. The report can further show controls levels including, for example, a cut-off value for cognitive function/dysfunction. An index or scale of NPTX1 and/or NPTX2 levels and a corresponding spectrum of cognitive function can also be provided. Detected levels can be plotted against currently accepted indexes or scales of cognitive function rating including, but example, Mattis dementia rating scale (Mattis DRS). The report can also provide a conclusion as to cognitive dysfunction/function, as well as a treatment recommendation/regimen. The report can also provide information as to previous measurements of NPTX1 and/or NPTX2 levels, for example, if the method was used to assess effectiveness of therapeutic treatment on cognitive function. Indeed, the present invention specifically contemplates use of the present methods and kits as a companion diagnostic to monitor patient treatment. In other embodiments, the present invention can be used to screen potential drug candidates to identify compounds that can restore NPTX1 and/or NPTX2 expression levels. In further embodiments, the present invention can be used to diagnose, prognose, or determine the risk of developing, AD and/or other diseases or conditions of cognition. In other embodiments, the present invention can be used to identify patients who may benefit from a treatment that increases expression of a biomarker protein described herein. In addition, the present invention provides methods of treatment for patient who have low expression of a biomarker protein described herein including NPTX1 and/or NPTX2.

In another aspect, the present invention provides antibodies. In one embodiment, the present invention provides an antibody having the characteristics of the antibody produced by the hybridoma deposited under ATCC Accession No. PTA-122269. In another embodiment, the present invention provides an antibody having the characteristics of the antibody produced by the hybridoma deposited under ATCC Accession No. PTA-122270. The present invention also provides an antibody having the characteristics of the antibody produced by the hybridoma deposited under ATCC Accession No. PTA-122271.

In certain embodiments, the present invention provides antibodies to NPTX1 and antibodies to NPTX2. In more particular embodiments, the present invention provides isolated antibodies that bind human NPTX1 and isolated antibodies that bind human NPTX2. In other embodiments, the present invention provides nucleotide sequences that encode an antibody that binds human NPTX1. The present invention further provides amino acid sequences that encode an antibody that binds human NPTX1. In other embodiments, the present invention provides nucleotide sequences that encode an antibody that binds human NPTX2. The present invention further provides amino acid sequences that encode an antibody that binds human NPTX2. The antibody can be a single chain variable fragment (scFv), a dimeric scFv, a Fab, a Fab', a F(ab')2 fragment or a full length antibody.

In specific embodiments, the antibody comprises a variable heavy chain comprising SEQ ID NO:26, SEQ IDNO: 28, SEQ ID NO:30, or fragments thereof. In other embodiments, the antibody comprises a variable heavy chain that is substantially identical to SEQ ID NO:26, SEQ IDNO:28, SEQ ID NO:30, or fragments thereof.

In certain embodiments, the antibody comprises a light chain comprising SEQ ID NO:27, SEQ ID NO:29, SEQ ID NO:31, or fragments thereof. Alternatively, the antibody comprises a variable light chain that is substantially identical to SEQ ID NO:27, SEQ ID NO:29, SEQ ID NO:31, or fragments thereof.

In certain embodiments, the present invention provides an NPTX1 antibody comprising a heavy chain comprising SEQ IDNO:26 or a fragment thereof and a light chain comprising SEQ ID NO:27 or a fragment thereof. The NPTX1 antibody can comprise a heavy chain comprising an amino acid sequence that is substantially identical to SEQ ID NO:26 or a fragment thereof and a light chain comprising an amino acid sequence that is substantially identical to SEQ ID NO:27 or a fragment thereof.

In certain embodiments, the present invention provides an NPTX2 antibody comprising a heavy chain comprising SEQ IDNO:28, SEQ ID NO:30 or a fragment thereof and a light chain comprising SEQ ID NO:29, SEQ ID NO:31 or a fragment thereof. The NPTX1 antibody can comprise a heavy chain comprising an amino acid sequence that is substantially identical to SEQ ID NO:28, SEQ ID NO:30 or a fragment thereof and a light chain comprising an amino acid sequence that is substantially identical to SEQ ID NO:29, SEQ ID NO:31 or a fragment thereof.

The present invention also provides methods and compositions for restoring NPTX2 levels as a treatment approach. The methods and compositions are directed to microRNAs that bind NPTX2. Anti-miRNA compositions that target miR-96, miR-182 and/or miR-1271 can be useful as a treatment to restore NPTX2 levels and thus, cognitive function.

BRIEF DESCRIPTION OF THE FIGURES

FIG. 17A-17H. NPTX2 levels are reduced in human postmortem AD brain and DS brain, but on in ASYMAD brain. (FIGS. 1A, 1B and 1D) Representative western blot images (A) and quantification of NPTX2 (B) and NPTX1 (D) in the frontopolar cortex (FPC), precuneus (PCU), occipital gyrus (OCC), middle frontal gyrus (MFG), middle temporal gyrus (MTG) and parietal gyrus (PAR) from controls and AD subjects. NPTX2 is down regulated in all assayed brain regions of AD individuals. FPC: n=7 for control and n=8 for AD; PCU: n=15 for control and n=19 for AD; OCC: n=7 for control and n=7 for AD; MFG: n=6 for control and n=11 for AD; MTG: n=4 for control and n=5 for AD; PAR: n=5 for control and n=5 for AD. $*p<0.05$, $p<0.01$, $*p<0.001$ by two-tailed t-test. (FIG. 17C) NPTX2 mRNA is reduced in AD FPC region. n=9 for control and n=16 for AD. $**p<0.01$ by two-tailed t-test. (FIG. 17E, 17F) Western blot assays reveal no significant change of NPX2 expression in MFG from subjects with asymptomatic AD (ASYMAD). n=8 for control, n=10 for ASYMAD. Two-tailed t-test was performed. (FIG. 17G, 17H) Representative western blot images and quantification of NPTX2 show significant reduction of NPTX2 in MFG of individuals with Down Syndrome (DS). n=7 per group. $*p<0.05$ by two-tailed t-test. (FIG. 17I) NPTX2 mRNA is reduced in MFG of DS individuals. n=6 per group. $*p<0.05$ by two-tailed t-test. Data represent mean±SEM. See also FIG. 21-22.

(FIG. 18A) NPTX2 pre-mRNA level is identical in FPC of AD subjects and control. FPC: frontopolar cortex. n=9 for control and n=16 for AD. Two-tailed t-test was performed. (FIG. 18B) microRNAs are predicted to bind with NPTX2 3'UTR by TargetScan. (FIG. 18C-18E) Taqman assays show miR-182 and miR-1271 are increased in FPC of AD individuals, and correlate with reduced NPTX2 mRNA. n=9 for control and n=16 for AD. $*p<0.05$, $**p<0.01$ by two-tailed t-test. Pearson correlation coefficient analysis was performed in 2D and 2E. (FIG. 18F-18I) Cultured mouse cortical neurons are transduced with lentiviral vector encoding nontargeting miRNA (NT) or miR-96, miR-1271 and miR-182. (FIG. 18G) Expression of miR-96, miR-1271 and miR-182 reduce NPTX2 protein level. (FIG. 18H) miR-96 reduce NPTX2 mRNA as well. (FIG. 18I)NPTX2 pre-mRNA is preserved by miR-96 and miR-1271 expression. n=5 wells from three independent culture except n=4 wells for LV NT group in FIG. 2G. $*p<0.05$, $***p<0.001$ by nonparametric one way ANOVA with Tukey post hoc test. Data represent mean±SEM. See also FIG. 23-25.

(FIG. 19A) Time course of freezing to context (sec) observed in NPTX2$^{-/-}$ and control WT mice during training in a delayed fear conditioning with strong (left panel) or mild (right panel) US. Triangles indicate CS-US pairings. X axis show 15-sec blocks during intertrial intervals. (FIG. 19B) Final levels of freezing (%) to context and CS acquired at the end of the training session. (FIG. 19C, 3D) Time course of freezing (sec) (3C) and average percent of freezing (3D) to the training context after a 24-hr delay. (FIG. 19E) Average percent of freezing to CS tested after a 26-hr delay in a new context. (FIG. 19F) Time course of freezing (sec) in new context before and after presentation of CS (shown as arrows). (FIG. 19G) Average percent of freezing before, during and after presentations of CS in new context. Asterisks in 3A-3G show significant differences between NPTX2$^{-/-}$ and control mice as results of post-hoc tests applied to significant main effect of genotype or genotype x block interaction ($p<0.05$; ANOVA). Numbers of cases shown in 3A are the same for 3A-3G. (FIG. 19H) Aβ40 and Aβ42 are increased in 3 month-old hAPP/NPTX2$^{-/-}$ mice compared with hAPP mice. n=8 per group. $p<0.01$, $*p<0.001$ by two-tailed t-test. (FIG. 19I) Specific APP antibody (6E10) staining and silver staining reveal plaque in hAPP/NPTX2$^{-/-}$ mice at 3 months, whereas there is no Aβ plaque detected in hAPP mice at the same age. n=8-16 per group including both male and female mice. Data represent mean±SEM. See also FIG. 26.

(FIG. 20A, 20B) Representative western blot images and quantification of NPTX2, NPTX1 and NPTXR in lumbar cerebrospinal fluid (CSF) from patients with clinical diagnosed AD. AD patients show reduced NPTX2 and NPTX1 levels in CSF compared with healthy controls. n=36 for control, n=30 for AD. $p<0.01$, $*p<0.001$ by two-tailed t-test. (FIG. 20C) AD patients with lower MMSE scores have less NPTX2 and NPTX1 in CSF than patients with higher MMSE scores and controls. MMSE: Mini Mental Status Exam. $*p<0.05$, $p<0.01$, $*p<0.001$ by two-tailed t-test. (FIG. 20D) No correlation is observed between NPTX2 and Aβ42 in CSF from patients with AD and MCI. n=26 for AD, n=5 for MCI. Pearson correlation coefficient analysis was performed. (FIG. 20E) ELISA was developed to quantitate NPTX2 protein in CSF. NPTX2 ELISA shows significant reduction of NPTX2 in CSF from patients with clinical diagnosed AD. n=36 for control, n=28 for AD. $*p<0.001$ by two-tailed t-test. (FIG. 20F) Receiver operating characteristic (ROC) curve analysis of CSF NPTX2 as an AD biomarker. The area under ROC curve (AUC) is 0.8178. Sensitivity is 69.49%, and specificity is 83.33% when "cut-off" point is 556.7 pg/ml, which was determined by maximizing Youden index value. n=72 for control, n=58 for AD. (FIG. 20G) CSF NPTX2 levels are also significantly reduced in individuals with mild cognitive impairment (MCI) when compared with healthy controls. MCI, n=72 for control, n=17 for MCI. p<0.01 by two-tailed t-test. Data represent mean±SEM. See also FIG. 27-32.

(FIG. 22A) Representative western blots of Egr1 and Arc in the frontopolar cortex (FPC), precuneus gyrus (PCU), occipital gyrus (OCC), middle frontal gyms (MFG), middle temporal gyrus (MTG) and parietal gyrus (PAR) of control and AD individuals. (FIG. 22B) Quantitation of Western blots show that expression of Egr1 and Arc are not significantly altered in most-tested brain areas from AD individuals, except that there is moderate reduction of Arc in PCU and MFG from AD cases. FPC: n=7 for control and n=8 for AD; PCU: n=15 for control and n=19 for AD; OCC: n=7 for control and n=7 for AD; MFG: n=6 for control and n=11 for AD; MTG: n=4 for control and n=5 for AD; PAR: n=5 for control and n=5 for AD. *p<0.05 by two-tailed t-test. Data represent mean±SEM.

(FIG. 23A) Representative pyrosequencing traces show high methylation of NPTX2 promoter in pancreatic cell line AsPC1 cells, and low methylation in human brain. (FIG. 23B) NPTX2 promoter methylation is not different between control and AD subjects. n=8 per group. Two-tailed t-test was performed. Data represent mean±SEM.

(FIG. 24A) As in frontopolar cortex, NPTX2 mRNA is also reduced in precuneus (PCU) of AD subjects with preserved NPTX2 pre-mRNA. n=7 for control and n=6 for AD. (FIG. 24B) miR-152 and miR-182 are increased in AD PCU region compared with control. n=7 per group. *p<0.05, p<0.01, *p<0.001, two-tailed t-test. Data represent mean±SEM.

(FIG. 25A) Wild-type (WT) or miR-binding site mutated (Mut) NPTX2 3'UTR is inserted downstream of a luciferase reporter. Mutated nucleotides are in red. (FIG. 25B) miRNA mimics are able to reduce the luciferase activity in HEK293 cells, and this effect is partially abolished by mutation of miRNA binding site on NPTX2 3'UTR. n=9-16 wells. *miRNA mimic vs control RNA; #WT NPTX2 vs mutant NPTX2. Two-tailed t-test. Data represent mean±SEM.

FIG. 26A-26B. Behaviors of NPTX2$^{-/-}$ and WT mice in control tasks. Performance of NPTX2$^{-/-}$ mice was similar to WT mice in all control tasks including novelty-induced exploration in Y maze (FIG. 26A) and open field (FIG. 26B) and anxiety levels in Plus maze (c). NS-nonsignificant.

(FIG. 27A) NPTX2 and NPTX1 are detected in lumbar CSF of human subjects as a high molecular weight complex that is resolved into individual NPTXs with reducing reagent on SDS-PAGE. Arrows indicate monomer NPTX2 and NPTX1. BME: β-mercaptoethanol. (FIG. 27B) NPTX2 and NPTX1 expression in CSF correlate within samples. n=66 including 36 control and 30 AD samples. p<0.0001 by Pearson correlation coefficient analysis.

(FIG. 28A) No correlation is observed between NPTX1 and Aβ42 in CSF from patients with AD and MCI. MCI: mild cognitive impairment. n=26 for AD, n=5 for MCI. (FIG. 28B, 28C) CSF NPTXs correlate with CSF p-Tau181 in patients with AD and MCI. n=25 for AD, n=5 for MCI. (FIG. 28D, 28E) CSF NPTXs correlate with CSF Tau in patients with AD and MCI. n=25 for AD, n=5 for MCI. Pearson correlation coefficient analysis was performed.

(FIG. 29A, 29B) Representative western blot images and quantification of NPTX1, NPTX2 and NPTXR in CSF from patients with clinical frontotemporal dementia (FTD). NPTX2 and NPTX1 are reduced in CSF of FTD patients. n=6 for control, n=5 for FTD. (FIG. 29C, 29D) Representative western blot images and quantification of NPTX1, NPTX2 and NPTXR in CSF from patients with Parkinson's disease (PD), PD with mild cognitive impairment (PD-MCI) and dementia with Lewy bodies (DLB). NPTX2 and NPTX1 are reduced in CSF of DLB patients. n=36 for control, n=5 for PD, n=3 for PD-MCI and n=7 for DLB. *p<0.05, **p<0.01, two-tailed t-test. Data represent mean±SEM.

(FIG. 30A) Characterization of mouse monoclonal NPTX2 antibody. Western blots using mouse NPTX2 monoclonal antibody show a 50 kDa band in WT brain lysate which is absent in NPTX2$^{-/-}$ and NPTX1$^{-/-}$; NPTX2$^{-/-}$; NPTXR (triple knockout, TKO). (FIG. 30B) Purification of NPTX2 standard protein for NPTX2 ELISA assay. (FIG. 30C) NPTX2 ELISA assay correlates well with Western blot assay (WB). n=64 including 36 control and 28 AD samples. p<0.0001 by Pearson correlation coefficient analysis.

(FIG. 31A, 31B) Representative western blot images and quantification of NPTX2, NPTX1 and NPTXR in another set of lumbar CSF from patients with clinical diagnosed AD. AD patients show reduced NPTX2 and NPTX1 levels in CSF compared with healthy controls. n=36 for control, n=30 for AD. **p<0.01 by two-tailed t-test. (FIG. 31C) Patients with clinical diagnosed AD are divided into three groups based on Mattis DRS score. AD patients with lower DRS scores have less NPTX2 and NPTX1 in CSF than patients with higher DRS scores and controls. DRS: dementia rating scale. *p<0.05, **p<0.01, two-tailed t-test. (FIG. 31D) ELISA assay was developed to measure NPTX2 in CSF. Consistent with WB assay, ELISA assays show that CSF NPTX2 is reduced in AD patients, particularly in patients with lower DRS scores. n=36 for control, n=30 for AD. *p<0.05, **p<0.01, two-tailed t-test. (FIG. 31E) NPTX2 expression in CSF correlates with cognitive function assayed by Mattis DRS in AD group. n=29. p=0.0029 by Pearson correlation coefficient analysis. Data represent mean±SEM.

FIG. 34A, 34B: Representative western blot images and quantification of NPTX2, NPTX1 and NPTXR in lumbar CSF from patients with clinical diagnosed AD. AD patients show reduced NPTX2 and NPTX1 levels in CSF compared with healthy controls. n=36 for control, n=30 for AD. FIG. 34C: Patients with clinical diagnosed AD are divided into three groups based on Mattis DRS scores. AD patients with lower DRS scores have less NPTX2 and NPTX1 in CSF than patients with higher DRS scores and controls. FIG. 34D: ELISA assay was developed to measure NPTX2 in CSF. Consistent with WB assay, ELISA assays show that CSF NPTX2 is reduced in AD patients, particularly in patients with lower DRS scores. n=36 for control, n=30 for AD. FIG. 34E: NPTX2 expression in CSF correlates with cognitive function assayed by Mattis DRS in AD group. n=29. * p<0.05,  p<0.01, * p<0.001, two-tailed t test. Data represent mean±SEM.

STATEMENT OF DEPOSIT

Figure 1:
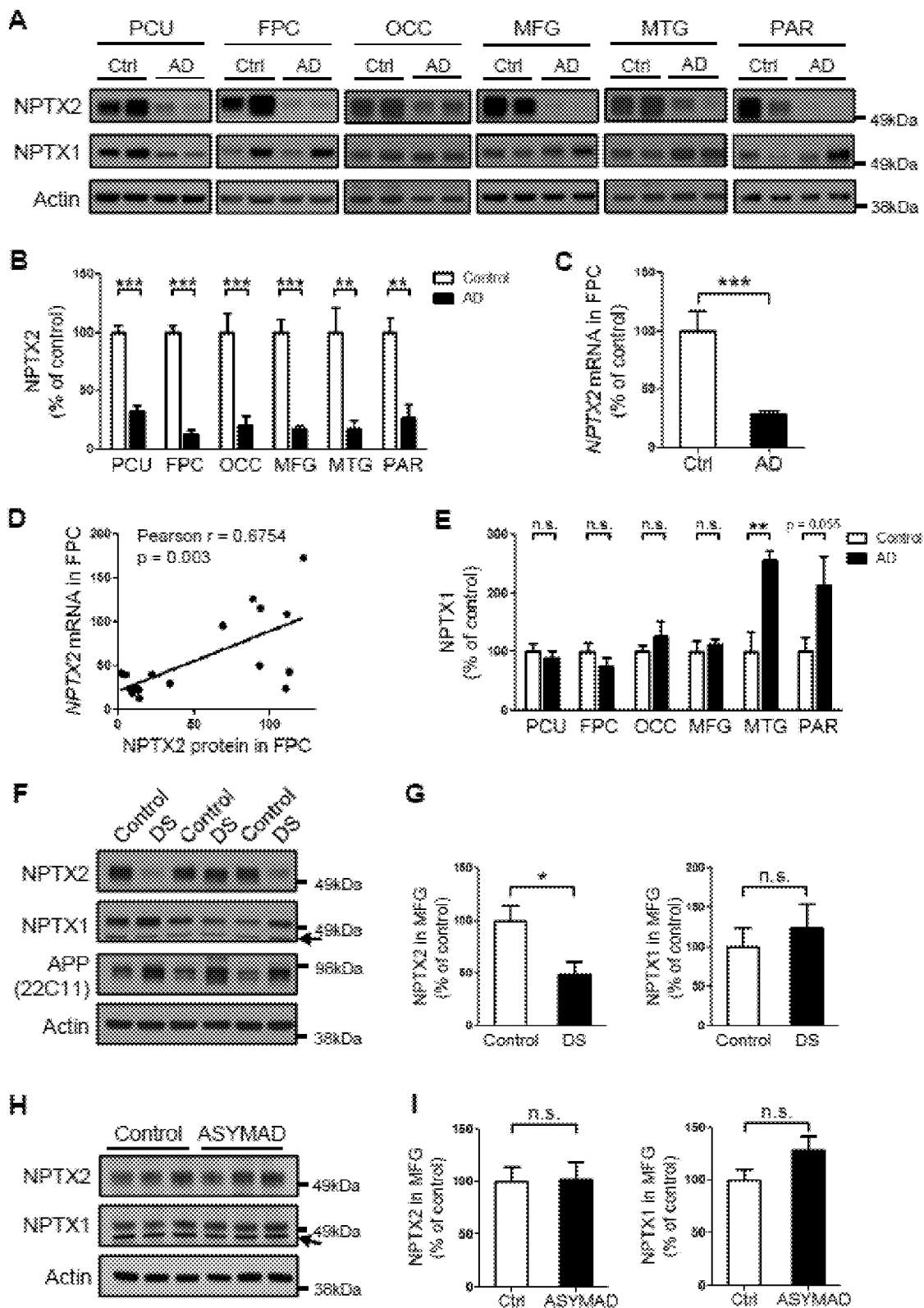
FIG. 1. NPTX levels are reduced in human postmortem AD brain and DS brain. (A, B and E) Representative western blot images (A) and quantification of NPTX2 (B) and NPTX1 (E) in the precuneus (PCU), frontal pole (FPC), occipital gyrus (OCC), middle frontal gyms (MFG), middle temporal gyrus (MTG) and parietal gyms (PAR) from controls and AD subjects. NPTX2 is down regulated in all assayed brain regions of AD individuals. PCU: n=17 for control and n=19 for AD; FPC: n=8 for control and n=9 for AD; OCC: n=8 for control and n=10 for AD; MFG: n=7 for control and n=11 for AD; MTG: n=5 for control and n=5 for AD; PAR: n=6 for control and n=5 for AD. (C) NPTX2 mRNA is reduced in AD FPC region. n=9 per group. (D) NPTX2 protein level correlates with mRNA level within samples in FPC region from control and AD individuals. (F, G) Representative western blot images and quantification of NPTX2 and NPTX1 show significant reduction of NPTX2 in MFG of individuals with Down Syndrome (DS). n=7 per group. (H, I) Representative western blot images and quantification show NPTX levels are not significantly altered in MFG from subjects with asymptomatic AD (ASYMAD). n=11 for control, n=12 for ASYMAD. Arrows indicate non-specific bands. Bands for NPTX1, NPTX2 and NPTXR were each cross-validated with two independent antibodies. * $p<0.05$,  $p<0.01$, * $p<0.001$, two-tailed t test. Data represent mean±SEM. See also FIG. 7.

Monoclonal antibodies (Mab) to NPTX1 and monoclonal antibodies to NPTX2 were deposited Jul. 1, 2015, under terms of the Budapest Treaty with the American Type Culture Collection (ATCC®), 10801 University Blvd., Manassas, Va. 20110. McAb cell NPTX1 30 # is produced by the hybridoma deposited under ATCC Accession No. PTA-122269. McAb cell NPTX2 1 # is produced by the hybridoma deposited under ATCC Accession No. PTA-122270. McAb cell NPTX2 14 # is produced by the hybridoma deposited under ATCC Accession No. PTA-122271. For the purposes of this invention, any Mab having the identifying characteristics of PTA-122269, PTA-122270 or PTA-122271, including subcultures and variants thereof which have the identifying characteristics and activity as described herein are included.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

As used herein, the term "antigen" is generally used in reference to any substance that is capable of reacting with an antibody. More specifically, as used herein, the term "antigen" refers to a synthetic peptide, polypeptide, protein or fragment of a polypeptide or protein, or other molecule which elicits an antibody response in a subject, or is recognized and bound by an antibody.

As used herein, the term "biomarker" refers to a molecule that is associated either quantitatively or qualitatively with a biological change. Examples of biomarkers include polypeptides, proteins or fragments of a polypeptide or protein; and polynucleotides, such as a gene product, RNA or RNA fragment; and other body metabolites. In certain embodiments, a "biomarker" means a compound that is differentially present (i.e., increased or decreased) in a biological sample from a subject or a group of subjects having a first phenotype (e.g., having a disease or condition) as compared to a biological sample from a subject or group of subjects having a second phenotype (e.g., not having the disease or condition or having a less severe version of the disease or condition). A biomarker may be differentially present at any level, but is generally present at a level that is decreased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, or by 100% (i.e., absent); or that is increased by at least 5%, by at least 10%, by at least 15%, by at least 20%, by at least 25%, by at least 30%, by at least 35%, by at least 40%, by at least 45%, by at least 50%, by at least 55%, by at least 60%, by at least 65%, by at least 70%, by at least 75%, by at least 80%, by at least 85%, by at least 90%, by at least 95%, by at least 100%, by at least 110%, by at least 120%, by at least 130%, by at least 140%, by at least 150%, or more. Alternatively, the differential presence of a biomarker can be characterize by a-fold change in level including, for example, a level that is decreased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold; or that is increased by 1.1-fold, at least 1.2-fold, at least 1.3-fold, at least 1.4-fold, at least 1.5-fold, at least 2.0-fold, at least 2.5-fold, at least 3.0-fold, at least 3.5-fold, at least 4.0-fold, at least 5-fold, at least 5.5-fold, at least 6-fold, at least 6.5-fold, at least 7.0-fold, at least 7.5-fold, at least 8.0-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, at least 20-fold, at least 25-fold, at least 30-fold, at least 40-fold, or at least 50-fold. A biomarker is preferably differentially present at a level that is statistically significant (e.g., a p-value less than 0.05 and/or a q-value of less than 0.10 as determined using, for example, either Welch's T-test or Wilcoxon's rank-sum Test).

The term "one or more of" refers to combinations of various biomarker proteins. The term encompasses 1, 2, 3, 4, 5, 6, 7, 8, 9, 10, 11, 12, 13, 15, 16, 17, 18, 19, 20, 21, 22, 23, 24, 25, 26, 27, 28, 29, 30, 31, 32, 33, 34, 35, 36, 37, 38, 39, 40 . . . N, where "N" is the total number of biomarker proteins in the particular embodiment. The term also encompasses at least 1, at least 2, at least 3, at least 4, at least 5, at least 6, at least 7, at least 8, at least 9, at least 10, at least 11, at least 12, at least 13, at least 15, 16, 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40 . . . N. It is understood that the recitation of biomarkers herein includes the phrase "one or more of" the biomarkers and, in particular, includes the "at least 1, at least 2, at least 3" and so forth language in each recited embodiment of a biomarker panel.

As used herein, the terms "comparing" or "comparison" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having cognitive dysfunction, not having cognitive dysfunction, is responding to treatment for a disease of cognition, is not responding to treatment for disease of cognition (Alzheimer's and the like), is/is not likely to respond to a particular treatment for a disease of cognition, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, standard cognitive function/dysfunction levels/ratios, etc.).

In another embodiment, the terms "comparing" or "comparison" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient's cognitive function is improving, not improving, etc. In specific embodiments, the parameter may comprise the level of one or more biomarkers of the present invention. A particular set or pattern of the amounts of one or more biomarkers may indicate that a patient has improved or worsened cognitive function (i.e., correlates to a patient having improved or worsened cognitive function).

In other embodiments, a particular set or pattern of the amounts of one or more biomarkers may be correlated to a patient being unaffected (i.e., indicates a patient does not have cognitive dysfunction). In certain embodiments, "indicating," or "correlating," as used according to the present invention, may be by any linear or non-linear method of quantifying the relationship between levels/ratios of biomarkers to a standard, control or comparative value for the assessment of the diagnosis, prediction of cognitive dysfunction or progression thereof, assessment of efficacy of clinical treatment, identification of a patient that may respond to a particular treatment regime or pharmaceutical agent, monitoring of the progress of treatment, and in the context of a screening assay, for the identification of an therapeutic for a disease of cognition.

The terms "patient," "individual," or "subject" are used interchangeably herein, and refer to a mammal, particularly, a human. The patient may have a mild, intermediate or severe disease or condition. The patient may be an individual in need of treatment or in need of diagnosis based on particular symptoms or family history. In some cases, the terms may refer to treatment in experimental animals, in veterinary application, and in the development of animal models for disease, including, but not limited to, rodents including mice, rats, and hamsters; and primates.

The terms "measuring" and "determining" are used interchangeably throughout, and refer to methods which include obtaining or providing a patient sample and/or detecting the level of a biomarker(s) in a sample. In one embodiment, the terms refer to obtaining or providing a patient sample and detecting the level of one or more biomarkers in the sample. In another embodiment, the terms "measuring" and "determining" mean detecting the level of one or more biomarkers in a patient sample. The term "measuring" is also used interchangeably throughout with the term "detecting." In certain embodiments, the term is also used interchangeably with the term "quantitating."

The terms "sample," "patient sample," "biological sample," and the like, encompass a variety of sample types obtained from a patient, individual, or subject and can be used in a diagnostic or monitoring assay. The patient sample may be obtained from a healthy subject, a diseased patient or a patient having associated symptoms of a disease of cognition like Alzheimer's. Moreover, a sample obtained from a patient can be divided and only a portion may be used for diagnosis. Further, the sample, or a portion thereof, can be stored under conditions to maintain sample for later analysis. The definition specifically encompasses cerebrospinal fluid and other liquid samples of biological origin (including, but not limited to, blood, peripheral blood, serum, plasma, cord blood, amniotic fluid, urine, saliva, stool and synovial fluid), solid tissue samples such as a biopsy specimen or tissue cultures or cells derived therefrom and the progeny thereof. In certain embodiments, a sample comprises cerebrospinal fluid. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

Various methodologies of the instant invention include a step that involves comparing a value, level, feature, characteristic, property, etc. to a "suitable control," referred to interchangeably herein as an "appropriate control," a "control sample," a "reference" or simply a "control." A "suitable control," "appropriate control," "control sample," "reference" or a "control" is any control or standard familiar to one of ordinary skill in the art useful for comparison purposes. A "reference level" of a biomarker means a level of the biomarker that is indicative of a particular disease state, phenotype, or lack thereof, as well as combinations of disease states, phenotypes, or lack thereof. A "positive" reference level of a biomarker means a level that is indicative of a particular disease state or phenotype. A "negative" reference level of a biomarker means a level that is indicative of a lack of a particular disease state or phenotype. For example, a "cognitive dysfunction-positive reference level" of a biomarker means a level of a biomarker that is indicative of cognitive dysfunction in a subject, and a "cognitive dysfunction-negative reference level" of a biomarker means a level of a biomarker that is indicative of no cognitive dysfunction of in a subject. A "reference level" of a biomarker may be an absolute or relative amount or concentration of the biomarker, a presence or absence of the biomarker, a range of amount or concentration of the biomarker, a minimum and/or maximum amount or concentration of the biomarker, a mean amount or concentration of the biomarker, and/or a median amount or concentration of the biomarker; and, in addition, "reference levels" of combinations of biomarkers may also be ratios of absolute or relative amounts or concentrations of two or more biomarkers with respect to each other. Appropriate positive and negative reference levels of biomarkers for a particular disease state, phenotype, or lack thereof may be determined by measuring levels of desired biomarkers in one or more appropriate subjects, and such reference levels may be tailored to specific populations of subjects (e.g., a reference level may be age-matched so that comparisons may be made between biomarker levels in samples from subjects of a certain age and reference levels for a particular disease state, phenotype, or lack thereof in a certain age group). Such reference levels may also be tailored to specific techniques that are used to measure levels of biomarkers in biological samples (e.g., ELISA, PCR, LC-MS, GC-MS, etc.), where the levels of biomarkers may differ based on the specific technique that is used.

In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) (e.g., no cognitive dysfunction) or a normal control individual (NC) (both terms are used interchangeably herein). For example, a "suitable control" or "appropriate control" can be a value, level, feature, characteristic, property, ratio, etc. determined prior to performing a therapy (e.g., Alzheimer's treatment) on a patient or a value, level, feature, characteristic, property, ratio, etc. determined prior to disease development (e.g., a baseline test). In yet another embodiment, a protein level/ratio, transcription rate, mRNA level, translation rate, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the present invention that correlates to cognitive dysfuncion, to which a patient sample can be compared. The patient sample can also be compared to a negative control, i.e., a profile that correlates to not having cognitive dysfunction.

As used herein, the term "predetermined threshold value of expression" of a biomarker refers to the level of expression of the same biomarker (expressed, for example, in ng/ml) in a corresponding control/normal sample or group of control/normal samples obtained from normal, or healthy, subjects, i.e., subject who do not have cognitive dysfunction. Further, the term "altered level of expression" of a biomarker in a sample refers to a level that is either below or above the predetermined threshold value of expression for the same biomarker and thus encompasses either high (increased) or low (decreased) expression levels. In particular embodiments, the biomarkers described herein a decreased relative to age-matched controls.

The terms "specifically binds to," "specific for," and related grammatical variants refer to that binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

As used herein, the terms "binding agent specific for" or "binding agent that specifically binds" refers to an agent that binds to a biomarker and does not significantly bind to unrelated compounds. Examples of binding agents that can be effectively employed in the disclosed methods include, but are not limited to, proteins and antibodies, such as monoclonal or polyclonal antibodies, or antigen-binding fragments thereof. In certain embodiments, a binding agent binds a biomarker (e.g., a polypeptide biomarker) with an affinity constant of, for example, greater than or equal to about $1 \times 10^{-6}$ M.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, gamma-carboxyglutamate, and O-phosphoserine, phosphothreonine.

An "amino acid analog" refers to a compound that has the same basic chemical structure as a naturally occurring amino acid, i.e., a carbon that is bound to a hydrogen, a carboxyl group, an amino group, and an R group (e.g., homoserine, norleucine, methionine sulfoxide, methionine methyl sulfonium), but that contains some alteration not found in a naturally occurring amino acid (e.g., a modified side chain). Amino acids and analogs are well known in the art. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The term "amino acid mimetic" refers to chemical compounds that have a structure that is different from the general chemical structure of an amino acid, but that function in a manner similar to a naturally occurring amino acid. Amino acid analogs may have modified R groups (for example, norleucine) or modified peptide backbones, but retain the same basic chemical structure as a naturally occurring amino acid. In certain embodiments, an amino acid analog is a D-amino acid, a beta-amino acid, or an N-methyl amino acid.

By "antibody" is meant any immunoglobulin polypeptide, or fragment thereof, having immunogen binding ability. As used herein, the terms "antibody fragments", "fragment", or "fragment thereof" refer to a portion of an intact antibody. Examples of antibody fragments include, but are not limited to, linear antibodies; single-chain antibody molecules; Fc or Fc' peptides, Fab and Fab fragments, and multi-specific antibodies formed from antibody fragments. In most embodiments, the terms also refer to fragments that bind an antigen of a target molecule (e.g., NPTX1 or NPTX2) and can be referred to as "antigen-binding fragments." As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies that specifically binds the target antigen.

The term "conjugate" refers to a complex of two molecules linked together, for example, linked together by a covalent bond. In one embodiment, an antibody is linked to an effector molecule; for example, an antibody that specifically binds to NPTX1 or NPTX2 covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

The terms "conjugating," "joining," "bonding," "labeling" or "linking" refer to making two molecules into one contiguous molecule; for example, linking two polypeptides into one contiguous polypeptide, or covalently attaching an effector molecule or detectable marker radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Conservative variants: "Conservative" amino acid substitutions are those substitutions that do not substantially decrease the binding affinity of an antibody for an antigen (for example, the binding affinity of an antibody for NPTX1 or NPTX2). For example, a human antibody that specifically binds NPTX1 or NPTX2 can include at most about 1, at most about 2, at most about 5, at most about 10, or at most about 15 conservative substitutions and specifically bind the NPTX1 or NPTX2 polypeptide, respectively. The term conservative variation also includes the use of a substituted amino acid in place of an unsubstituted parent amino acid, provided that antibody retains binding affinity for NPTX1 or NPTX2. Non-conservative substitutions are those that reduce an activity or binding to NPTX1 or NPTX2.

Conservative amino acid substitution tables providing functionally similar amino acids are well known to one of ordinary skill in the art. The following six groups are examples of amino acids that are considered to be conservative substitutions for one another:

) Alanine (A), Serine (S), Threonine (T);
) Aspartic acid (D), Glutamic acid (E);
) Asparagine (N), Glutamine (Q);
) Arginine (I), Lysine ( );
) Isoleucine (I), Leucine (L), Methionine (M), Valine (V); and
) Phenylalanine (F), Tyrosine (Y), Tryptophan (W).

An "effector molecule" means a molecule intended to have or produce a desired effect; for example, a desired effect on a cell to which the effector molecule is targeted. Effector molecules include such molecules as polypeptides, radioisotopes and small molecules. Non-limiting examples of effector molecules include toxins, chemotherapeutic agents and anti-angiogenic agents. The skilled artisan will understand that some effector molecules may have or produce more than one desired effect. In one example, an effector molecule is the portion of a chimeric molecule, for example a chimeric molecule that includes a disclosed antibody or fragment thereof, that is intended to have a desired effect on a cell to which the chimeric molecule is targeted.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation. An antigenic determinant can compete with the intact antigen (i.e., the "immunogen" used to elicit the immune response) for binding to an antibody.

By "an effective amount" is meant the amount of a required to ameliorate the symptoms of a disease relative to an untreated patient. The effective amount of active compound(s) used to practice the present invention for therapeutic treatment of a vascular disease varies depending upon the manner of administration, the age, body weight, and general health of the subject. Ultimately, the attending physician or veterinarian will decide the appropriate amount and dosage regimen. Such amount is referred to as an "effective" amount.

An "expression vector" is a nucleic acid construct, generated recombinantly or synthetically, bearing a series of specified nucleic acid elements that enable transcription of a particular gene in a host cell. Typically, gene expression is placed under the control of certain regulatory elements, including constitutive or inducible promoters, tissue-preferred regulatory elements, and enhancers.

By "fragment" is meant a portion (e.g., at least about 5, 10, 25, 50, 100, 125, 150, 200, 250, 300, 350, 400, or 500 amino acids or nucleic acids) of a protein or nucleic acid molecule that is substantially identical to a reference protein or nucleic acid and retains at least one biological activity of the reference. In some embodiments the portion retains at least 50%, 75%, or 80%, or more preferably 90%, 95%, or even 99% of the biological activity of the reference protein or nucleic acid described herein.

A "host cell" is any prokaryotic or eukaryotic cell that contains either a cloning vector or an expression vector. This term also includes those prokaryotic or eukaryotic cells that have been genetically engineered to contain the cloned gene(s) in the chromosome or genome of the host cell.

As used herein, "humanized" forms of non-human (e.g., murine) antibodies are chimeric antibodies that contain minimal sequence, or no sequence, derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are generally made to further refine antibody performance. In general, the humanized antibody will comprise substantially all of at least one, and typically two, variable domains, in which all or substantially all of the hypervariable loops correspond to those of a nonhuman immunoglobulin and all or substantially all of the FR residues are those of a human immunoglobulin sequence. The humanized antibody can also comprise at least a portion of an immunoglobulin constant region (Fc), typically that of a human immunoglobulin. Examples of methods used to generate humanized antibodies are described in U.S. Pat. No. 5,225,539.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

"Hybrid antibodies" are immunoglobulin molecules in which pairs of heavy and light chains from antibodies with different antigenic determinant regions are assembled together so that two different epitopes or two different antigens can be recognized and bound by the resulting tetramer.

The terms "isolated," "purified," or "biologically pure" refer to material that is free to varying degrees from components which normally accompany it as found in its native state. Various levels of purity may be applied as needed according to this invention in the different methodologies set forth herein; the customary purity standards known in the art may be used if no standard is otherwise specified. Indeed, the term "purified" does not require the material to be present in a form exhibiting absolute purity, exclusive of the presence of other compounds. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. A isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

The term "mimetic" means an agent having a structure that is different from the general chemical structure of a reference agent, but that has at least one biological function of the reference.

The term "nucleic acid" refers to an oligomer or polymer of ribonucleic acid or deoxyribonucleic acid, or analog thereof. This term includes oligomers consisting of naturally occurring bases, sugars, and intersugar (backbone) linkages as well as oligomers having non-naturally occurring portions which function similarly. Such modified or substituted oligonucleotides are often preferred over native forms because of properties such as, for example, enhanced stability in the presence of nucleases.

Specific examples of some nucleic acids envisioned for this invention may contain phosphorothioates, phosphotriesters, methyl phosphonates, short chain alkyl or cycloalkyl intersugar linkages or short chain heteroatomic or heterocyclic intersugar linkages. Also preferred are oligonucleotides having morpholino backbone structures (Summerton, J. E. and Weller, D. D., U.S. Pat. No. 5,034,506). In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone (P. E. Nielsen et al. Science 199: 254, 1997). Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$, where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form. Some specific examples of such modified bases include 2-(amino) adenine, 2-(methylamino)adenine, 2-(imidazolylalkyl)adenine, 2-(aminoalkylamino)adenine, or other heterosubstituted alkyladenines.

The term "operably linked" means that a first polynucleotide is positioned adjacent to a second polynucleotide that directs transcription of the first polynucleotide when appropriate molecules (e.g., transcriptional activator proteins) are bound to the second polynucleotide.

By "recombinant" is meant the product of genetic engineering or chemical synthesis. By "positioned for expression" is meant that the polynucleotide of the present invention (e.g., a DNA molecule) is positioned adjacent to a DNA sequence that directs transcription and translation of the sequence (i.e., facilitates the production of, for example, a recombinant protein of the present invention, or an RNA molecule).

By "substantially identical" is meant a protein or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and most preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between e.sup.-3 and e.sup.-100 indicating a closely related sequence.

By "transformed cell" is meant a cell into which (or into an ancestor of which) has been introduced, by means of recombinant DNA techniques, a polynucleotide molecule encoding (as used herein) a protein of the present invention.

II. Detection of Alzheimer's Biomarkers

A. Detection by Immunoassay

In specific embodiments, the biomarkers of the present invention can be detected and/or measured by immunoassay. Immunoassay requires biospecific capture reagents/binding agent, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

In certain embodiments, the expression levels of the biomarkers employed herein are quantified by immunoassay, such as enzyme-linked immunoassay (ELISA) technology. In specific embodiments, the levels of expression of the biomarkers are determined by contacting the biological sample with antibodies, or antigen binding fragments thereof, that selectively bind to the biomarkers; and detecting binding of the antibodies, or antigen binding fragments thereof, to the biomarkers. In certain embodiments, the binding agents employed in the disclosed methods and compositions are labeled with a detectable moiety.

For example, the level of a biomarker in a sample can be assayed by contacting the biological sample with an antibody, or antigen binding fragment thereof, that selectively binds to the target biomarker (referred to as a capture molecule or antibody or a binding agent), and detecting the binding of the antibody, or antigen-binding fragment thereof, to the biomarker. The detection can be performed using a second antibody to bind to the capture antibody complexed with its target biomarker. A target biomarker can be an entire protein, or a variant or modified form thereof. Kits for the detection of biomarkers as described herein can include pre-coated strip plates, biotinylated secondary antibody, standards, controls, buffers, streptavidin-horse radish peroxidise (HRP), tetramethyl benzidine (TMB), stop reagents, and detailed instructions for carrying out the tests including performing standards.

The present disclosure also provides methods for predicting or diagnosing Alzheimer's in a subject, etc. wherein the levels of expression of the biomarkers in a biological sample are determined simultaneously. For example, in one embodiment, methods are provided that comprise: (a) contacting a biological sample obtained from the subject with a plurality of binding agents that selectively bind to a plurality of biomarkers disclosed herein for a period of time sufficient to form binding agent-biomarker complexes; (b) detecting binding of the binding agents to the plurality of biomarkers, thereby determining the levels of expression of the biomarkers in the biological sample; and (c) comparing the levels of expression of the plurality of biomarkers in the biological sample with predetermined threshold values, wherein levels of expression of at least one of the plurality of polypeptide biomarkers above or below the predetermined threshold values indicates, for example, Alzheimer's in the subject. Examples of binding agents that can be effectively employed in such methods include, but are not limited to, antibodies or antigen-binding fragments thereof, aptamers, lectins and the like.

In a further aspect, the present disclosure provides compositions that can be employed in the disclosed methods. In certain embodiments, such compositions comprise a solid substrate and a plurality of binding agents immobilized on the substrate, wherein each of the binding agents is immobilized at a different, indexable, location on the substrate and the binding agents selectively bind to a plurality of biomarkers disclosed herein. In a specific embodiment, the locations are pre-determined. In one embodiment, the binding agents selectively bind to a plurality of biomarkers comprising NPTX1 and NPTX2. In other embodiments, such compositions additionally comprise binding agents that selectively bind to other biomarkers of cognitive dysfunction. Binding agents that can be employed in such compositions include, but are not limited to, antibodies, or antigen-binding fragments thereof, aptamers, lectins and the like.

In a related aspect, methods for assessing cognitive function/dysfunction in a subject are provided, such methods comprising: (a) contacting a biological sample obtained from the subject with a composition disclosed herein for a period of time sufficient to form binding agent-polypeptide biomarker complexes; (b) detecting binding of the plurality of binding agents to the plurality of polypeptide biomarkers, thereby determining the levels of expression of the plurality of polypeptide biomarkers in the biological sample; and (c) comparing the levels of expression of the plurality of polypeptide biomarkers in the biological sample with pre-determined threshold values, wherein levels of expression of at least one of the plurality of polypeptide biomarkers above or below the predetermined threshold values indicates cognitive function/dysfunction in the subject.

In yet another aspect, the present disclosure provides compositions comprising a solid substrate and a plurality of polypeptide biomarkers disclosed herein immobilized on the substrate, wherein each of the polypeptide biomarkers is immobilized at a different, indexable, location on the substrate. In certain embodiments, the plurality of polypeptide biomarkers includes NPTX1 and NPTX2.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds a biomarker and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

In specific embodiments, the assay performed on the biological sample can comprise contacting the biological sample with one or more capture agents (e.g., antibodies, peptides, aptamer, etc., combinations thereof) to form a biomarker:capture agent complex. The complexes can then be detected and/or quantified. A subject can then be identified as having Alzheimer's based on a comparison of the detected/quantified/measured levels of biomarkers to one or more reference controls as described herein.

In one method, a first, or capture, binding agent, such as an antibody that specifically binds the biomarker of interest, is immobilized on a suitable solid phase substrate or carrier. The test biological sample is then contacted with the capture antibody and incubated for a desired period of time. After washing to remove unbound material, a second, detection, antibody that binds to a different, non-overlapping, epitope on the biomarker (or to the bound capture antibody) is then used to detect binding of the polypeptide biomarker to the capture antibody. The detection antibody is preferably conjugated, either directly or indirectly, to a detectable moiety. Examples of detectable moieties that can be employed in such methods include, but are not limited to, cheminescent and luminescent agents; fluorophores such as fluorescein, rhodamine and eosin; radioisotopes; colorimetric agents; and enzyme-substrate labels, such as biotin.

In another embodiment, the assay is a competitive binding assay, wherein labeled biomarker is used in place of the labeled detection antibody, and the labeled biomarker and any unlabeled biomarker present in the test sample compete for binding to the capture antibody. The amount of biomarker bound to the capture antibody can be determined based on the proportion of labeled biomarker detected.

Solid phase substrates, or carriers, that can be effectively employed in such assays are well known to those of skill in the art and include, for example, 96 well microtiter plates, glass, paper, and microporous membranes constructed, for example, of nitrocellulose, nylon, polyvinylidene difluoride, polyester, cellulose acetate, mixed cellulose esters and polycarbonate. Suitable microporous membranes include, for example, those described in US Patent Application Publication no. US2010/0093557A1. Methods for the automation of immunoassays are well known in the art and include, for example, those described in U.S. Pat. Nos. 5,885,530, 4,981,785, 6,159,750 and 5,358,691.

The presence of several different polypeptide biomarkers in a test sample can be detected simultaneously using a multiplex assay, such as a multiplex ELISA. Multiplex assays offer the advantages of high throughput, a small volume of sample being required, and the ability to detect different proteins across a board dynamic range of concentrations.

In certain embodiments, such methods employ an array, wherein multiple binding agents (for example capture antibodies) specific for multiple biomarkers are immobilized on a substrate, such as a membrane, with each capture agent being positioned at a specific, pre-determined, location on the substrate. Methods for performing assays employing such arrays include those described, for example, in US Patent Application Publication nos. US2010/0093557A1 and US2010/0190656A1, the disclosures of which are hereby specifically incorporated by reference.

Multiplex arrays in several different formats based on the utilization of, for example, flow cytometry, chemiluminescence or electron-chemiluminesence technology, are well known in the art. Flow cytometric multiplex arrays, also known as bead-based multiplex arrays, include the Cytometric Bead Array (CBA) system from BD Biosciences (Bedford, Mass.) and multi-analyte profiling (xMAP.RTM.) technology from Luminex Corp. (Austin, Tex.), both of which employ bead sets which are distinguishable by flow cytometry. Each bead set is coated with a specific capture antibody. Fluorescence or streptavidin-labeled detection antibodies bind to specific capture antibody-biomarker complexes formed on the bead set. Multiple biomarkers can be recognized and measured by differences in the bead sets, with chromogenic or fluorogenic emissions being detected using flow cytometric analysis.

In an alternative format, a multiplex ELISA from Quansys Biosciences (Logan, Utah) coats multiple specific capture antibodies at multiple spots (one antibody at one spot) in the same well on a 96-well microtiter plate. Chemiluminescence technology is then used to detect multiple biomarkers at the corresponding spots on the plate.

B. Detection by Polymerase Chain Reaction

2In certain embodiments, the biomarkers of the present invention can be detected/measure/quantitated by polymerase chain reaction (PCR). In certain embodiments, the present invention contemplates quantitation of one or more biomarkers described herein including NPTX1 and NPTX2. The one or more biomarkers can be quantitated and the expression can be compared to reference levels. Overexpression or underexpression, depending on the biomarker, relative to the reference is indicative of Alzheimer's. PCR can include quantitative type PCR, such as quantitative, real-time PCR (both singleplex and multiplex). In a specific embodiment, the quantitation steps are carried using quantitative, real-time PCR. One of ordinary skill in the art can design primers that specifically bind and amplify one or more biomarkers described herein using the publicly available sequences thereof.

In more particular embodiments, an assay performed on a biological sample obtained from a subject may comprise extracting nucleic acids from the biological sample. The assay can further comprise contacting nucleic acids with one or more primers that specifically bind one or more biomarker described herein to form a primer:biomarker complex. The assay can further comprise the step of amplifying the primer:biomarker complexes. The amplified complexes can then be detected/quantified to determine a level of expression of the one or more biomarkers. A subject can then be identified as having Alzheimer's based on a comparison of the measure/quantified/determined levels of one or more biomarkers described herein to one or more reference controls as described herein. The subject can then be treated appropriately, based on the grade/extent of disease. The assay can be performed on mRNA extracted from the biological sample.

C. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

D. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

E. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

III. Determination of a Patient's Alzheimer's Status

The present invention relates to the use of biomarkers to assess cognitive function/dysfunction in Alzheimer's and other diseases of cognition. It is understood that, for the sake of brevity, the term "Alzheimer's" can be used throughout the specification, but it is understood that the methods and biomarkers described herein are applicable in the context of assessing cognitive function/dysfunction in other diseases of cognition. More specifically, the biomarkers of the present invention can be used in diagnostic tests to determine, qualify, and/or assess cognitive status, for example, to assess cognitive function/dysfunction, in an individual, subject or patient. In particular embodiments, cognitive status can include determining a patient's cognitive status, for example, to assess cognitive status in an individual, subject or patient. More specifically, the biomarkers to be detected in assessing cognitive status include, but are not limited to, NPTX1 and NPTX2. Other biomarkers known in the relevant art may be used in combination with the biomarkers described herein. It is understood that the methods and compositions described herein can not only be used to assess cognitive status in Alzheimer's, but also other diseases of cognition.

B. Biomarker Panels

The biomarkers of the present invention can be used in diagnostic tests to assess, determine, and/or qualify (used interchangeably herein) cognitive status in a patient. The phrase "cognitive status" includes any distinguishable manifestation of cognitive function or dysfunction, as the case may be, including not having cognitive dysfunction. For example, cognitive status includes, without limitation, cognitive function or dysfunction in a patient, the risk of developing cognitive dysfunction, the stage or severity of cognitive dysfunction, the progress of cognitive dysfunction (e.g., progress of cognitive dysfunction over time), or the effectiveness or response to treatment of AD or other disease of cognition (e.g., clinical follow up and surveillance of cognitive function/dysfunction after treatment). Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of people who test positive that are actually positive. Negative predictive value is the percentage of people who test negative that are actually negative.

In particular embodiments, the biomarker panels of the present invention may show a statistical difference in different Alzheimer's statuses of at least $p<0.05$, $p<10^{-2}$, $p<10^{-3}$, $p<10^{-4}$ or $p<10^{-5}$. Diagnostic tests that use these biomarkers may show an ROC of at least 0.6, at least about 0.7, at least about 0.8, or at least about 0.9.

The biomarkers can be differentially present in UI (NC or non-Alzheimer's) and Alzheimer's or other diseases of cognition, and, therefore, are useful in aiding in the determination of cognitive status. In certain embodiments, the biomarkers are measured in a patient sample using the methods described herein and compared, for example, to predefined biomarker levels/ratios and correlated to cognitive status. In particular embodiments, the measurement(s) may then be compared with a relevant diagnostic amount(s), cut-off(s), or multivariate model scores that distinguish a positive cognitive status from a negative cognitive status. The diagnostic amount(s) represents a measured amount of a biomarker(s) above which or below which a patient is classified as having a particular cognitive status. For example, if the biomarker(s) is/are up-regulated compared to normal, then a measured amount(s) above the diagnostic cutoff(s) provides an assessment of cognitive status. Alternatively, if the biomarker(s) is/are down-regulated, then a measured amount(s) at or below the diagnostic cutoff(s) provides an assessment of cognitive status. As is well understood in the art, by adjusting the particular diagnostic cut-off(s) used in an assay, one can increase sensitivity or specificity of the diagnostic assay depending on the preference of the diagnostician. In particular embodiments, the particular diagnostic cut-off can be determined, for example, by measuring the amount of biomarkers in a statistically significant number of samples from patients with the different cognitive statuses, and drawing the cut-off to suit the desired levels of specificity and sensitivity.

In other embodiments, the relative or normalized amounts biomarkers to each other are useful in aiding in the determination of cognitive status. In certain embodiments, the biomarker ratios are indicative of diagnosis. In other embodiments, a biomarker ratio can be compared to another biomarker ratio in the same sample or to a set of biomarker ratios from a control or reference sample.

Furthermore, in certain embodiments, the values measured for markers of a biomarker panel are mathematically combined and the combined value is correlated to the underlying diagnostic question. Biomarker values may be combined by any appropriate state of the art mathematical method. Well-known mathematical methods for correlating a marker combination to a disease status employ methods like discriminant analysis (DA) (e.g., linear-, quadratic-, regularized-DA), Discriminant Functional Analysis (DFA), Kernel Methods (e.g., SVM), Multidimensional Scaling (MDS), Nonparametric Methods (e.g., k-Nearest-Neighbor Classifiers), PLS (Partial Least Squares), Tree-Based Methods (e.g., Logic Regression, CART, Random Forest Methods, Boosting/Bagging Methods), Generalized Linear Models (e.g., Logistic Regression), Principal Components based Methods (e.g., SIMCA), Generalized Additive Models, Fuzzy Logic based Methods, Neural Networks and Genetic Algorithms based Methods. The skilled artisan will have no problem in selecting an appropriate method to evaluate a biomarker combination of the present invention. In one embodiment, the method used in a correlating a biomarker combination of the present invention, e.g. to diagnose Alzheimer's, is selected from DA (e.g., Linear-, Quadratic-, Regularized Discriminant Analysis), DFA, Kernel Methods (e.g., SVM), MDS, Nonparametric Methods (e.g., k-Nearest-Neighbor Classifiers), PLS (Partial Least Squares), Tree-Based Methods (e.g., Logic Regression, CART, Random Forest Methods, Boosting Methods), or Generalized Linear Models (e.g., Logistic Regression), and Principal Components Analysis. Details relating to these statistical methods are found in the following references: Ruczinski et al., 12 J. OF COMPUTATIONAL AND GRAPHICAL STATISTICS 475-511 (2003); Friedman, J. H., 84 J. OF THE AMERICAN STATISTICAL ASSOCIATION 165-75 (1989); Hastie, Trevor, Tibshirani, Robert, Friedman, Jerome, The Elements of Statistical Learning, Springer Series in Statistics (2001); Breiman, L., Friedman, J. H., Olshen, R. A., Stone, C. J. Classification and regression trees, California: Wadsworth (1984); Breiman, L., 45 MACHINE LEARNING 5-32 (2001); Pepe, M. S., The Statistical Evaluation of Medical Tests for Classification and Prediction, Oxford Statistical Science Series, 28 (2003); and Duda, R. O., Hart, P. E., Stork, D. G., Pattern Classification, Wiley Interscience, 2nd Edition (2001).

C. Determining Risk of Cognitive Dysfunction

In a specific embodiment, the present invention provides methods for determining the risk of developing cognitive dysfunction in a patient. Biomarker percentages, ratios, amounts or patterns are characteristic of various risk states, e.g., high, medium or low. The risk of cognitive dysfunction is determined by measuring the relevant biomarkers and then either submitting them to a classification algorithm or comparing them with a reference amount, i.e., a predefined level or pattern of biomarkers that is associated with the particular risk level.

D. Determining Severity of Cognitive Dysfunction

In another embodiment, the present invention provides methods for determining the severity of cognitive dysfunction in a patient. Each grade or stage of cognitive dysfunction likely has a characteristic level of a biomarker or relative levels/ratios of a set of biomarkers (a pattern or ratio). The severity of cognitive dysfunction is determined by measuring the relevant biomarkers and then either submitting them to a classification algorithm or comparing them with a reference amount, i.e., a predefined level or pattern of biomarkers that is associated with the particular stage.

E. Determining Cognitive Dysfunction Prognosis

In one embodiment, the present invention provides methods for determining the course of cognitive dysfunction in a patient. Alzheimer's course refers to changes in cognitive status over time, including cognitive dysfunction progression (worsening) and cognitive dysfunction regression (improvement; cognitive resilience). Over time, the amount or relative amount (e.g., the pattern or ratio) of the biomarkers changes. For example, biomarker "X" may be increased with cognitive dysfunction, while biomarker "Y" may be decreased with cognitive dysfunction. Therefore, the trend of these biomarkers, either increased or decreased over time toward cognitive dysfunction or cognitive resilience indicates the course of the condition. Accordingly, this method involves measuring the level of one or more biomarkers in a patient at least two different time points, e.g., a first time and a second time, and comparing the change, if any. The course of cognitive dysfunction is determined based on these comparisons.

F. Patient Management

In certain embodiments of the methods of qualifying cognitive status, the methods further comprise managing patient treatment based on the status. Such management includes the actions of the physician or clinician subsequent to determining cognitive status. For example, if a physician makes a diagnosis of Alzheimer's, then a certain regime of monitoring would follow. An assessment of the course of Alzheimer's (cognitive dysfunction in the patient having Alzheimer's) using the methods of the present invention may then require a certain Alzheimer's therapy regimen. Alternatively, a diagnosis of non-Alzheimer's might be followed with further testing to determine a specific disease

G. Determining Therapeutic Efficacy of Pharmaceutical Drug

In another embodiment, the present invention provides methods for determining the therapeutic efficacy of a pharmaceutical drug. These methods are useful in performing clinical trials of the drug, as well as monitoring the progress of a patient on the drug. Therapy or clinical trials involve administering the drug in a particular regimen. The regimen may involve a single dose of the drug or multiple doses of the drug over time. The doctor or clinical researcher monitors the effect of the drug on the patient or subject over the course of administration. If the drug has a pharmacological impact on the condition, the amounts or relative amounts (e.g., the pattern, profile or ratio) of one or more of the biomarkers of the present invention may change toward a cognitive status profile. Therefore, one can follow the course of one or more biomarkers in the patient during the course of treatment. Accordingly, this method involves measuring one or more biomarkers in a patient receiving drug therapy, and correlating the biomarker levels/ratios with the cognitive status of the patient (e.g., by comparison to predefined levels/ratios of the biomarkers that correspond to different cognitive statuses). One embodiment of this method involves determining the levels/ratios of one or more biomarkers for at least two different time points during a course of drug therapy, e.g., a first time and a second time, and comparing the change in levels/ratios of the biomarkers, if any. For example, the levels/ratios of one or more biomarkers can be measured before and after drug administration or at two different time points during drug administration. The effect of therapy is determined based on these comparisons. If a treatment is effective, then the level/ratio of one or more biomarkers will trend toward normal, while if treatment is ineffective, the level/ratio of one or more biomarkers will trend toward a particular cognitive status.

H. Generation of Classification Algorithms for Qualifying Alzheimer's Status In some embodiments, data that are generated using samples such as "known samples" can then be used to "train" a classification model. A "known sample" is a sample that has been pre-classified. The data that are used to form the classification model can be referred to as a "training data set." The training data set that is used to form the classification model may comprise raw data or pre-processed data. Once trained, the classification model can recognize patterns in data generated using unknown samples. The classification model can then be used to classify the unknown samples into classes. This can be useful, for example, in predicting whether or not a particular biological sample is associated with a certain biological condition (e.g., diseased versus non-diseased).

Classification models can be formed using any suitable statistical classification or learning method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART), artificial neural networks such as back propagation networks, discriminant analyses (e.g., Bayesian classifier or Fischer analysis), logistic classifiers, and support vector classifiers (support vector machines).

Another supervised classification method is a recursive partitioning process. Recursive partitioning processes use recursive partitioning trees to classify data derived from unknown samples. Further details about recursive partitioning processes are provided in U.S. Patent Application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. Patent Application Publication No. 2002/0193950 (Gavin et al. "Method or analyzing mass spectra"), U.S. Patent Application Publication No. 2003/0004402 (Hitt et al., "Process for discriminating between biological states based on hidden patterns from biological data"), and U.S. Patent Application Publication No. 2003/0055615 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows® or Linux™ based operating system. In embodiments utilizing a mass spectrometer, the digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including R, C, C++, visual basic, etc.

The learning algorithms described above are useful both for developing classification algorithms for the biomarkers already discovered, and for finding new biomarker biomarkers. The classification algorithms, in turn, form the base for diagnostic tests by providing diagnostic values (e.g., cut-off points) for biomarkers used singly or in combination.

IV. Kits for the Detection of Biomarkers

In another aspect, the present invention provides kits for qualifying cognitive status, which kits are used to detect the biomarkers described herein. In a specific embodiment, the kit is provided as an ELISA kit comprising antibodies to the biomarkers of the present invention including, but not limited to, NPTX1 and NPTX2.

The ELISA kit may comprise a solid support, such as a chip, microtiter plate (e.g., a 96-well plate), bead, or resin having biomarker capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

In certain embodiments, a patient can be diagnosed by adding CSF from the patient to the kit and detecting the relevant biomarkers conjugated with antibodies, specifically, by a method which comprises the steps of: (i) collecting CSF from the patient; (ii) adding the CSF from patient to a diagnostic kit; and, (iii) detecting the biomarkers conjugated with antibodies. In this method, the antibodies are brought into contact with the patient's CSF. If the biomarkers are present in the sample, the antibodies will bind to the sample, or a portion thereof. In other kit and diagnostic embodiments, CSF not be collected from the patient (i.e., it is already collected). Moreover, in other embodiments, the sample may comprise a tissue sample or a clinical sample.

The kit can also comprise a washing solution or instructions for making a washing solution, in which the combination of the capture reagents and the washing solution allows capture of the biomarkers on the solid support for subsequent detection by, e.g., antibodies or mass spectrometry. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration or normalization.

V. Antibodies to NPTX1 and Antibodies to NPTX2

The present invention provides antibodies to NPTX1 and antibodies to NPTX2. An "antibody" is a polypeptide ligand including at least the complementarity determining regions (CDRs) of a light chain or heavy chain immunoglobulin variable region which specifically binds an epitope of an antigen or a fragment thereof. Antibodies include intact immunoglobulins and the variants of them well known in the art, such as Fab', F(ab)'2 fragments, single chain Fv proteins (scFv), and disulfide stabilized Fv proteins (dsFv). A scFvprotein is a fusion protein in which a light chain variable region of an antibody and a heavy chain variable region of an antibody are bound by a linker, while in dsFvs, the chains have been mutated to introduce a disulfide bond to stabilize the association of the chains. The term "antibody" also includes genetically engineered forms such as chimeric antibodies (for example, humanized murine antibodies) and heteroconjugate antibodies (such as, bispecific antibodies).

Typically, a naturally occurring immunoglobulin has heavy (H) chains and light (L) chains interconnected by disulfide bonds. There are two types of light chains, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as domains). References to "VH" or "VH" refer to the variable region of an immunoglobulin heavy chain, including that of an Fv, scFv, dsFv or Fab. References to "VL" or "VL" refer to the variable region of an immunoglobulin light chain, including that of an Fv, scFv, dsFv or Fab. In combination, the heavy and the light chain variable regions specifically bind the antigen. Light and heavy chain variable regions contain a framework region interrupted by three hypervariable regions, also called complementarity-determining regions or CDRs. The extent of the framework region and CDRs have been defined (see, for example, Kabat et al., (1991) Sequences of Proteins of Immunological Interest, 51h Edition, U.S. Department of Health and Human Services, Public Health Service, National Institutes of Health, Bethesda, Md. (NIH Publication No. 91-3242), which is hereby incorporated by reference). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The precise amino acid sequence boundaries of a given CDR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), and Al-Lazikani et al., (1997) JMB 273, 927-948 ("Chothia" numbering scheme). The CDRs of each chain are typically referred to as CDR1, CDR2, and CDR3, numbered sequentially starting from the N-terminus, and are also typically identified by the chain in which the particular CDR is located. Thus, a HCDR1 is the CDR 1 from the variable domain of the heavy chain of the antibody in which it is found, whereas a LCDR 1 is the CDR1 from the variable domain of the light chain of the antibody in which it is found. An antibody that specifically binds an antigen of interest has a specific VH region and VL region sequence, and thus specific CDR sequences. Antibodies with different specificities (due to different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

A single-chain antibody (scFv) is a genetically engineered molecule containing the VH and VL domains of one or more antibody(ies) linked by a suitable polypeptide linker as a genetically fused single chain molecule. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites. A chimeric antibody is an antibody that contains one or more regions from one antibody and one or more regions from one or more other antibodies. An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

The antibodies disclosed herein specifically bind only to a defined target (or multiple targets, in the case of a bi-specific antibody). Thus, an antibody that specifically binds to NPTX2 is an antibody that binds substantially to NPTX2, including cells or tissue expressing NPTX2, substrate to which NPTX2 is attached, or NPTX2 in a biological specimen. It is, of course, recognized that a certain degree of non-specific interaction may occur between an antibody or conjugate including an antibody (such as an antibody that specifically binds or NPTX2 or conjugate including such antibody) and a non-target. Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope.

In one embodiment, an antibody that binds NPTX1 or NPTX2 is monoclonal. Alternatively, the NPTX1 or NPTX2 antibody is a polyclonal antibody. The preparation and use of polyclonal antibodies are also known the skilled artisan. The present invention also encompasses hybrid antibodies, in which one pair of heavy and light chains is obtained from a first antibody, while the other pair of heavy and light chains is obtained from a different second antibody. Such hybrids may also be formed using humanized heavy and light chains. Such antibodies are often referred to as "chimeric" antibodies.

In general, intact antibodies are said to contain "Fc" and "Fab" regions. The Fc regions are involved in complement activation and are not involved in antigen binding. An antibody from which the Fc' region has been enzymatically cleaved, or which has been produced without the Fc' region, designated an "F(aba)$_2$" fragment, retains both of the antigen binding sites of the intact antibody. Similarly, an antibody from which the Fc region has been enzymatically cleaved, or which has been produced without the Fc region, designated an "Fab'" fragment, retains one of the antigen binding sites of the intact antibody. Fabα fragments consist of a covalently bound antibody light chain and a portion of the antibody heavy chain, denoted "Fd." The Fd fragments are the major determinants of antibody specificity (a single Fd fragment may be associated with up to ten different light chains without altering antibody specificity). Isolated Fd fragments retain the ability to specifically bind to immunogenic epitopes.

Monoclonal antibodies can be prepared using hybridoma methods, such as those described by Kohler and Milstein (1975) Nature 256:495. Using the hybridoma method, a mouse, hamster, or other appropriate host animal, is immunized as described above to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567. The polynucleotides encoding a monoclonal antibody are isolated, such as from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc., of a monoclonal antibody.

In some embodiments, of the present invention the monoclonal antibody against NPTX1 or NPTX2 is a humanized antibody. Humanized antibodies are antibodies that contain minimal sequences from non-human (e.g., murine) antibodies within the variable regions. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g., mouse, rat, rabbit, hamster, etc.) having the desired specificity, affinity, and capability (Jones et al., 1986, Nature, 321:522-525; Riechmann et al., 1988, Nature, 332:323-327; Verhoeyen et al., 1988, Science, 239: 1534-1536). The humanized antibody can be further modified by the substitution of additional residue either in the Fv framework region and/or within the replaced non-human residues to refine and optimize antibody specificity, affinity, and/or capability.

Human antibodies can be directly prepared using various techniques known in the art. Immortalized human B lymphocytes immunized in vitro or isolated from an immunized individual that produce an antibody directed against a target antigen can be generated (See, for example, Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373). Also, the human antibody can be selected from a phage library, where that phage library expresses human antibodies (Vaughan et al., 1996, Nature Biotechnology, 14:309-314; Sheets et al., 1998, PNAS, 95:6157-6162; Hoogenboom and Winter, 1991, J. Mol. Biol., 227:381; Marks et al., 1991, J. Mol. Biol., 222:581). Humanized antibodies can also be made in transgenic mice containing human immunoglobulin loci that are capable upon immunization of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

In certain embodiments of the invention, it may be desirable to use an antibody fragment, rather than an intact antibody. Various techniques are known for the production of antibody fragments. Traditionally, these fragments are derived via proteolytic digestion of intact antibodies (for example Morimoto et al., 1993, Journal of Biochemical and Biophysical Methods 24:107-117 and Brennan et al., 1985, Science, 229:81). However, these fragments are now typically produced directly by recombinant host cells as described above. Thus Fab, Fv, and scFv antibody fragments can all be expressed in and secreted from E. coli or other host cells, thus allowing the production of large amounts of these fragments. Alternatively, such antibody fragments can be isolated from the antibody phage libraries discussed above. The antibody fragment can also be linear antibodies as described in U.S. Pat. No. 5,641,870, for example, and can be monospecific or bispecific. Other techniques for the production of antibody fragments will be apparent.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1: Neuronal Pentraxin 2 Misregulation in Alzheimer's Disease: A Biomarker Linking BACE1 Activity and Cognitive Failure Alzheimer's disease (AD) amyloid Aβ plaque is detected by in vivo imaging in close spatial association with persistently increased aberrant activity. We examined mechanisms that normally prevent sustained increases of activity and report that the immediate early gene Neuronal Pentraxin 2 (NPTX2) is paradoxically down-regulated in postmortem brain and cerebrospinal fluid (CSF) of subjects with AD, and this is consistently linked to cognitive decline. NPTX2 and co-functional NPTX family members NPTX1 and NPTXR act as a dynamic extracellular scaffold for AMPA-type glutamate receptors to mediate homeostatic control of synaptic strength. Analysis here indicates that NPTXs also bind and negatively regulate β amyloid precursor protein cleavage enzyme1 (BACE1) activity by limiting the rate of BACE1 endocytosis. Disruption of this NPTX mechanism can be rationally linked to increased Aβ generation, persistence of aberrant activity, and circuit deficits that impair information storage in sporadic AD.

Introduction

Aβ peptide is generated by sequential processing of amyloid precursor protein (APP) by β APP cleavage enzyme1 (BACE1) and γ-secretase. Mutations of APP or Presenilins (PS) that enhance generation of Aβ42/40 are causal for familial Alzheimer's disease (AD) (Selkoe and Wolfe, 2007). By contrast, mutations of APP that reduce cleavage by BACE1 are protective against AD (Jonsson et al., 2012). These observations provide strong support for the amyloid hypothesis in familial AD, and suggest that sporadic or late-onset AD may be similarly linked to enhanced Aβ generation (Selkoe, 2002).

Studies of Aβ amyloid in living subjects using Pittsburgh Compound B PET (PiB-PET) detected regions of deposition that occur in association with persistently increased aberrant activity (Buckner et al., 2009; Sperling et al., 2009). These regions, which are termed the "default mode network", fail to show expected reductions of metabolic activity that normally accompany decreased cognitive processing, and lack synchrony with other brain regions. The association of amyloid with aberrant activity is also noted in asymptomatic or minimally impaired older subjects or APOE e4 at risk individuals suggesting it may represent a prodromal state for cognitive decline (Sperling et al., 2009). The spatial association of increased activity and increased Aβ plaque suggests these phenomena are linked by shared molecular mechanisms.

In normal brain, increases of activity result in increased immediate early gene (IEG) expression. Several IEGs function at excitatory synapses to mediate control of neuronal and network excitability as part of the process termed homeostatic scaling (Turrigiano, 2012). Homeostatic scaling reestablishes the firing rate of excitatory neurons in response to persistent changes of activity in a manner that preserves the ratio of relative synaptic weights, and is required to maintain network properties essential for information storage. The IEG Arc is a cytosolic protein that functions in postsynaptic neurons by associating with endosomal membranes to accelerate endocytosis of AMPA receptors and downregulate synaptic strength (Shepherd et al., 2006). The IEG Homer 1a binds the cytosolic tail of group 1 metabotropic glutamate receptors (mGluR) and activates the receptor in the absence of ligand to drive a tyrosine phosphatase dependent down-regulation of AMPARs (Hu et al., 2010). The IEG Neuronal Pentraxin 2 (NPTX2, also termed Narp) is a secreted calcium-dependent lectin that binds AMPA receptors on the cell surface (Tsui et al., 1996) (O'Brien et al., 2002; O'Brien et al., 1999). NPTX2 functions to reduce neuronal excitability by increasing the strength of excitatory synapses on GABAergic interneurons (Chang et al., 2010). Each IEG performs a non-redundant function essential for homeostatic control of neural excitability.

Studies of Arc provide precedent that homeostatic mechanisms that control neuronal excitability also regulate APP processing relevant to AD pathogenesis (Wu et al., 2011). Aβ generation is increased in response to neuronal activity in rodent models (Cirrito et al., 2005; Kamenetz et al., 2003) and in humans (Bateman et al., 2007). Activity-dependent Aβ generation is dependent on Arc, and this is mediated by Arc's ability recruit γ-secretase to recycling endosomes that traffic APP and BACE1 (Wu et al., 2011). This is consistent with the role of Rab proteins in Aβ generation (Udayar et al., 2013). Arc expression is maintained or increased in human sporadic AD brain suggesting Arc contributes to Aβ generation and synaptic weakening (Wu et al., 2011). Arc also confers activity-dependent processing of the γ-secretase substrate Notch1 (Albert et al., 2011) and presumably other substrates, consistent the coordinate regulation of multiple γ-secretase substrates in CSF of AD patients (Hata et al., 2012). Interestingly, Aβ oligomers induce Arc expression (Um et al., 2013; Wu et al., 2011), and mGluR5-dependent synaptic depression and failure (Shankar et al., 2008; Um et al., 2013). This suggests a pathological cycle as Arc increases Aβ generation and Aβ oligomers induce Arc. Though contributing to pathogenesis, these misregulated actions of Arc reduce excitatory drive and do not appear causal for increased activity in AD.

Here, we report that NPTX2 is selectively down-regulated in sporadic AD brain and CSF, and provide support for the notion that failure of the NPTX homeostatic mechanism contributes to sustained aberrant activity. Genetic models that down-regulate NPTX expression reveal prominent increases of Aβ generation and associated loss of inhibitory control of BACE1 activity. Pathological reduction of NPTX2 is linked to increases of AB40/42 in individual human brain samples. NPTX2 down-regulation is consistently linked to cognitive decline in both brain tissue and CSF. NPTX levels in CSF show similar diagnostic power as Aβ42 or phosphorylated tau but do not correlate with these markers within samples, suggesting that NPTX levels assay a distinct pathophysiology. These studies suggest that pathological down-regulation of NPTX2 with consequent failure of homeostatic mechanisms underlies cognitive decline in sporadic AD.

Materials and Methods

All the animals used were raised at Johns Hopkins Animal Facility, and all procedures involving animals were under the guidelines of JHMI Institutional Animal Care and Use Committee. Human AD and ASYMAD brain samples were obtained from the Johns Hopkins Brain Resource Center, which includes subjects from the Baltimore Longitudinal Study of Aging. Human DS brain tissue was obtained from the NICHD brain and tissue bank for developmental disorders. Human CSF samples were obtained under IRB-approved protocols from participants in the UCSD Alzheimer's Disease Research Center. Quantitation of human Aβ40, Aβ42 and mouse Aβ40 in mouse brains were performed with commercial ELISA kits (Invitrogen and Wako). plaque was assayed by IHC with anti-Aβ specific antibody (6E10) and silver staining (Wu et al., 2011). Methods for co-immunoprecipitation, Western Blotting, and in vitro binding with GST fusion proteins are described in detail in supplementary methods. NPTX1 lentivirus rescue assay was performed using a modified lentivirus vector (FUWIG) with enhanced IRES-GFP expression and multi-cloning sites. The internalization of neuronal surface BACE1 was assayed by biotinylation of cell surface proteins and immunocytochemical staining (Wu et al., 2011).

Mouse Strains. NPTX1−/−, NPTX2−/−, and NPTXR−/− mice in congenic C57BL/6J background were obtained from Mark Perrin's lab. NPTX triple knockout (TKO) mice were generated by crossing NPTX single deletion mice. APPswe/PS1ΔE9 transgenic mice (Borchelt, D. R., Ratovitski, T., van Lare, J., Lee, M. K., Gonzales, V., Jenkins, N. A., Copeland, N. G., Price, D. L., and Sisodia, S. S. (1997). Accelerated amyloid deposition in the brains of transgenic mice coexpressing mutant presenilin 1 and amyloid precursor proteins. Neuron 19, 939-945.) (here abbreviated hAPP) strain was obtained from Phillip Wong. hAPP mice with single copy of transgene were crossed with NPTX−/− to generate hAPP/NPTX+/−, which were then crossed with NPTX−/− to generate hAPP/NPTX−/−. Similarly, WT (C57BL/6J) were crossed to hAPP mice to generate hAPP/WT, which were crossed to WT to generate cohorts. For both WT and NPTX deletion mice cohorts, ~50% of progeny of the final cross were expected to carry the hAPP transgene, and this assured that mice carry a single copy of the transgene. All procedures involving animals were under the guidelines of JHMI Institutional Animal Care and Use Committee.

Human Specimens. Human brain tissue of AD and ASYMAD was obtained from the Johns Hopkins Brain Resource Center, which includes subjects from the Baltimore Longitudinal Study of Aging. Human DS brain tissue was obtained from the NICHD brain and tissue bank for developmental disorders. Brain samples were lysed in RIPA buffer at a dilution factor 1:50 for Western blot analysis. CSF samples were dissolved with SDS loading buffer, and 12 μl of CSF were loaded to SDS-PAGE and subsequent Western blot. All CSF samples were frozen at collection and assayed after 1st thaw. We noted that NPTX protein levels decreased with multiple freeze thaw cycles.

Reagents. Rabbit anti-NPTX1, anti-NPTX2 and anti-NPTXR are described previously (Xu, D., Hopf, C., Reddy, R., Cho, R. W., Guo, L., Lanahan, A., Petralia, R. S., Wenthold, R. J., O'Brien, R. J., and Worley, P. (2003). Narp and NP1 form heterocomplexes that function in developmental and activity-dependent synaptic plasticity. Neuron 39, 513-528) (Cho, R. W., Park, J. M., Wolff, S. B., Xu, D., Hopf, C., Kim, J. A., Reddy, R. C., Petralia, R. S., Perin, M. S., Linden, D. J., et al. (2008). mGluR1/5-dependent long-term depression requires the regulated ectodomain cleavage of neuronal pentraxin NPR by TACE. Neuron 57, 858-871). Mouse anti-NPTX2 monoclonal antibody was made with GST NPTX2 N-terminus (a.a.1-220) fusion protein. Antibody specificity was confirmed with the brain tissue of NPTX2−/− mice (not shown). All other antibodies are from commercial companies. Rabbit anti-BACE1 monoclonal antibody is from Cell Signaling (Cat. Number: 5606); Mouse anti-Beta Amyloid monoclonal antibody 6E10 is from COVANCE (Cat. Number: SIG-39320); Mouse anti-APP N-terminus monoclonal antibody 22C11 is from Millipore (Cat. Number: MAB348); Mouse anti-HA monoclonal antibody is from Boehringer Mannheim (Cat. number: 1583816); Mouse anti-myc monoclonal antibody is from Santa Cruz (Cat. Number: sc-40); Mouse anti-actin monoclonal antibody is from Sigma (Cat. Number: A 2066); ECLTM anti-mouse IgG HRP is from GE Healthcare (Cat. Number: NA931V); ECLTM anti-rabbit IgG HRP is from GE Healthcare (Cat. Number: NA934V); Goat anti-American Hamster IgG antibody HRP is from Thermo Scientific (PA1-32045).

EZ-Link™ Sulfo-NHS-SS-Biotin is from PIERCE (Cat. Number: 21331); ABC kit is from Vector Laboratories (Cat. Number: PK-6100); ImmunoPure Metal Enhanced DAB substrate kit is from Pierce (Cat. Number: 34065); Western blot substrate SuperSignal West Pico Luminol Enhancer Solution (Cat. Number: 1859675) and SuperSignal West Pico Stable Peroxide Solution (Cat. Number: 1859674) are from Thermo Scientific.

Plasmids and Constructs. Myc-tagged NPTX1, myc-tagged NPTX2 and myc-tagged NPTXR were described previously (Xu et al., 2003) (Cho et al., 2008). BACE1 plasmid was described previously (Cai, H., Wang, Y., McCarthy, D., Wen, H., Borchelt, D. R., Price, D. L., and Wong, P. C. (2001). BACE1 is the major beta-secretase for generation of Abeta peptides by neurons. Nature neuroscience 4, 233-234). HA-tagged BACE1 was constructed by inserting a double strand of synthetic HA sequence (5'GAGCCC-TACCCATACGATGTTCCAGATTACGCT3' (SEQ ID NO:1) and 5'CCGGCCAGCGTAATCTGGAA-CATCGTATGGGTA3') (SEQ ID NO:2) into human BACE1 cDNA between Phenylalanine at 54 and Glycine at 55. Deletion constructs were made with the ExSite PCR-Based Site-Directed Mutagenesis Kit (Stratagene). Blunt ended PCR products were re-ligated and transformed into bacteria for subsequent selection of deletion clones. Clones were screened by restrictive digestion, DNA sequencing and protein expression. NPTX1 and NPTX2 point mutants were generated by using the QuickChange Site-Directed Mutagenesis Kit (Stratagene). In each primer, the target amino acid codon was replaced with a mutated codon. Double and triple point mutations were generated using single or double mutants as the PCR template and amplifying with the primers containing the additional mutation. All constructs are confirmed by sequencing.

Aβ40 and Aβ42 Assay in Mouse Brain. Mouse brains were dissected on ice. Half brain was homogenized with homogenize buffer (PBS with complete proteinase inhibitor cocktail (Roche) and 1 mM PMSF, (pH7.4) at a tissue to buffer volume ratio of 1:10. 100 µl of lysates were mixed with 100 µl of 4× Western blot sample buffer for Western blot assay. 500 µl of lysates were centrifuged at 100,000 g for 30 min at 4° C. Supernatant was collected for PBS soluble Aβ measurement. The pellet was solubilized with 300 µl of 70% formic acid for 1 hr on ice. After 100,000 g centrifugation for 1 hr at 4° C., the supernatant was neutralized with 1 M Tris-base according to the ratio of Tris-base/sample=16/1. Aβ levels were determined with ELISA kit (human A1340 kit, Cat. Number KHB3482 and human Aβ42 kit, Cat. number KHB3441 from Invitrogen; rodent Aβ kit, Cat. Number 294-64701 from Wako).

Plaque Staining. Mouse brain (sagittal hemi forebrain) was fixed by immersion in 10% formaldehyde (Fisher Scientific) in PBS (pH7.4) and embedded in paraffin and sectioned to 5 µm thickness on slides (Wu, J., Petralia, R. S., Kurushima, H., Patel, H., Jung, M. Y., Volk, L., Chowdhury, S., Shepherd, J. D., Dehoff, M., Li, Y., et al. (2011). Arc/Arg3.1 regulates an endosomal pathway essential for activity-dependent betaamyloid generation. Cell 147, 615-628). Sections were deparaffinized and hydrated by incubating slides at 60° C. for 30 min and then transferred into Xylene. The paraffin was removed after 3 changes of Xylene at room temperature (RT) for 5 min. Then, slides were treated 3 min with sequential changes of 100%, 95%, and 70% ethanol and ddH2O for 3 times. Slides were then processed further for immunohistostaining or silver staining.

Tissue immunohistostaining: Protein antigenicity was unmasked by the treatment with 88% formic acid for 5 min. Slides were washed with ddH2O 3 times for 5 min each. The endogenous peroxidase activity was inhibited with 1.5% hydrogen peroxide in methanol for 5 min. Sections were treated with blocking solution (4% horse serum, 0.4% Triton in TBS) at RT for 1 hr and incubated with primary mouse anti-Aβ antibody at RT for overnight. Slides were washed with TBS 3 times and incubated with biotinylated goat anti-mouse IgG for 1 hr at RT. After 3 washes with TBS, tissue sections were incubated with Avidin/Biotin mixture at RT for 1 hr. Then, they were developed in 3,3'-Diaminobenzidine (DAB) at RT for 10 to 20 min to achieve optimal contrast (monitoring under microscope). Reaction was stopped with ddH2O wash. The slides were dehydrated and mounted.

Silver staining: Slides were immersed in 20% silver nitrate (AgNO3) solution at RT for 30 min and washed in ddH2O for 3 times. Then, slides were transferred to ammonium hydroxide titrated 20% silver nitrate for 20 min in dark. They were washed 5 times with ddH2O. Slides were transferred into ammonium ddH2O (3 drops of ammonium hydroxide in 250 ml of ddH2O) for 1 min, and then transferred into ammonium hydroxide titrated 20% silver nitrate solution with 2 drops of the developer (20 ml of 37% formaldehyde, 0.5 g of citric acid and 1 drop of nitric acid in 100 ml ddH2O). Slides were allowed to develop in dark with shaking until tissue turned dark with a tan to golden background. The staining solution was washed away with running tap water for 5 to 10 min. The reaction was stopped with 5% sodium thiosulfate for 5 min. Stained slides were dehydrated and mounted.

Western Blot. Cultured cells or brain tissue were lysed with a modified RIPA buffer containing 1% Triton, 0.5%

Nadeoxycholate, 0.1% SDS, 50 mM NaF, 10 mM Na4P2O7, 2 mM Na3VO4, and protease inhibitor cocktail in PBS, pH7.4. Protein extracts were separated by 4-12% SDS-PAGE, transferred to PVDF membranes, blocked with 5% non-fat milk, and then probed with primary antibodies for overnight at 4° C. After washes with TBST (TBS with 0.1% Tween-20), membranes were incubated with HRP-conjugated secondary antibodies for 1 hr at RT. Immunoreactive bands were visualized by the enhanced chemiluminescent substrate (ECL, Pierce) on X-ray film and quantified using the image software TINA.

Co-immunoprecipitation. Mouse brain was sonicated in lysis buffer containing 1% Triton, complete proteinase inhibitor cocktail in PBS, at a tissue to buffer volume ratio of 1:50. Cultured cells with exogenous protein expression were homogenized in the same lysis buffer (about 6×10$^6$ cells/ml). Lysates were centrifuged at 8000 rpm for 10 min at 4° C. Supernatant was collected and incubated with antibody for 2 hr at 4° C. with rotation. 50 μl of GammaBind Plus beads (GE Healthcare, Cat. Number 17-0886-01) was added into the lysate/antibody mixture and incubated at 4° C. for overnight with rotation. The beads were spun down at 700 rpm for 2.5 min and washed with 4° C. lysis buffer for 3 times with 5 min each with rotation, then washed with 4° C. PBS for 3 times with 5 min each. The washing buffer was removed and 60 μl of Western blot sample buffer was added. The samples were treated at 70° C. for 15 minutes prior to Western blot assay.

In vitro Binding Assay. GST-NPTX1 pentraxin domain (a.a.209-a.a.416) fusion constructs were generated by PCR amplification using primers 5'CGACCCGGA-GACAAGTTTCAGCTG 3' (SEQ ID NO:3) and 5'GCAGAATTCTTAAATTTCTCAACTCCTTC 3' (SEQ ID NO:4) on cDNA templates of wild type NPTX1 and NPTX1 mutant (EVEK) in pRK5 vector. PCR products were subcloned into pGEX-6P GST vector (GE Healthcare) at the cloning sites BamH1 and EcoR1. Clones were screened by enzyme restrictive digestion, DNA sequencing, and the protein expression of GST fusion proteins.

Wild type GST-NPTX1 (KVKK) and mutant GST-NPTX1 (EVEK) plasmids were transformed into DH5α competent cells. The transformed bacteria were spread on ampicillin agar plates and incubated at 37° C. for overnight. A single bacterial clone was inoculated to 5 ml of LB containing 50 μg/ml of ampicillin and incubated at 37° C. for overnight. 50 μl of overnight culture was inoculated into 5 ml of LB containing 50 μg/ml of ampicillin and incubated at 37° C. on shaker for about 3 hr until cells reach mid-log growth. The expression of GST fusion proteins were induced by adding IPTG to a final concentration of 1 mM, after which bacteria was cultured at 30° C. for 3 hr. Bacteria were pelleted at 5000 g for 20 min, and pellet was re-suspended in 5 ml of cell lysis buffer containing 1% Triton, complete proteinase inhibitor cocktail at 4° C., and sonicated at grad 3 for 1 min on ice. Cell lysate was centrifuged at 10,000 rpm for 10 min. 300-500 μl of Glutathione Sepharose 4B were added to the supernatant and incubated at 4° C. for 2 hr. The beads were washed with lysis buffer 5 min for 3 times and PBS 5 min for 3 times. GST fusion proteins were stored on beads on beads in PBS containing 0.1% NaN3 at 4° C. until use for in vitro binding assay. BACE1 protein used in in vitro binding assay was prepared by transfecting Human BACE1 plasmids into cultured HEK293T with FuGene 6 (Roche). 48 hr after transfection, cells were harvested in 1 ml of cell lysis buffer, sonicated and centrifuged at 10,000 rpm at 4° C. for 10 min. The GST pull down experiment was performed by adding 50 μl of GST beads containing purified GST-NPTX1 pentraxin domain fusion protein to 1 ml of BACE1 preparation, then incubating at 4° C. for 3 hr. The beads were spun down at 700 rpm for 2 min and washed with lysis buffer 5 min for 3 times and PBS 5 min for 3 times at 4° C. After removing PBS, 60 μl of Western blot sample buffer were added to washed beads. The beads were heated at 70° C. for 15 min for Western blot assay.

Lentivirus NPTX1 Rescue Assay. Construction of Lentivirus NPTX1 plasmids: Lentivirus vector FUGW was modified by inserting a multiple cloning sites and IRES-GFP (FUWIG). WT NPTX1 and NPTX1 EVEK mutant in pRK5 vector were subcloned into FUWIG at the site between EcoR1 and Xba1. The Lentiviral production plasmids contain three constructs: the FUWIG lentiviral backbone plasmid and two packaging vectors pCMV-vsvg and pCMV delta 8.9. Due to their large sizes, the FUWIG and pCMV delta 8.9 constructs were transformed into the TOP10 cells (Invitrogen) and then prepared using a standard protocol of Qiagen maxiprep columns. The re-constructed vector FUWIG and the vectors with NPTX1 inserts were verified with enzymes digestion, DNA sequencing.

Preparation of lentivirus NPTX1 and NPTX1 mutant: Lentivirus was produced in HEK293T cells. Cells were grown in 175 cm2 flasks that were pre-coated with 0.2% gelatin solution and maintained with DMEM containing 50 U/ml penicillin, 50 mg/ml streptomycin and 2 mM Glutamax. To improve transfection efficiency, 25 μM chloroquine was added to the medium of cultured HEK293T cells when 50% confluent, and transfected 4 hr later. Cells were transfected using FuGene6 (Roche) with the ratio of 1 μg plasmid DNA: 3 μl FuGene6. 10 μM of sodium butyrate was added to the medium 8 hr after transfection to improve transfection efficiency. Culture media were changed at 24 hr after transfection and collected at 48 hr after medium change (the transfection efficiency was monitored by GFP fluorescence and typically was higher than 80%). Virus particles were pelleted by centrifugation at 25,000 rpm for 2 hr at 4° C. (Beckman SW 28 rotor). Virus particles were then resuspended with Neurobasal media, aliquoted and stored at −80° C. for future use.

Aβ rescue assay: Aβ rescue assay was performed in cultured cortical neurons derived from hAPP/NPTX1−/− E18 embryos. High density (1×106/ml) cultured neurons were infected with a titer of 1:60/22400. Eight days later, culture media were completely replaced with glia cell conditioned neuronal culture medium. After 24 hr, culture media were collected for Aβ analysis (ELISA kit) and cell lysates were prepared for Western blot.

Biotinylated Endocytosis Assay. Cell surface proteins on cultured cortical neurons were biotinylated with 20 mg/ml of Biotin reagent (EZ-Link Sulfo-NHS-LC-Biotin, Pierce, Cat. Number 21335) on ice. Cultures were washed with ice-cold culture medium to remove unreacted biotin and then incubated in fresh media at 37° C. for 12 min. Biotin that remained conjugated to proteins on the neuronal cell surface was stripped by treatment with ice-cold stripping buffer containing 50 mM glutathione, 1 mM EDTA, 75 mM NaOH and 25 mM NaCl. Unreacted biotin reagent was neutralized with 20 mM glycine in TBS for 3 min. After washing, cells were sonicated in pH 4.0 lysis buffer. Biotinylated proteins were immunoprecipitated with 50 μl of Avidin beads. Total surface biotinylated protein is the amount of protein on cells labeled without subsequent incubation at 37° C. incubation or stripping. A stripping control was prepared by stripping after labeling without incubation at 37° C.

Cell Culture and Transfection. Primary neuronal cultures from embryonic day 17.5 (E17.5) mouse pups were prepared as described previously (Chang, M. C., Park, J. M., Pelkey, K. A., Grabenstatter, H. L., Xu, D., Linden, D. J., Sutula, T. P., McBain, C. J., and Worley, P. F. (2010). Narp regulates homeostatic scaling of excitatory synapses on parvalbumin-expressing interneurons. Nature neuroscience 13, 1090-1097). Cells were plated on 0.02% PLL-coated coverslip at a density of 5×104 per well of 24-well plate for immunocytochemistry. Transfection was carried out using Lipofectamine 2000 (Life Technologies) on DIV 13-15. Transfected cultures were ready for experiments 16 to 24 hours later.

Immunocytochemistry. To examine surface BACE1, cultured hippocampal neurons were transfected with HA-BACE1 on DIV13. One day later, surface HA-BACE1 was labeled with HA antibody (Santa Cruz, sc-7392) for 5 min at 37° C. Cells were fixed with 4% paraformaldehyde and 4% sucrose in PBS for 10 min at RT, blocked with 10% goat serum for 30 min at RT, and incubated with Alexa Fluor 568-conjugated secondary antibody to visualize surface HABACE1. After repeat fixation with 4% paraformaldehyde and 4% sucrose in PBS for 5 min, cells were permeablizied with 0.2% Triton X-100, blocked with goat serum, and incubated with HA primary antibody followed by Alexa Fluo 488-conjugated secondary antibody to label intracellular HA-BACE1. HA-BACE1 on cell surface was calculated as the ratio of the surface HA-BACE1 to the sum of surface and intracellular HABACE1.

To examine BACE1 internalization, hippocampal culture was transfected with BACE1 tagged with HA (HABACE1) on DIV13. One day later, surface HA-BACE1 was labeled with HA antibody and neurons were incubated for 20 min in 37° C. incubator. Cells were then fixed with 4% paraformaldehyde and 4% sucrose in PBS for 10 min at RT. After blocking with 10% goat serum for 30 min at RT, Alexa Fluor 568-conjugated secondary antibody was applied to label surface HA-BACE1 for 30 min at RT. After washing with PBS, cells were again fixed with 4% paraformaldehyde and 4% sucrose in PBS for 5 min at RT. Internalized HA-BACE1 were detected by Alexa Fluor 488-conjugated secondary antibody after permeabilizing cells with 0.2% Triton X-100 and blocking with 10% goat serum. Coverslips were mounted on glass slides with ProLong Gold antifade reagent. The internalization index was defined as the ratio of the internalized HA-BACE1 to the sum of surface and internalized HA-BACE1.

Confocal images were acquired with Z-stacks of each neuron by Zeiss LSM 510 confocal microscope at 0.5 μm intervals. For quantification of internalization and surface HA-BACE1, confocal settings for image acquisition were maintained for all cells. Image stacks were flattened into a single image by a maximum projection and analyzed with Image J. For co-localization analysis of internalized HA-BACE1 and endosomal markers, 50 μm of dendrites were randomly selected and the internalized HA-BACE1 and Rab puncta were analyzed with Image J.

RNA extraction and quantitative PCR. Total RNA was extracted by TRIzol reagent (Invitrogen) according to the manufacturer's protocol. One μg of isolated RNA was then immediately reverse-transcribed into cDNA using the SuperScript First-Strand Synthesis System for RT-PCR (Invitrogen). Quantitative PCR was performed with a StepOne Plus machine (Applied Biosystem) using SYBR green ROX qPCR mastermix in a 96-well optical plate. PCR cycling consists of 95° C. for 10 min, followed by 40 cycles of 95° C. for 30 sec, 64° C. for 30 sec and 72° C. for 30 sec. A melt curve was conducted to determine the specificity of PCR amplification.

Two pairs of primers were designed for NPTX2 which gave the same results. NPTX2 F1: 5' CGCGCAGCGCGAGGCCATCC3' (SEQ ID NO:5), NPTX2 R1: 5'TGCCTCTCCAGCTCCCCCAG3' (SEQ ID NO:6). NPTX2 F2: 5'CATCGAGCTGCTCATCAAC3' (SEQ ID NO:7), NPTX2 R2: 5'CTGCTCTTGTC-CAAGGATC3' (SEQ ID NO:8). GAPDH was served as an internal control to normalize data. GAPDH F: 5'AGAAGGCTGGGGCTCATTTG3' (SEQ ID NO:9), GAPDH R: 5'AGGGGCCATCCACAGTCTTC3' (SEQ ID NO:10).

TABLE 1

Primers

| SEQ ID NUMBER | DESCRIPTION |
|---|---|
| 11 | Human NPTX2; amino acids 48-59 is epitope used to produce monoclonal antibodies; amino acids 1-16: signal peptide |
| 12 | Rat NPTX2 |
| 13 | Mouse NPTX2 |
| 14 | Mutated NPTX2 used a standard protein to prevent aggregation. Amino acids 29, 41 and 94 mutated from cysteine to serine. |
| 15 | Human NPTX1; amino acids 95-106 is epitope used to produce monoclonal antibodies |
| 16 | Mouse NPTX1; amino acids 95-106 is epitope used to produce monoclonal antibodies |
| 17 | Epitope/synthetic peptide from human NPTX2 used to produce monoclonal antibodies |
| 18 | Epitope/synthetic peptide from human NPTX1 used to produce monoclonal antibodies |

Monoclonal antibodies recognized the following sequences: rabbit anti-NPTX2 (amino acids 105-168); mouse anti-human NPTX2 (amino acids 49-60); mouse anti-NPTX2 (amino acids 27-93) (designated 8 #); rabbit anti-NPTX1 (amino acids 105-207); and mouse anti-human NPTX1 (amino acids 93-109) (produced two different McAbs of different specificity)

Results

NPTX2 is down regulated in AD brain. We examined NPTX expression in human postmortem brain comparing cases with pathologically confirmed Alzheimer's disease (AD) versus age-matched controls. NPTX2 protein was markedly reduced in all assayed regions of AD subjects (FIGS. 1A and 1B) including precuneus (PCU, Brodmann area 7), frontal pole (FPC, Brodmann area 10), occipital gyms (OCC, Brodmann area 17), middle frontal gyms (MFG, Brodmann area 9), middle temporal gyrus (MTG, Brodmann area 21) and parietal gyrus (PAR, Brodmann area 40). NPTX2 mRNA was similarly reduced and levels correlated within samples with NPTX2 protein (FIGS. 1C and 1D).

Figure 7:
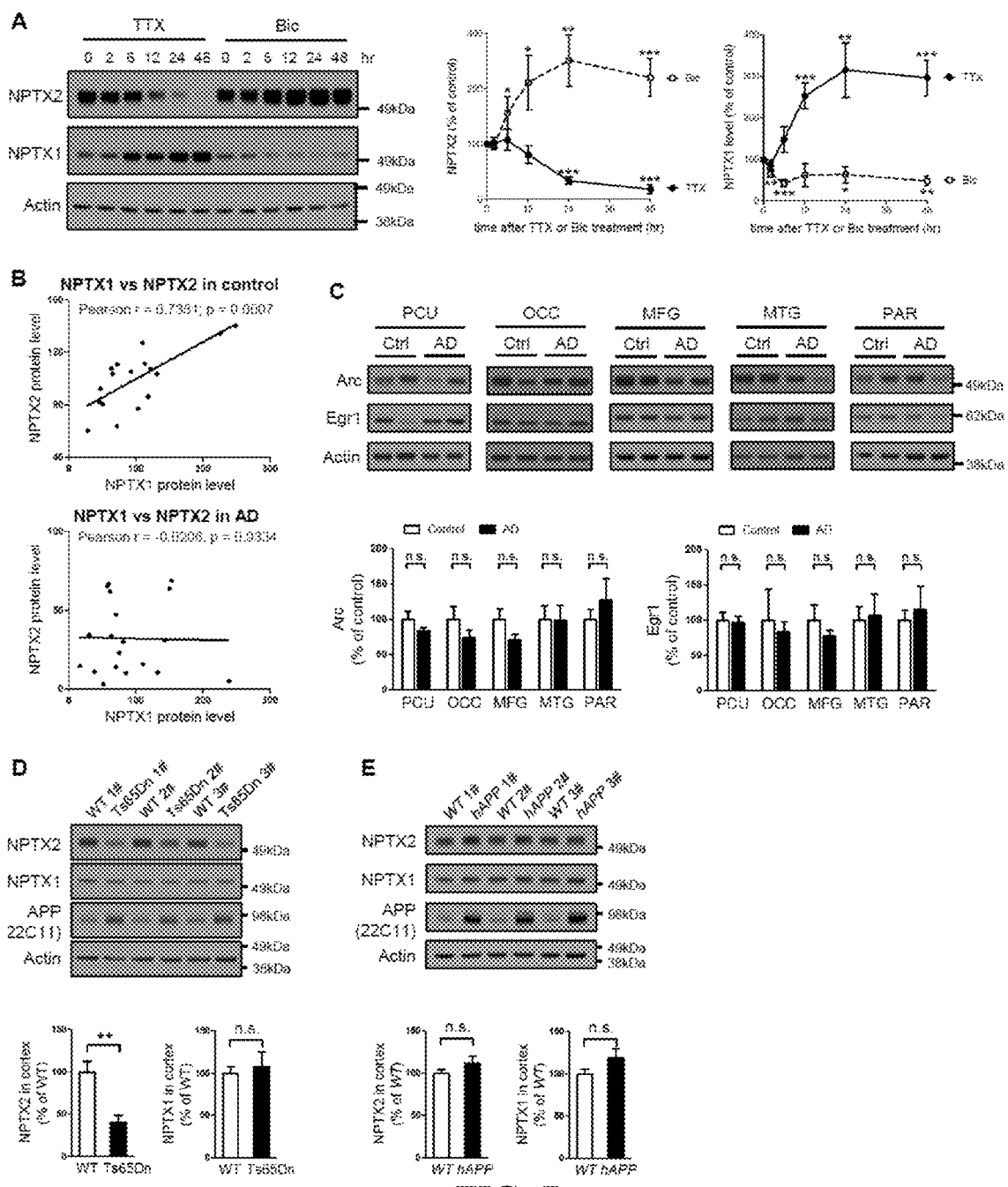
FIG. 7: Related to FIG. 1. (A) NPTX expression is regulated by activity. NPTX2 and NPTX1 expression in neuronal culture with chromic TTX (1 μM) or bicuculline (Bic, 40 μM) treatment. NPTX2 expression is induced by bicuculline, whereas NPTX1 is suppressed by bicuculline. n=4-7 samples from 4 independent culture. (B) NPTX1 and NPTX2 protein expression correlated in precuneus gyrus region within individual control subjects, but not in AD. n=17 for control and n=19 for AD. (C) Arc and Egr1 expression in different brain regions of control and AD subjects, including precuneus gyms (PCU), occipital gyrus (OCC), middle frontal gyms (MFG), middle temporal gyrus (MTG) and parietal gyms (PAR). Quantitation of Western blots show that expression of Arc and Egr1 are not significantly altered in all tested brain areas from AD individuals. PCU: n=17 for control and n=19 for AD; OCC: n=8 for control and n=10 for AD; MFG: n=7 for control and n=11 for AD; MTG: n=5 for control and n=5 for AD; PAR: n=6 for control and n=5 for AD. (D) NPTX expression in Ts65Dn mouse brains. NPTX2 protein level is reduced in 3 month-old Ts65Dn mouse cortex. n=3-5. (E) NPTX expression in hAPP mouse brains. NPTX2 and NPTX1 expression are not significantly changed in 6 month-old hAPP mouse cortex. n=6. * p<0.05,  p<0.01, * p<0.001, two-tailed t test. Data represent mean±SEM.

NPTX2 is co-functional with Neuronal Pentraxin family members Neuronal Pentraxin 1 (NPTX1; also termed NP1) (Omeis et al., 1996) and Neuronal Pentraxin receptor (NPTXR)(Dodds et al., 1997). NPTX1 protein structure is closely similar to NPTX2, but in cell biological assays NPTX1 forms smaller surface aggregates and is less synaptogenic (Xu et al., 2003). Moreover, NPTX1 protein expression shows reciprocal changes during the homeostatic response to persistent changes of activity (FIG. 7A). In the culture model, NPTX1 expression is markedly increased in response to reduced activity and modestly decreased in response to increased activity. NPTX1 and NPTX2 are co-expressed in neurons and are linked by disulfide bonds during biosynthesis (Xu et al., 2003). Thus, the normal homeostatic response to increased activity involves a prominent increase in the ratio of NPTX2 to NPTX1. NPTXR is distinct from NPTX1 and NPTX2 in that it encodes an additional N-terminal transmembrane domain, and serves as a membrane anchor for disulfide-linked macroassemblies of NPTX1, NPTX2 and NPTXR on the cell surface (Xu et al., 2003). NPTXR is cleaved by the extracellular matrix metalloprotease tumor necrosis factor-alpha converting enzyme (TACE) in a process of ectodomain shedding that is important for mGluR-LTD (Cho et al., 2008). NPTX1 (FIGS. 1A and 1E) was increased in middle temporal gyrus, but not statistically different in other brain regions. NPTXR was not different between AD and control brains (not shown). NPTX1 and NPTX2 protein expression correlated within individual control subjects, but not in AD (FIG. 7B). We were not able to separately assay surface versus total NPTX expression in tissue samples. Other IEGs including Arc and Egr-1 were not reduced (FIG. 7C), suggesting a selective deficit of NPTX2 expression. Available antibodies for Homer1a did not provide conclusive data.

NPTX2 was also reduced in middle frontal gyrus of Down syndrome (DS) cases (FIG. 1F, 1G), and modestly reduced in the mouse DS model Ts65Dn (FIG. 7D). DS individuals display several parallels with AD including increased levels of AB, plaque and an AD-like cognitive decline (Menendez, 2005). The brain samples we examined were from subjects who were younger than typical for AD in DS, suggesting that NPTX2 down-regulation may precede AD-like decline.

Figure 5:
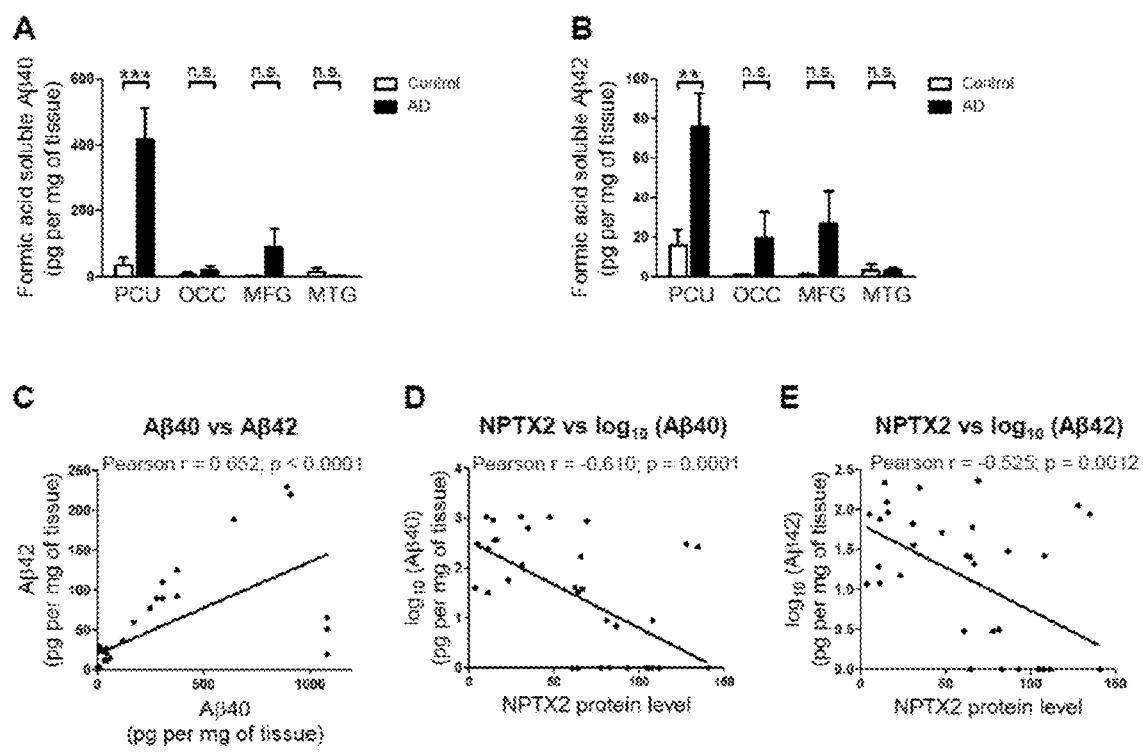
FIG. 5. Elevated Aβ in human postmortem AD brain correlates with NPTX2 downregulation. (A, B) Aβ40 (A) and Aβ42 (B) are increased in the PCU from individuals with AD.  p<0.01, * p<0.001, two-tailed t test. Data represent mean±SEM. (C-E) In the PCU region, Aβ40 and Aβ42 correlate within samples (C), and correlate with NPTX2 level inversely (D, E). PCU: precuneus gyrus, n=17 for control and n=18 for AD. OCC: occipital gyrus, n=7 for control and n=10 for AD. MFG: middle frontal gyrus, n=7 for control and n=10 for AD. MTG: middle temporal gyrus, n=4 for control and n=5 for AD.

Since Aβ is increased in both AD and DS, we asked if NPTX2 down-regulation might occur as a consequence of mechanisms that increase Aβ and plaque. NPTX2 was not reduced in middle frontal gyrus cortex of subjects with pathological criteria of AD, including Aβ plaque and tangles, but who were cognitively normal at death (Driscoll and Troncoso, 2011) (asymptomatic AD; FIGS. 1H and 1I). Moreover, NPTX2 was not reduced in 6-month-old APPswe/PS1ΔE9 transgenic mice (here abbreviated hAPP) where measured levels of hAβ40/42 exceed those in human AD brain (FIG. 7E) (compare FIGS. 8A and 8B with FIG. 5). These data suggest that NPTX2 down-regulation in human brain is not a simple consequence of increased Aβ or tau pathology.

Figure 2:
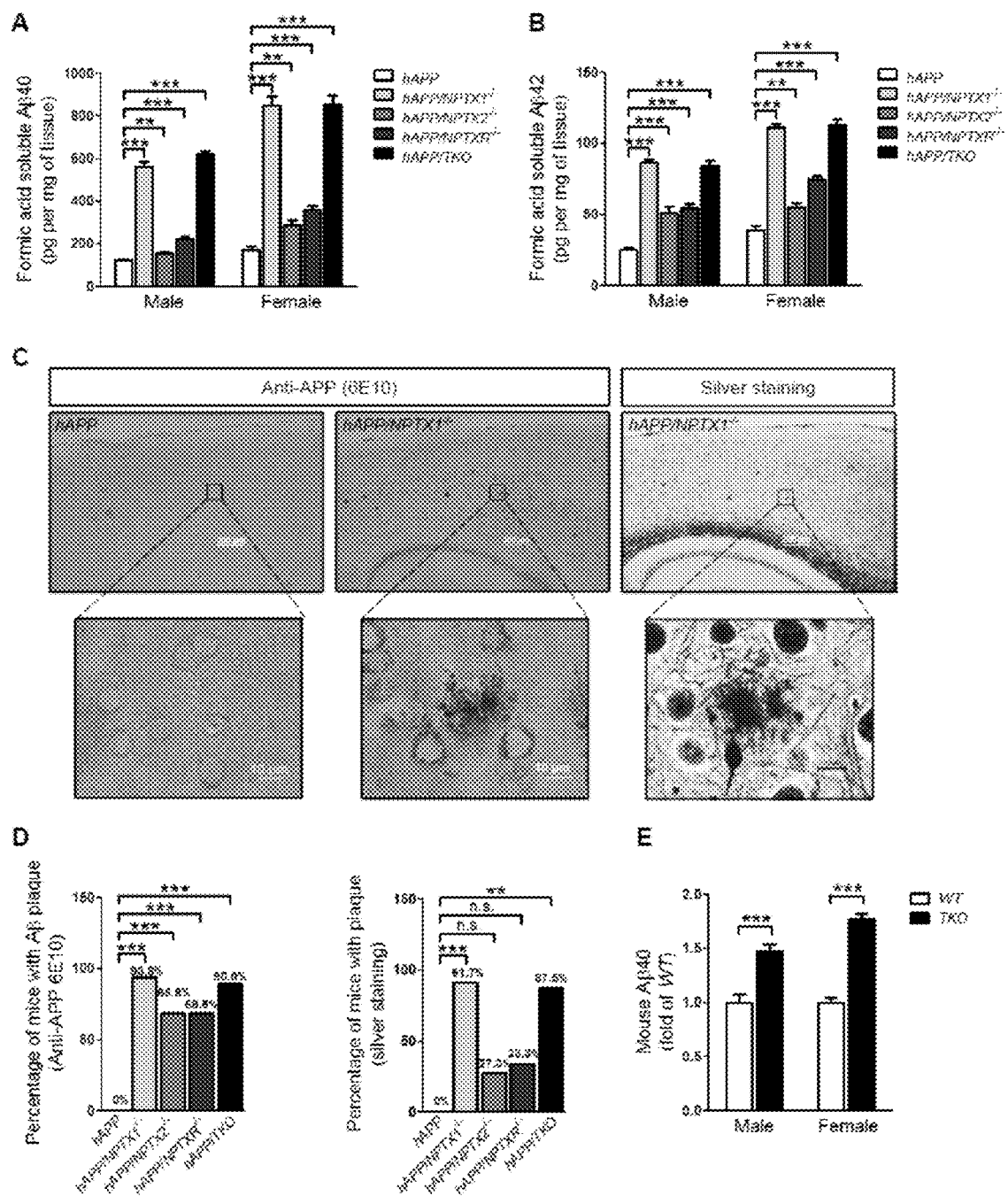
FIG. 2. Elevated Aβ and plaque in NPTX knockout mouse brain. (A, B) Aβ40 (A) and Aβ42 (B) are increased in 3 month-old hAPP/NPTX−/− mice compared with hAPP. n=8 per group.  $p<0.01$, * $p<0.001$, two-tailed t test. Data represent mean±SEM. (C, D) Specific APP antibody (6E10) staining and silver staining reveal plaque in hAPP/NPTX−/− mice at 3 months, whereas there is no Aβ plaque detected in hAPP mice at the same age. n=8-16 per group including both male and female mice.  $p<0.01$, * $p<0.001$, t-test of two percentages. (E) Rodent native Aβ40 is increased in NPTX triple KO (TKO) mice. n=6-8 per group. *** p<0.001, two-tailed t test. Data represent mean±SEM. See also FIG. 8.
Figure 8:
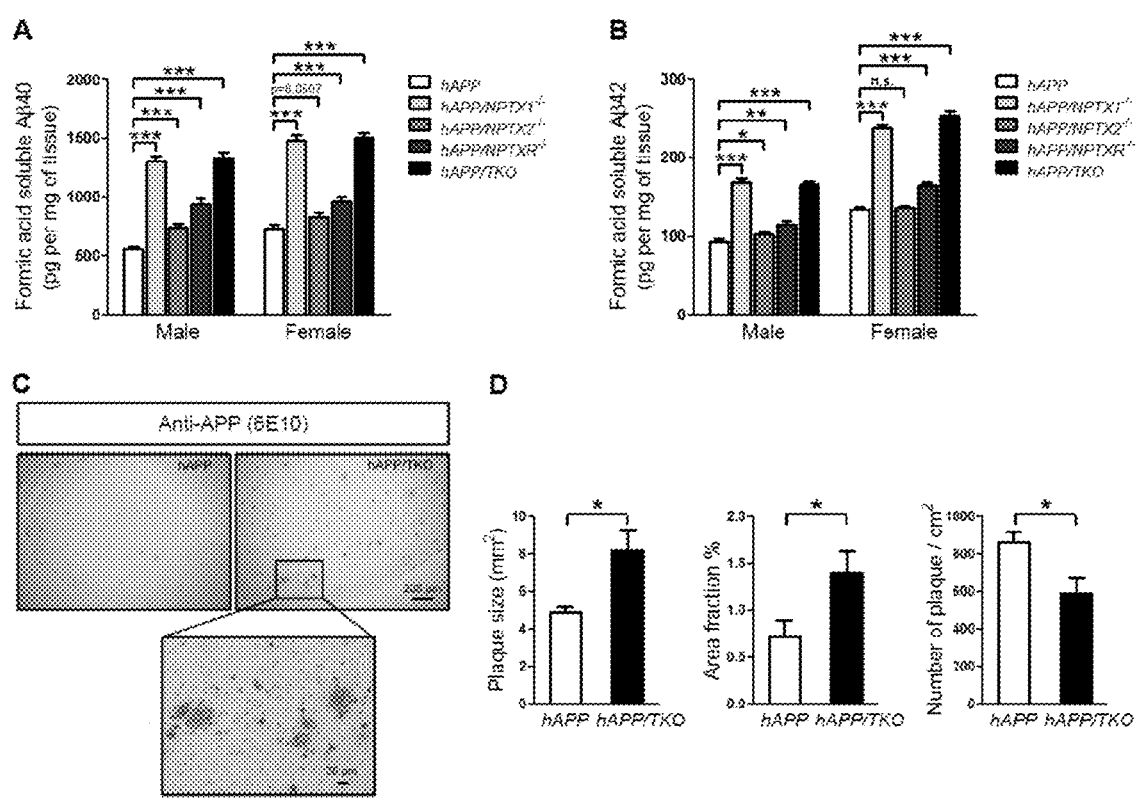
FIG. 8. Elevated Aβ levels and plaque formation in 6 month old hAPP/NPTX KO mouse brain, related to FIG. 2. (A, B) Aβ40 (A) and Aβ42 (B) are increased in 6 month-old hAPP/NPTX deletion mice. n=8 per group. (C, D) Specific APP antibody (6E10) staining reveals increased plaque formation in hAPP/TKO mice at 6 months. n=4-5 per group. * p<0.05,  p<0.01, * p<0.001, two-tailed t test. Data represent mean±SEM.

NPTX deletion increases Aβ amyloid in a mouse model of AD amyloidosis. To assess the role of NPTXs in Aβ generation, we crossed hAPP (Borchelt et al., 1997) with genetic deletion mutants of NPTXs and assayed brain at 3 months of age. Formic acid soluble Aβ40 and Aβ42 increased in all genotypes with most striking increases in hAPP/NPTX1−/− and hAPP/triple NPTX knockout (hAPP/TKO) mice (FIGS. 2A and 2B). In contrast to hAPP mice, which do not show Aβ plaque at 3 months (Borchelt et al., 1997), plaque was evident by immunostaining with 6E10 Ab in >90% of hAPP/NPTX1−/− mice, and ~70% of hAPP/NPTX2−/− mice (FIGS. 2C and 2D). Increases of Aβ were not due to increased APP or BACE1 expression (not shown). Six-month-old mice showed similar increases of Aβ expression and plaque that was most prominent in hAPP/NPTX1−/− and hAPP/TKO (FIG. 8). Mouse Aβ40 increased in NPTX TKO mice indicating that NPTX deletion affects native APP processing (FIG. 2E).

Figure 3:
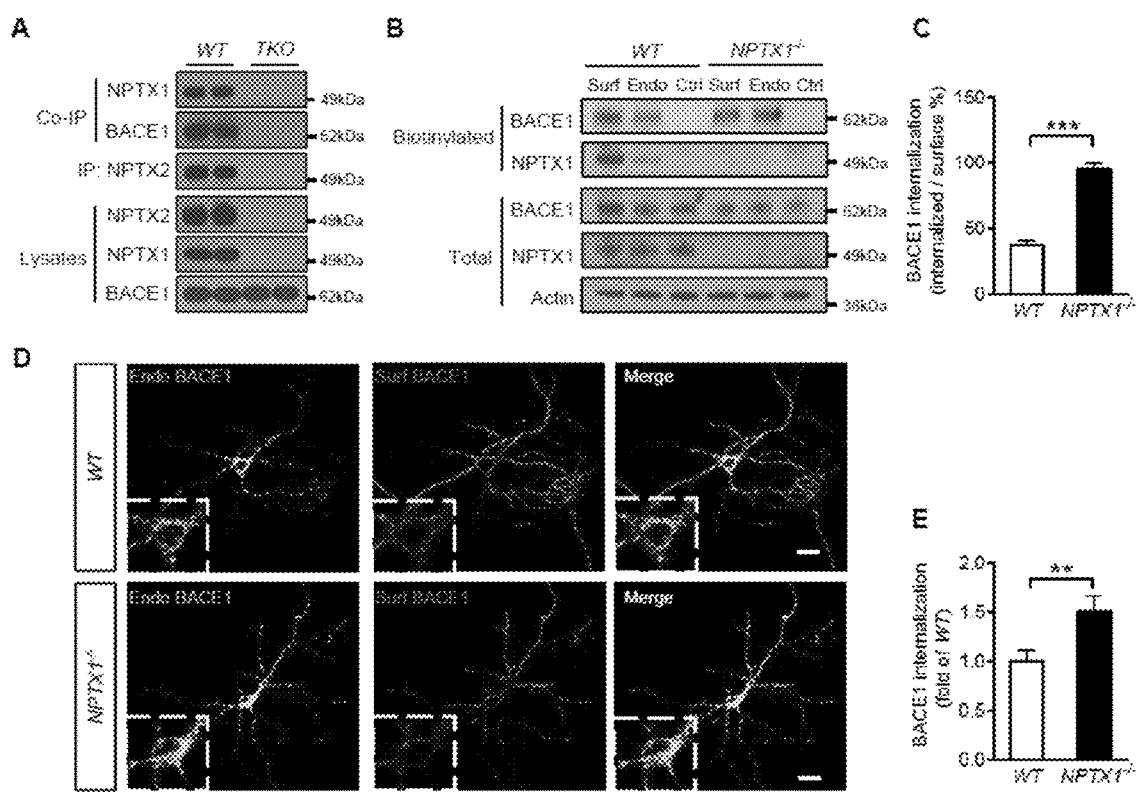
FIG. 3. BACE1 associates with NPTX and internalized more rapidly in NPTX1−/− neurons. (A) NPTX2 co-IPs NPTX1 and BACE1 from brain lysate. (B) Biotinylation assay shows cell surface (Surf) BACE1 and NPTX1 before or after 12 min incubation at 37° C. to permit endocytosis (Endo) before stripping. Control cells (Ctrl) were maintained at 4° C. before stripping. (C) Quantitative assessment of (B) reveals more BACE1 is internalized in NPTX1−/− neurons than in WT. n=4. (D) Representative immunocytochemical images showing endocytosed HA-BACE1 and remaining surface HA-BACE1 after 20 min incubation at 37° C. with HA antibody in WT and NPTX1−/− neurons. Scale bar, 20 μm. (E) Quantitative assessment of (D) shows increased HA-BACE1 endocytosis in NPTX1−/− neurons. BACE1 internalization is presented as the ratio of internalized HA-BACE1 to internalized HA-BACE1 plus remaining surface HA-BACE1. n=37-39 neurons from two independent experiments.  p<0.01, * p<0.001, two-tailed t test. Data represent mean±SEM. See also FIGS. 9 and 10
Figure 9:
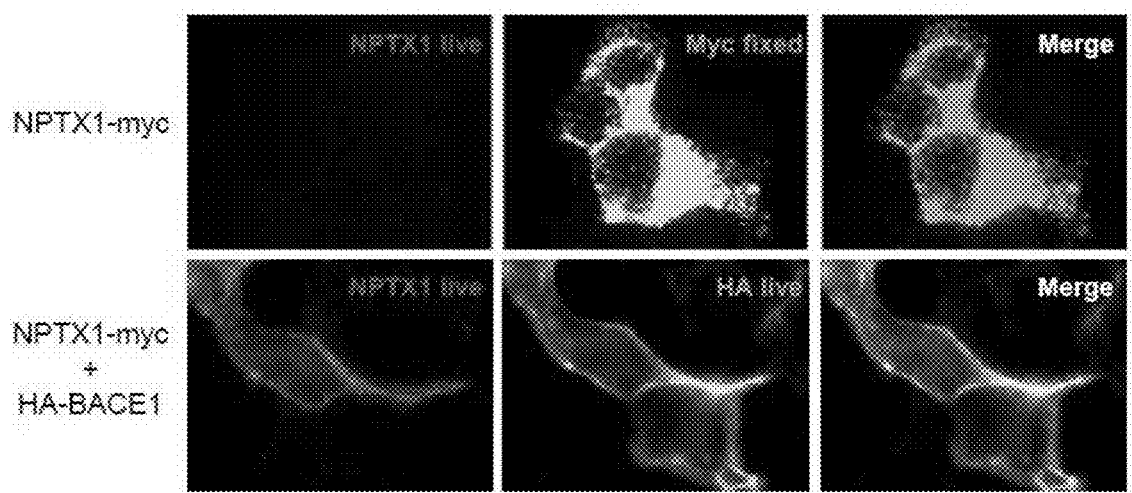
FIG. 9. NPTX1 and BACE1 co-existence on the surface of HEK293T cells, related to FIG. 3. NPTX1-myc expressed in HEK293T cells cannot be detected on cell surface by live staining. When co-expressed with HA-BACE1, NPTX1 is associated with plasma membrane and colocalized with cell surface BACE1.
Figure 10:
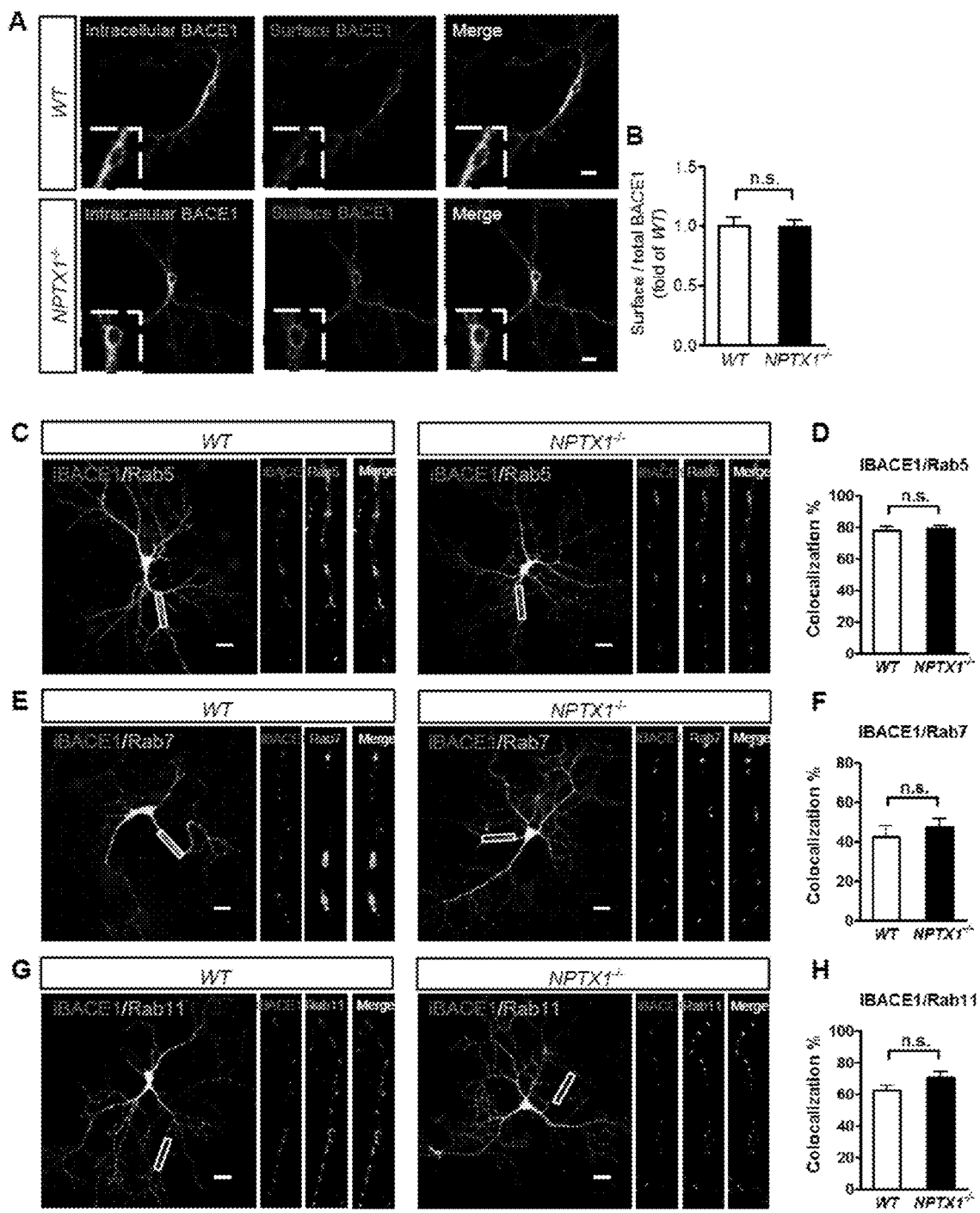
FIG. 10. Surface expression and the trafficking of HA-BACE1, related to FIG. 3. (A, B) Surface HA-BACE1 expression is not altered in NPTX1−/− neurons. (A) Representative immunocytochemical images show intracellular HA-BACE1 and surface HA-BACE1 in WT and NPTX1−/− neurons. Scale bar, 20 μm. (B) Quantitative assessment of surface HA-BACE1 normalized to the total HA-BACE1 (surface plus intracellular HABACE1). n=14-22 neurons from two independent experiments. (C-H) Internalized BACE1 co-localizes with endosomal markers. Representative immunocytochemical images and quantification of co-localization of internalized HA-BACE1 (iBACE1) with transgenes of early endosome marker Rab5 (C and D), late endosome marker Rab7 (E and F) and recycling endosome marker Rab11 (G and H) after 15 min internalization in WT and NPTX1−/− neurons. Co-localization of internalized HA-BACE1 with endosome markers is not different between genotypes. Scale bar, 20 μm. n=13-17 neurons from two independent experiments. Two-tailed t test. Data represent mean±SEM.

NPTXs bind BACE1 and limit activation. We asked how NPTX deletion might increase AB, and determined that BACE1 co-immunoprecipitates with NPTX1/2 complex from brain (FIG. 3A). When expressed in HEK293 cells without NPTXR, NPTX1 diffuses into medium (Xu et al., 2003), but when co-expressed with BACE1 the proteins coclustered on the cell surface (FIG. 9). This supports the notion that NPTX1 binds BACE1 on the membrane surface. BACE1 is normally activated during endocytosis by the acidic environment within endosomes (Vassar et al., 1999; Vassar and Kandalepas, 2011). We examined the possibility that NPTXs inhibit BACE1 activity by limiting trafficking from the plasma membrane into endosomes. This model is similar to the action of NPTX in limiting AMPA receptor endocytosis prior to ectodomain cleavage of NPTXR (Cho et al., 2008). BACE1 trafficking was assayed using a membrane impermeant biotinylating reagent (FIGS. 3B and 3C). In WT neurons, an amount of BACE1 corresponding to 37.5±2.8% of surface expression was internalized within 12 min at 37° C. By contrast, in NPTX1−/− neurons an amount of BACE1 corresponding to 95.0±4.3% of surface expression was internalized. We sought to visualize native BACE1 trafficking but could not establish a histochemical assay due to limitations of antibodies. As an alternative, we imaged an N-terminally tagged HA-BACE1 transgene by live labeling of cortical neurons. The percentage of surface labeled HA-BACE1 that was internalized after 20 min was increased in NPTX1−/− neurons (FIGS. 3D and 3E). Control experiments confirmed that steady state expression of HA-BACE1 on the neuronal surface was not different in NPTX1−/− neurons (FIGS. 10A and 10B), and internalized HA-BACE1 similarly co-localized with endosomal markers in both genotypes (FIG. 10C-10H).

Figure 4:
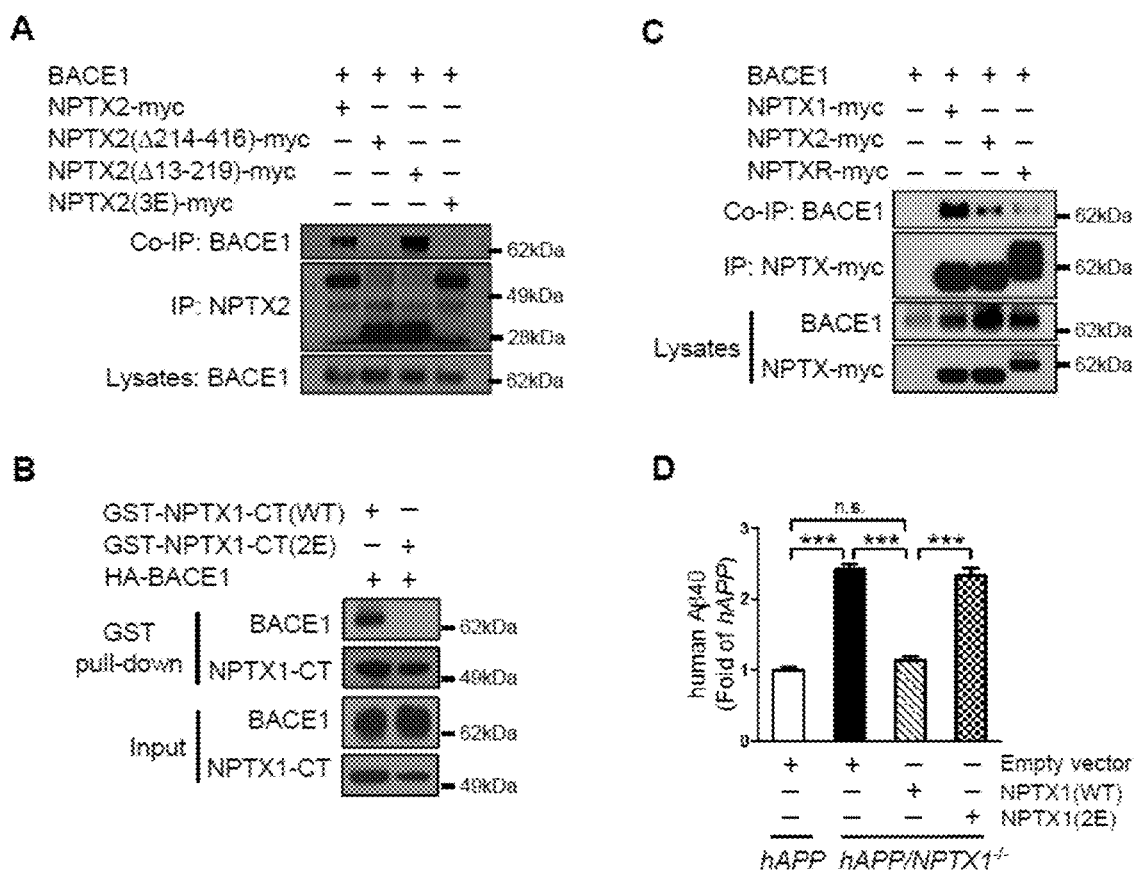
FIG. 4. NPTXs bind BACE1 to regulate Aβ generation. (A) Co-IP assay from HEK293 cells expressing truncation or point mutant NPTX2(KIKK to EIEE)(3E) of NPTX2 identifies sequence in pentraxin domain required for BACE1 binding. (B) In vitro binding assay with purified bacterial GST-NPTX1 pentraxin domain (GST-NPTX1-CT) with WT KVKK or point mutant NPTX1(KVK to EVE)(2E) sequence indicates KXK is required to bind BACE1. (C) Co-IP assay from HEK293 cells indicates that BACE1 binds NPTX1>NPTX2>NPTXR. (D) Increased Aβ40 in media of DIV15 hAPP/NPTX1−/− neurons (106 cells/well) is restored to levels in hAPP by lentivirus expression of NPTX1, not mutant NPTX1 (2E). n=12. *** p<0.001. Data represent mean±SEM.

The BACE1-NPTX2 interaction was reconstituted in HEK293 cells using co-IP assays. The N-terminus of NPTX2 includes a coiled-coil domain, which mediates self-multimerization (Xu et al., 2003), while the C-terminus encodes a pentraxin domain (Emsley et al., 1994), which binds AMPAR (Xu et al., 2003) and is structurally similar to the laminin G domain present in agrin (Stetefeld et al., 2004) and laminin (Hohenester and Engel, 2002). NPTX2 interaction with BACE1 is mediated by the C-terminal pentraxin domain (FIG. 4A). Mutation analysis of NPTX2 identified a lysine-rich loop on the surface of the pentraxin domain that is required for co-IP with BACE1 (FIG. 4A). The loop sequence is conserved but not identical among NPTXs, and is identical between mouse and human NPTX genes (data not shown). An analogous mutation in NPTX1 disrupted NPTX1-BACE1 binding (FIG. 4B). This appeared to be a selective effect of mutation since it did not disrupt other properties including surface expression (not shown) or binding to AMPAR GluA1 (data not shown). NPTXs displayed different avidities in co-IP assays with BACE1; NPTX1>NPTX2>NPTXR (FIG. 4C). A peptide mimic of NPTX1 loop reduced in vitro binding of BACE1 and NPTX2 (data not shown). To determine if NPTX binding to BACE1 is important for Aβ generation, we expressed WT and mutant NPTX1(2E) by lentivirus in cortical neurons cultured from hAPP/NPTX1−/− mice. Consistent with in vivo models, hAβ40 was increased fold in media of hAPP/NPTX1−/− neurons compared to hAPP neurons (FIG. 4D). Expression of NPTX1 reduced Aβ40 to levels present in hAPP cultures, while the NPTX1(2E) mutant did not restore Aβ levels. These observations support a model in which NPTXs bind BACE1 on the cell surface and restrict BACE1 incorporation into recycling endosomes.

NPTX2 down-regulation in brain correlates with tissue Aβ levels. To determine if Aβ expression correlates with NPTX down-regulation in human brain, we assayed formic acid soluble Aβ40/42 in the same samples assayed for NPTX expression. Levels of Aβ40/42 showed striking regional heterogeneity but were consistently elevated in the precuneus gyrus of the parietal cortex (FIGS. 5A and 5B). The precuneus gyms is notable in positron emission tomography (PET) imaging studies of AD as possessing high levels of amyloid (Buckner et al., 2005), yet shows typical histopathology of AD (Nelson et al., 2009). Within the precuneus, Aβ40 and Aβ42 levels were highly correlated with each other, indicating reliability of assays (FIG. 5C), and were inversely correlated with NPTX2 (FIGS. 5D and 5E). This is consistent with an inhibitory role for NPTX2 in BACE1 activity and Aβ generation. NPTX1 expression was not reduced in these samples, however, we could not exclude the possibility that membrane surface NPTX1 expression might be reduced and contribute to increased Aβ.

Figure 6:
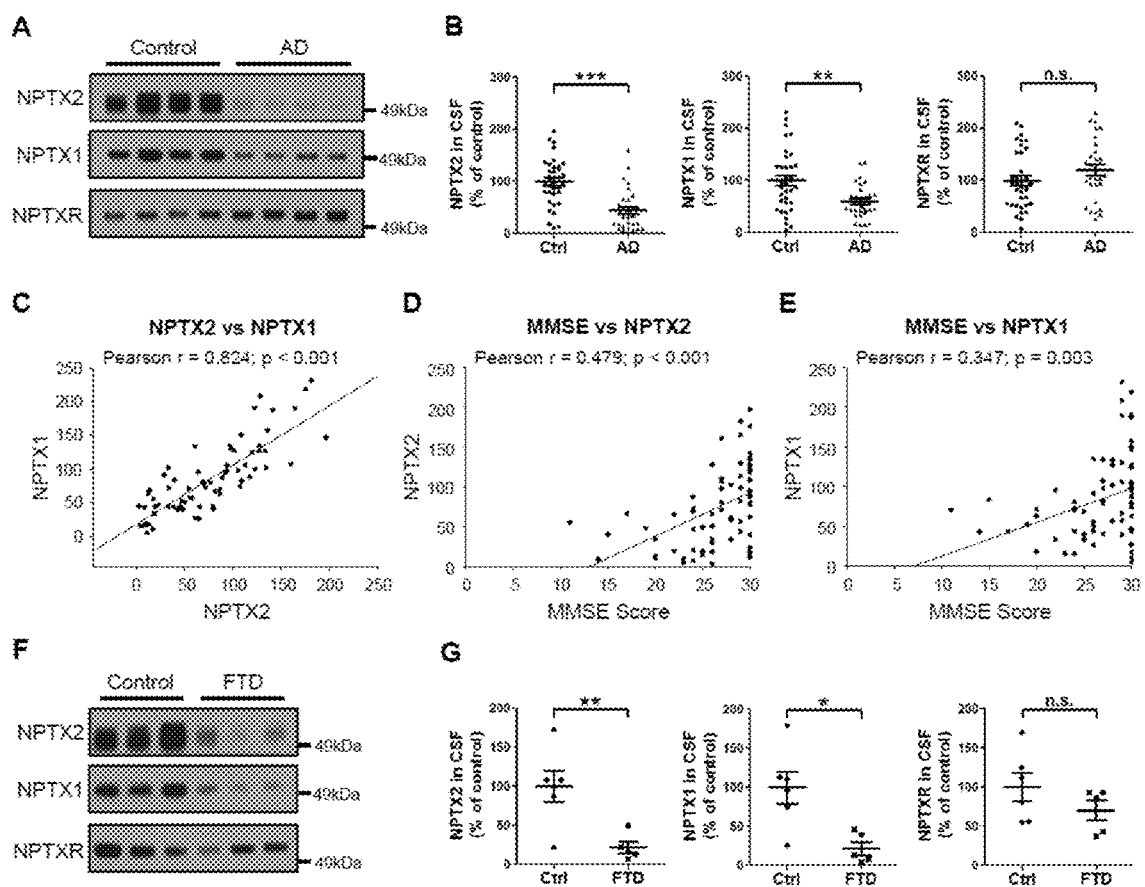
FIG. 6. NPTX levels are reduced in CSF from individuals with clinical diagnosed AD. (A, B) Representative western blot images and quantification of NPTX2, NPTX1 and NPTXR in CSF from patients with clinical AD. AD patients show reduced NPTX2 and NPTX1 levels in CSF compared with healthy controls. (C-E) NPTX2 and NPTX1 expression in CSF correlate within samples, and with cognitive function assessed by the Mini Mental Status Exam (MMSE). n=36 for control, n=30 for AD, n=6 for MCI. (F, G) Representative western blot images and quantification of NPTX1, NPTX2 and NPTXR in CSF from patients with clinical frontotemporal dementia (FTD). NPTX2 and NPTX1 are reduced in CSF of FTD patients. n=6 for control, n=5 for FTD. * p<0.05,  p<0.01, * p<0.001, two-tailed t test. Data represent mean±SEM. See also FIG. 11 and Tables 1-2.
Figure 11:
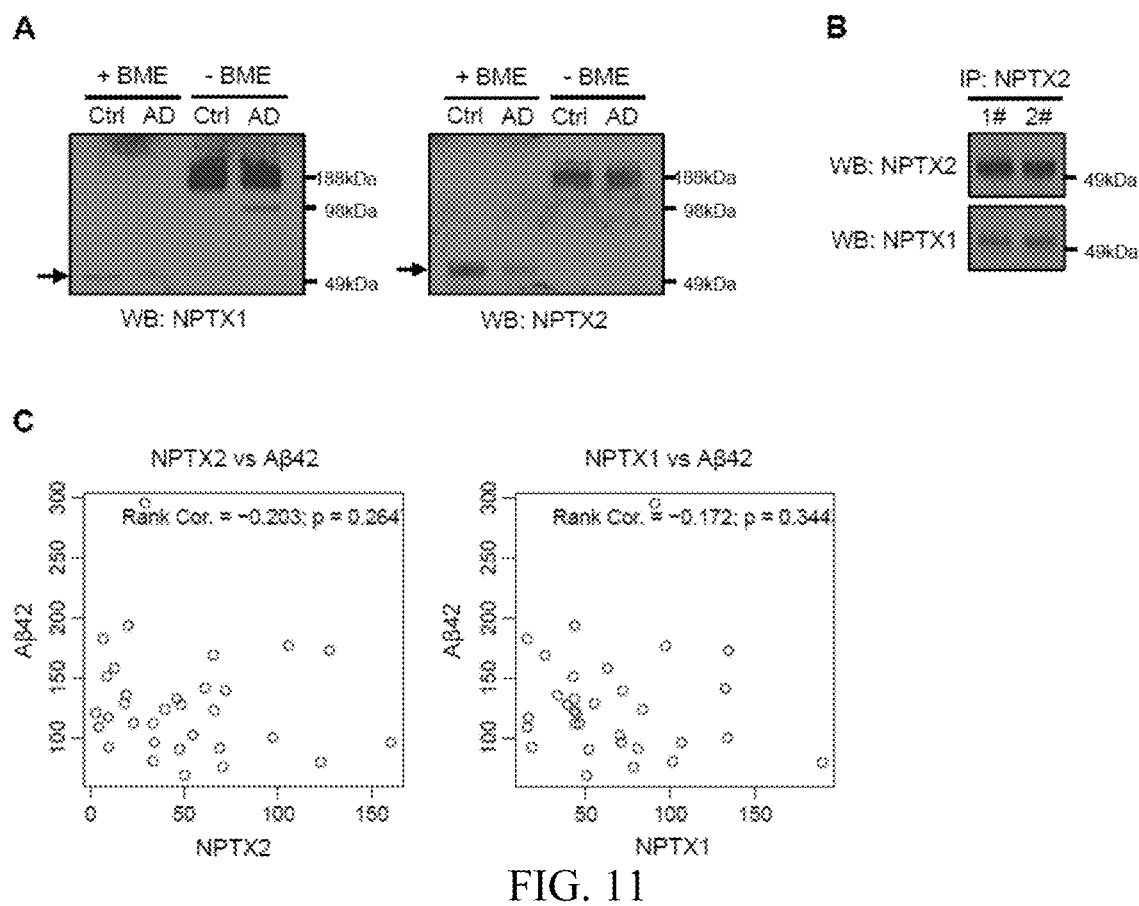
FIG. 11. Related to FIG. 6. (A) NPTX1 and NPTX2 are detected in lumbar CSF of human subjects as a high molecular weight complex that is resolved into individual NPTXs with reducing agent on SDS-PAGE. Arrows indicate monomer NPTX1 and NPTX2. (B) NPTX1 is co-IPed with NPTX2 from CSF of two subjects. (C) No correlation is observed between NPTX and Aβ42 in CSF from patients with AD and MCI, related to FIG. 6. n=26 for AD, and n=6 for MCI.
Figure 12C:
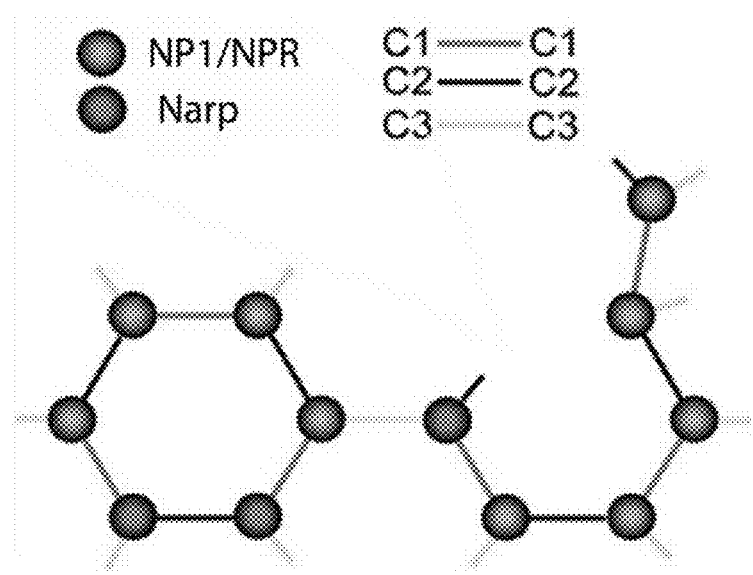
FIG. 12. A: Structure model of NPTX1, NPTX2 and NPTXR. N terminal of NPTXs (Coil-coil domain) is involved in multimer assembly via disulfide bonds. C terminal is ligand binding domain. B: The relationship of cysteines in disulfide bond formation. Three cysteines (C1, C2 & C3) are involved in intra-disulfide bond formation. The role is C1-C1, C2-C2, and C3-C3. Nomenclature of C1,C2 & C3 is based on the order of sequence from N terminal. C: Model of heterocomplex assambly. NPTXs can form huge heterocomplexes via N terminal cysteines, which restrict the quantitatively measurement of NPTXs with any ligand binding assay.
Figure 13A:
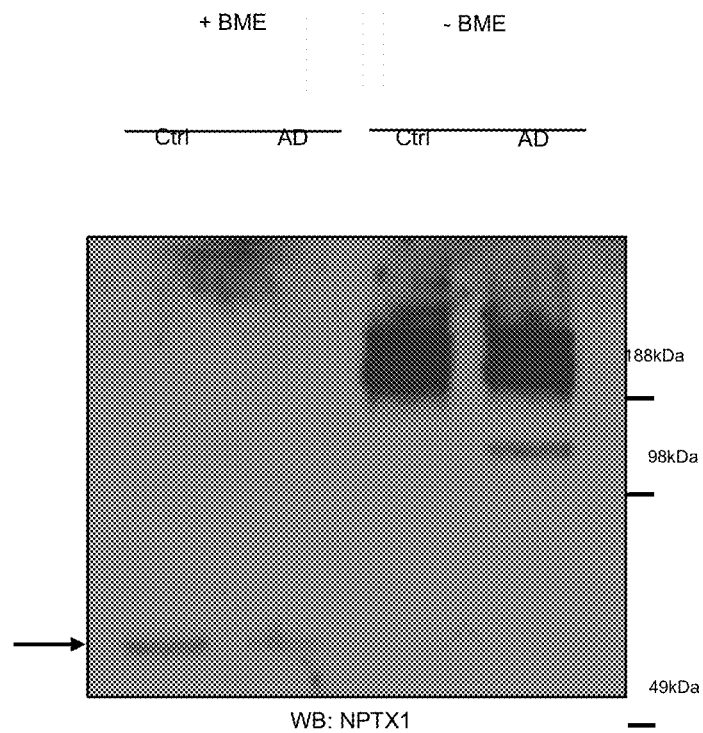
FIG. 13. NPTX2 and NPTX1 form heterocomplexes. A and B: Both NPTX2 and NPTX1 exist as complexes in CSF. NPTX2 & NPTX1 run at higher molecular size (multimers) at absence of reducing reagent than predicted based on the gene size. The size reduced to monomer by reducing reagent, (WE. C and D: NPTX2 and NPTX1 form heterocomplexes in CSF. NPTX2 and NPTX1 can be co-iped each other from reduced and non-reduced condition from CSF, which indicates they are exist as heterocomplexes.
Figure 13B:
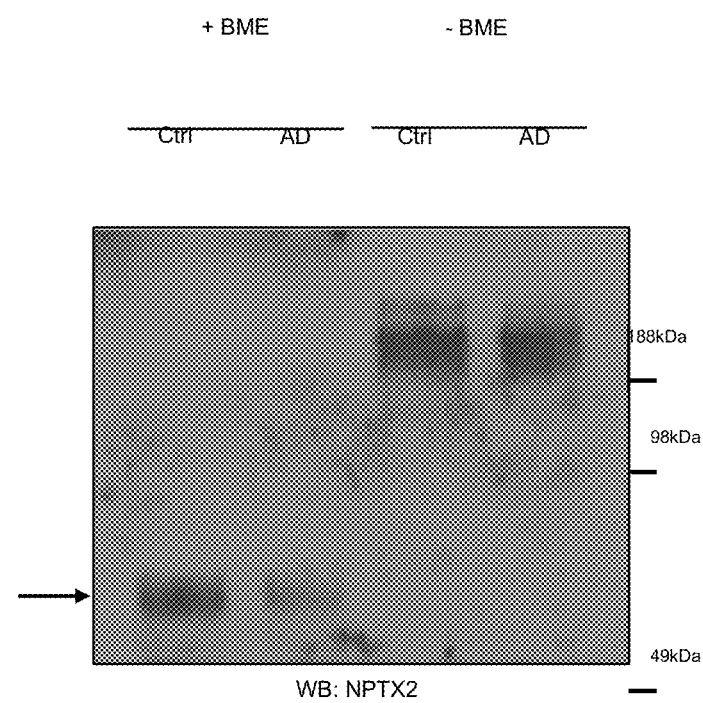
Figure 13C:
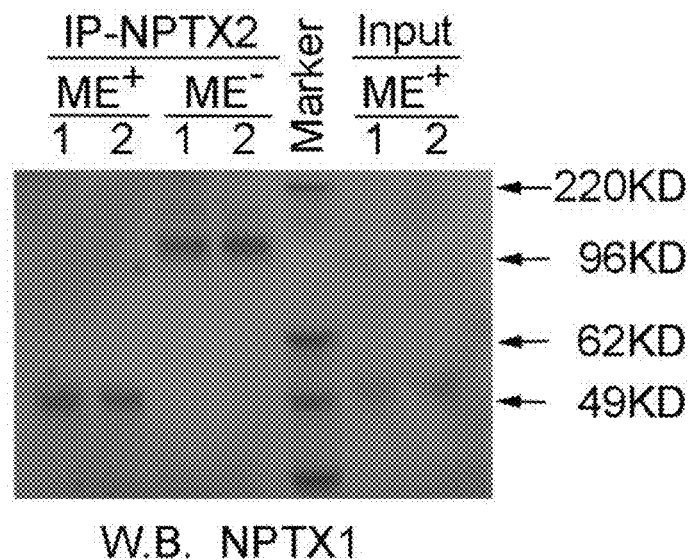
Figure 13D:
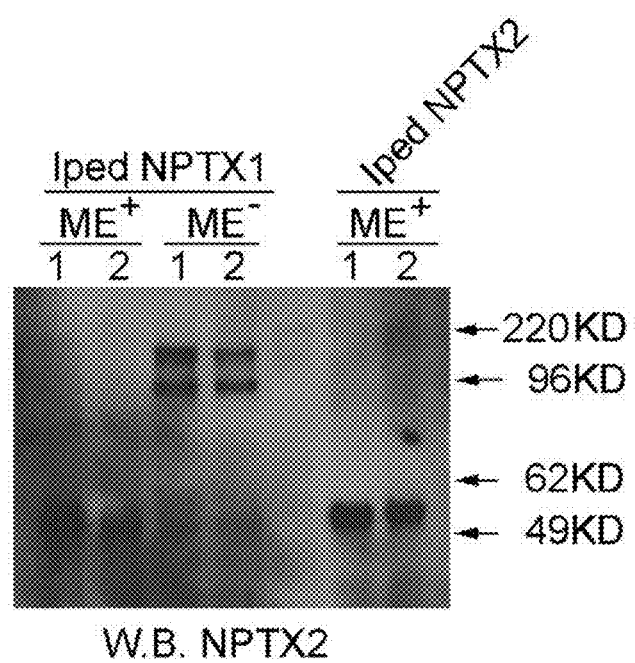
Figure 14:
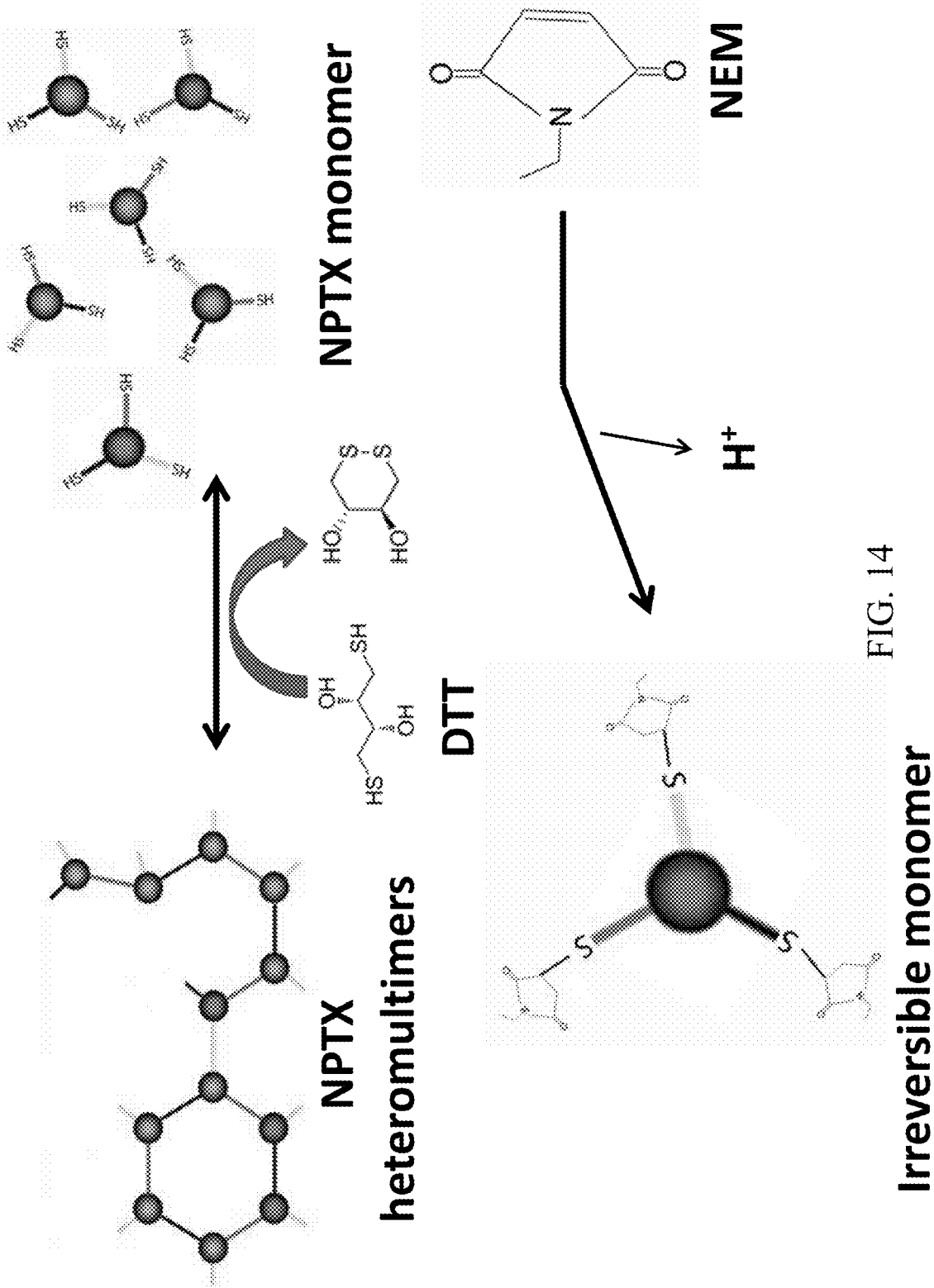
FIG. 14. NPTX2 in CSF reduced to monomer with Dithiothreitol (DTT) and exist as stable status after covalently modified with N-Ethylmaleimide (NEM) irreversible blocker.
Figure 15A:
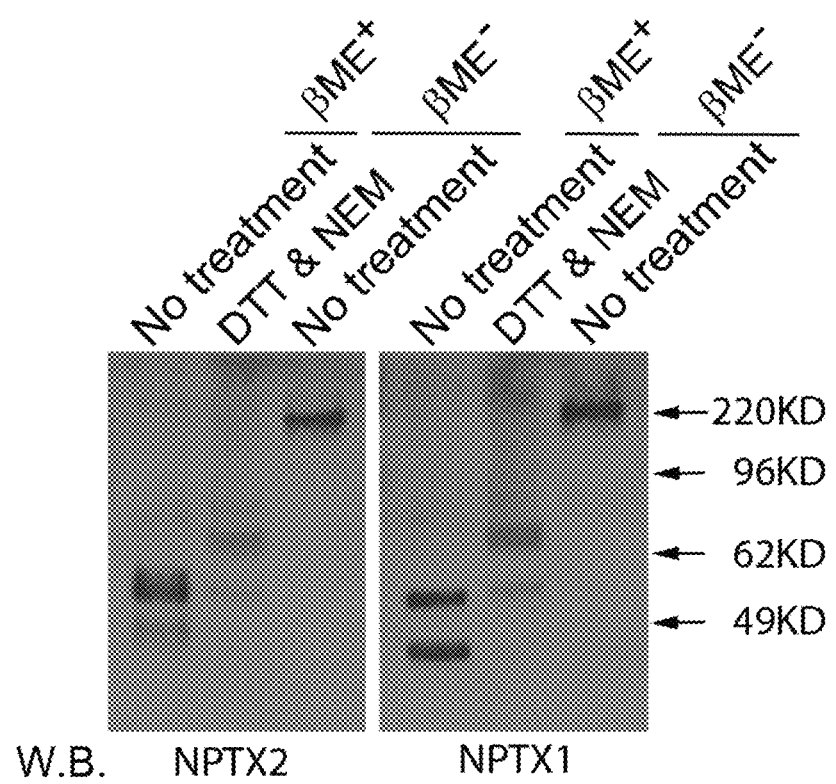
FIG. 15. Conversion of CSF NPTXs Multimers to Monomer with DTT/NEM treatment. A: ELISA result show significant difference between DTT/NEM treat & non-treat. After treatment with DTT/NEM, the ELISA reading is much higher than non-treat. B: ELISA reading of DTT/NEM treat shows a smaller variation than non-treat.
Figure 15B:
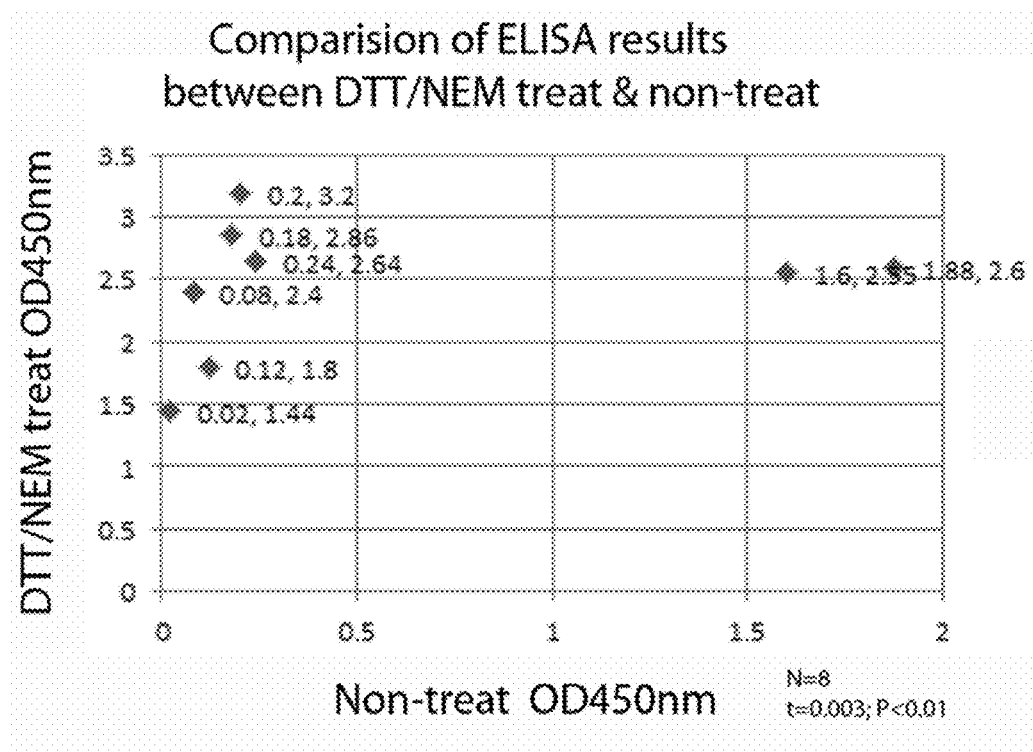
Figure 16A:
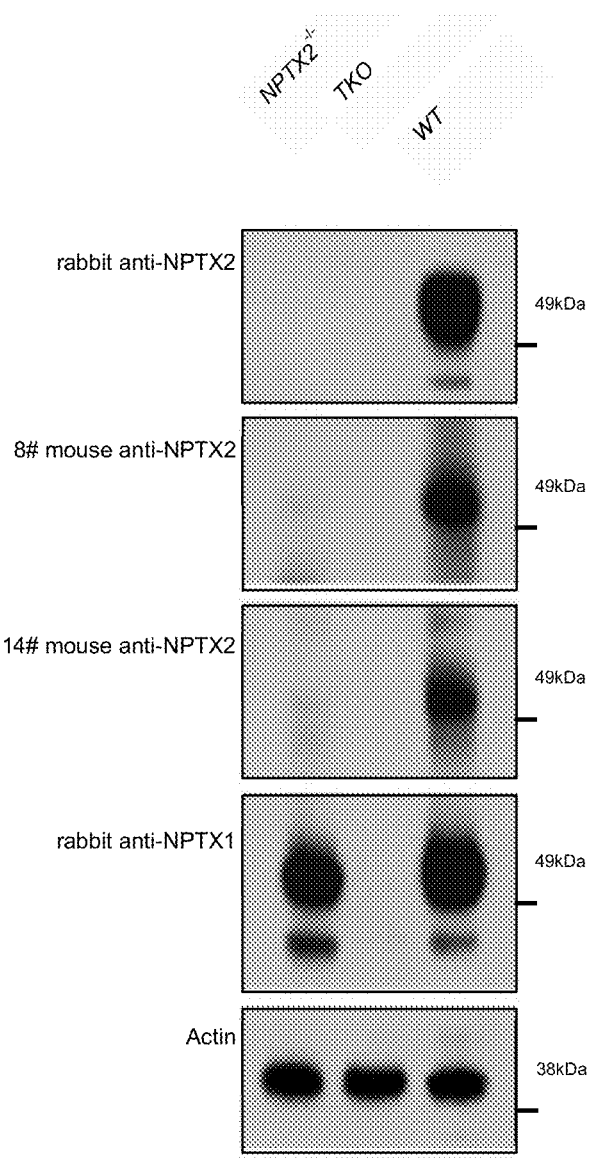
FIG. 16. Specificity test of NPTX2 ELISA. A: Specificity test of mouse anti-NPTX2 McAb. Mouse anti-NPTX2 McAb 8 # and 14 # specifically recognize NPTX2, not NPTX1, not show non-specific reaction on NPTXs triple knock-out (TKO) same as control rabbit anti-NPTX2. B: Mouse anti-NPTX2 McAb give a same pattern as rabbit anti-NPTX2 (verified polyclonal Ab) on both human CSF and human brain samples. C: NPTX2 ELISA shows a highly correlation (c.c.=0.8259) with the results of Western blot with rabbit anti-NPTX2 control.
Figure 16B:
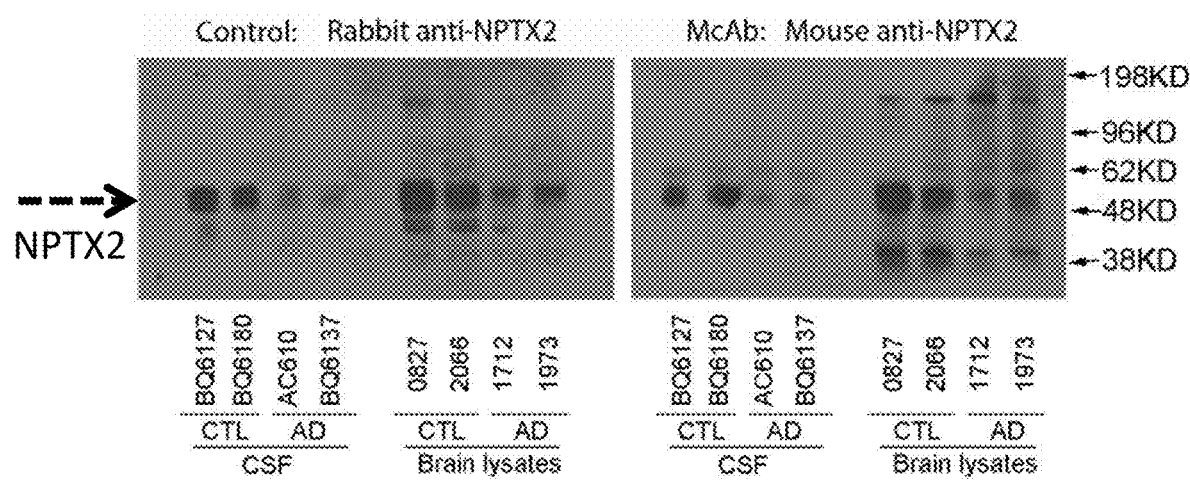
Figure 16C:
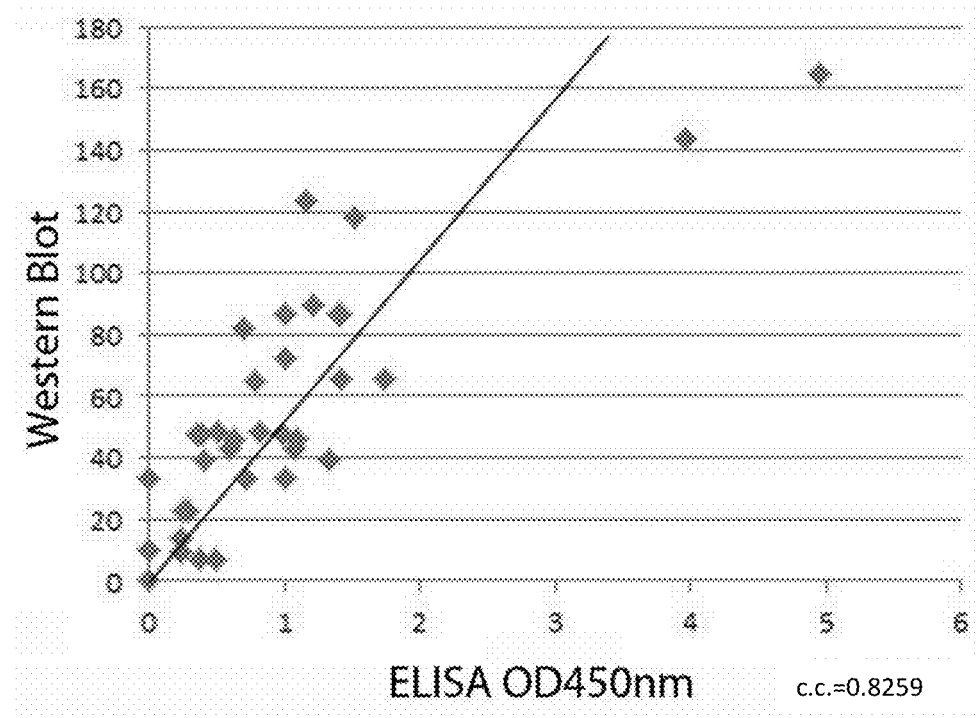

NPTX1 and NPTX2 are biomarkers of AD that correlate with cognitive impairment. NPTXR, NPTX1 and NPTX2 function as extracellular proteins (Xu et al., 2003) that can be released from the membrane surface (Cho et al., 2008). Accordingly, it is anticipated that NPTX proteins will be present in the CSF and provide an indication of surface expression in brain. Consistent with this model, NPTX1, NPTX2 and NPTXR are detected in lumbar CSF of human subjects as a high molecular weight complex that is resolved into individual NPTXs with reducing agent on SDS-PAGE (FIGS. 11A and 11B). As in brain tissue samples, NPTXR levels were not significantly different between AD and age matched control patients in CSF (FIG. 6A, 6B and Table 2). By contrast, both NPTX1 and NPTX2 levels were significantly reduced in AD patients. The reduction of NPTX2 in CSF is consistent with global reductions in AD brain (FIG. 1B). Reduction of NPTX1 in CSF is notable since it is not reduced in AD brain. Levels of NPTX1 closely correlated with NPTX2 within samples of both control and AD patients (FIG. 6C). This suggests that NPTX1 released into CSF may represent a distinct fraction of the total that is linked to NPTX2 expression, and is consistent with the special role for NPTX2 in defining aggregate properties of the mixed NPTX complex (Xu et al., 2003).

Reductions of NPTX1 and NPTX2 correlated with cognitive function assessed by mini mental status exam (MMSE) in the combined groups (FIGS. 6D and 6E). NPTX1 and NPTX2 levels did not correlate with age or gender, but NPTX2 levels showed a trend of reduction in ApoE4 subjects (Table 3). As a bioassay, NPTX1 or NPTX2 reduction was comparable in sensitivity to reductions of Aβ42 assayed on the same samples (Table 2). However, NPTX1/2 reductions did not correlate with Aβ42 within samples (FIG. 11C), again suggesting that these markers detect different aspects of AD pathophysiology. NPTX1 and NPTX2 reductions were also detected in CSF of patients with clinical diagnosis of frontotemporal dementia (FTD) in our preliminary studies (FIG. 6F, 6G). This, together with brain data from DS cases indicates that reductions of NPTX1/2 are not specific to AD, but are consistently linked to cognitive impairment.

Discussion

The present study implicates NPTX2 as a determinant of cognitive decline in sporadic AD, and suggests that failure of its homeostatic mechanism is central to multiple aspects of AD pathogenesis. Findings are also relevant for DS. Data indicating that NPTXs bind BACE1 and regulate its endocytosis provides further insight into the link between activity and Aβ generation. It is striking that IEG mechanisms control the activity of the two enzyme pathways that process APP to generate Aβ in normal brain (this report and (Wu et al., 2011)). Moreover, for both Arc and NPTX, the mechanism of regulatory control of APP processing appears to be coordinate with control of surface AMPA receptors. Current data suggest that NPTX2 down-regulation is a consequence of reduced mRNA synthesis rather than accelerated turnover of the protein.

A model in which the NPTX2 contribution to homeostatic scaling fails in AD integrates well with known pathophysiology. During the normal homeostatic scaling process, increased activity in excitatory neurons results in transcriptional induction of IEGs including NPTX2 mRNA and protein (Chang et al., 2010). NPTX2 protein is transported to presynaptic sites where it is secreted and accumulates at excitatory synapses on fast spiking, parvalbumin interneurons (PV-IN) (Chang et al., 2010). Mechanisms of NPTX secretion have not been described, but the selective accumulation may be related to the proteoglycan perineuronal nets that surround these neurons (Chang et al., 2010). Accumulations of NPTX2 bind AMPA receptors GluA1 and GluA4 and enhance synaptic efficacy. This results in increased firing of PV-INs with the consequence of increased GABA network activity and reduced excitatory network activity. The NPTX2 mechanism thus shifts the balance of excitation to inhibition to reestablish activity patterns of the excitatory neurons that originally expressed NPTX2. PV-IN networks provide temporally precise feed-forward and feedback circuits important for synchrony of pyramidal neuron firing and information processing (Buzsaki and Chrobak, 1995; Klausberger and Somogyi, 2008; McBain and Kauer, 2009). Phenotypes in NPTX2 knockout mice are consistent with a loss of inhibitory adaptation to activity showing enhanced kindling of epileptic stimuli (Chang et al., 2010), and absence of ocular dominance plasticity that can be rescued by GABA agonist (Gu et al., 2013). In mouse amyloidosis models, inhibitory circuits undergo major adaptive changes (Palop et al., 2007), and interruption of PV-IN function results in increased vulnerability to seizures, accelerated cognitive failure, and early death (Verret et al., 2012). Thus, mouse models demonstrate a requirement for PV-IN mechanisms to adapt to amyloidosis. In humans, this adaptation may require NPTX2. Human AD subjects are at increased risk for seizure beginning early in disease, and EEG findings are consistent with interruption of interneuron circuitry (Vossel et al., 2013). Human subjects with asymptomatic AD provide important precedent by establishing that Aβ plaque and tau pathology are not sufficient to cause cognitive failure, and suggest that normal cognition can be retained so long as NPTX2 expression and excitatory homeostasis is maintained. Clinical trials with BACE1 inhibitors should reveal if Aβ reduction is sufficient to reverse cognitive failure.

In normal neuronal networks, the IEG response to agents that cause sustained activation (such as addition of picrotoxin to cultures) is rapid and transient, consistent a role in reestablishment of set-point activity patterns (Turrigiano, 2012). Since each IEG mediates a non-redundant action, failure of the NPTX2 mechanism is anticipated to cause sustained drive for other homeostatic mechanisms due to the persistence of increased activity. The contribution of Arc to activity-dependent Aβ generation and synaptic failure was noted in the Introduction. NPTX1 expression is normally down-regulated as part of the homeostatic response (FIG. 7A). This is predicted to increase BACE1 activity and contribute to activity-dependent increases of Aβ generation. Reductions of NPTX1 in human CSF suggest this activity-dependent adaptation may be occurring normally in AD. If NPTX1 is down-regulated on the surface of brain neurons in AD it would contribute to increased BACE1 activity and further enhance Aβ generation. Finally, if Aβ oligomers activate group 1 mGluRs as reported by several groups (Shankar et al., 2008; Um et al., 2013), the action of mGluRs in homeostatic scaling will cause synaptic depression in a spatial dendritic pattern unrelated to informational synaptic activity and interrupt processes that scale synaptic weights to preserve information storage (Turrigiano, 2012). In these instances, pathological consequences arise from aberrant activation of functional pathways.

CSF NPTX levels provide mechanism-based biomarkers that may be useful to identify and monitor patients who are most responsive to GABA- (Bakker et al., 2012) or BACE1-directed therapies (Yan and Vassar, 2014). NPTX down-regulation is not specific to AD since it also occurs in DS and a cohort of patients with FTD. This is consistent with the hypothesis that NPTX mechanisms are part of an adaptive response that is vulnerable to failure rather than a primary cause of AD. DS is linked to endosomal dysfunction that can be reversed by BACE1 inhibitor (Jiang et al., 2010). Because NPTX2 down-regulation appears to be an independent determinant of disease and linked to cognitive decline, it provides an candidate "common final pathway" target to assess for impact of genetic variations linked to AD (Cruchaga et al., 2014; 2013; Tosto and Reitz, 2013) that have defied association with other markers of pathogenesis (Kauwe et al., 2011).

TABLE 2

Summary of human CSF Analysis in Alzheimer's Disease

|  | Normal control n = 30 | Alzheimer's Disease n = 30 | Control vs AD |
|---|---|---|---|
| Age (Years) | 70.03 ± 8.36 | 73.00 ± 10.62 | p = 0.20 |
| Education (Years) | 16.72 ± 2.23 | 16.34 ± 2.42 | p = 0.52 |
| Gender (F/M) | 23/13 | 9/21 | |
| MMSE | 29.50 ± 0.65 | 23.00 ± 4.37 | p < 0.001 |
| NPTX2 | 100.00 ± 45.03 | 44.60 ± 39.10 | p < 0.001 |
| NPTX1 | 100.00 ± 58.78 | 60.09 ± 32.28 | p = 0.009 |
| NPTXR | 100.00 ± 55.29 | 120.40 ± 58.89 | p = 0.15 |
| ApoE ε4 (%) | 38 | 62 | |
| Aβ42 (pg/ml) | 193.80 ± 57.02 | 124.70 ± 32.17 | p < 0.001 |
| p-Tau181 (pg/ml) | 41.62 ± 19.24 | 59.02 ± 42.65 | p = 0.34 |
| Tau (pg/ml) | 73.96 ± 48.86 | 95.83 ± 37.70 | p = 0.02 |

CSF samples were obtained under IRB-approved research protocols, and handles and stored following best practices.
Levels of Aβ42, total Tau and p-Tau 181 were measured using the Inno AlzBio3 multiplex assay kits, and read on a Bio-Rad X-Map plate reader.
MMSE, mini mental state examination.
Data represent mean ± SD.

TABLE 3

Comparison of NPTX Levels in CSF from Individuals with ApoE ε4= vs ApoE ε4−.

|  | Normal control | | Alzheimer's Disease | | |
|---|---|---|---|---|---|
|  | AgoE ε4+ n = 10 | ApoE ε4− n = 18 | ApoE ε4+ n = 16 | ApoE ε4− n = 11 | ApoE ε4+ vs ApoE ε4− |
| NPTX2 | 82.13 ± 30.46 | 102.10 ± 53.04 | 36.94 ± 41.81 | 55.77 ± 38.33 | p = 0.116 |
| NPTX1 | 68.31 ± 31.77 | 106.00 ± 67.00 | 58.74 ± 34.98 | 67.93 ± 31.14 | p = 0.080 |
| NPTXR | 94.00 ± 46.24 | 109.13 ± 66.03 | 124.63 ± 59.73 | 113.16 ± 60.29 | p = 0.913 |

Data represent mean ± SD.

Example 2: Sandwich ELISA for NPTX2 Detection

The present inventors created a sandwich ELISA for NPTX2 detection in CSF. The ELISA comprises fluid sample treatment to break up NPTXs heterocomplexes to monomers and make NPTXs soluble and quantitatively measurable with ELISA and other ligand binding assays based on revealing the structure of NPTXs heterocomplexes in human body. In a specific embodiment, NPTX2 in CSF is reduced to monomer with Dithiothreitol (DTT) and stably exists after covalent modification using N-Ethylmaleimide (NEM) irreversible blocker. In addition, the present inventors created a soluble and antibody recognized standard NPTX protein by mutating all 3 cysteines involved in heterocomplexes assembly. The present inventors also produced anti-NPTX2 and NPTX1 monoclonal antibodies (McAbs).

Thus, in one aspect, the present invention provides ELISA kits for NPTX2 detection in CSF. In one embodiment, the kit comprises: anti-Narp coated ELISA plate, biotinylated anti-Narp, HRP-Avidin, Narp standard protein; sample dilution buffer; washing buffer; sample pre-treat reagent A & B; DAB substrate solution; stopping solution; and operation instructions.

In certain embodiments, the NPTX2 ELISA can be carried out as follows:
1. Add 100 µl sample into the well of ELISA plate, incubate at 4° C. for overnight.
2. Wash 3 times with washing buffer.
3. Add 100 µl of biotinylated Narp specific antibody at application concentration and incubate with shaking at room temperature for 1 hour.
4. Wash 4 times with washing buffer.
5. Add 100 µl of HRP-Avidin at application concentration and incubate at room temperature for 1 hour.
6. Wash 5 times with washing buffer.
7. Add 100 µl of DAB solution at application concentration and incubate in dark at room temperature for 0.5 hour with shaking.
8. Add 100 µl of stopping solution and mix well.
9. Measure OD value at 450 nm.

Example 3: NPTX2, a Mechanism-Based CDF Biomarker for Cognitive Failure in Alzheimer's Disease A central question in Alzheimer's disease (AD) is why individuals lose memory abilities. Current imaging and neuropathological studies recognize that high levels of Aβ amyloid and neurofibrillary tangles can be present in cognitively normal individuals and typically precede dementia by years. Here we report that NPTX2, a protein that contributes to de novo gene expression-dependent memory, is prominently down-regulated in brains of individuals with late onset AD but is normally expressed in subjects with typical AD pathology who retain cognitive function. NPTX2 down-regulation is linked to reduced NPTX2 mRNA; an identified target of microRNAs up-regulated in AD brain. NPTX2 is a secreted protein detected in CSF where levels correlate with cognitive performance in AD and MCI subjects. Studies support a "second-hit" model wherein loss of NPTX2 in AD removes an important activity-control mechanism resulting in amplified signaling through AB generating pathways and failure of a critical mechanism of memory.

Introduction

Memory is dependent on rapid de novo mRNA and protein synthesis occurring within a brief time window of experience. Analysis of this genomic program reveals mechanisms that strengthen active synapses and circuits while weakening inactive connections. A mechanism mediated by the immediate early gene Arc is notable in that it increases the rate of processing of amyloid precursor protein (APP) to generate Aβ This pathway normally functions to weaken inactive synapses but also underlies elevated Aβ deposition in mouse amyloid models and appears relevant to the pathogenesis of human AD. This point of convergence between physiological mechanisms of memory and pathophysiological mechanisms of AD rationalizes many observations regarding synaptic changes in models of AD. For example, Aβ amyloid activates metabotropic glutamate receptor mGluR5 and can anomalously drive synaptic weakening to interfere with information storage, and this has been suggested as the basis of cognitive failure in AD. However, recent studies using positron emission tomography probes to detect brain amyloid reveal its presence in cognitively normal individuals decades before cognitive failure. Moreover, neuropathological studies have reported the seemingly paradoxical presence of prominent AD pathology in subjects who were cognitively normal at death. Understanding that Aβ amyloid may not be directly causal for dementia has led to a search for other pathophysiological mechanisms that underlie memory loss.

Neuronal Pentraxin 2 protein (NPTX2; also termed Narp or NP2) mediates a distinct mechanism of de novo protein synthesis-dependent synaptic plasticity that has not previously been implicated in AD pathophysiology. NPTX2 protein is made and secreted by excitatory neurons and accumulates at excitatory synapses on interneurons that express parvalbumin where it acts to strengthen the excitatory drive of inhibitory circuits. Mouse genetic models indicate an essential role for NPTX2 in developmental plasticity of the visual cortex, and in facilitation of excitatory circuits capable of high-frequency coordinate firing relevant to information storage. Here, we report that NPTX2 is down-regulated in AD and represents a second point of convergence between mechanisms of de novo synthesis-dependent plasticity and AD. In contrast to mechanisms driving Aβ generation, NPTX2 down-regulation occurs in close association with cognitive dysfunction. The shared role of Aβ generating and NPTX2 mechanisms in controlling neuronal activity supports a model of cooperative pathophysiology.

Materials and Methods

Mouse Strains. NPTX2$^{-/-}$ mice in congenic C57BL/6J background were obtained from Mark Perrin's lab. APPswe/PS1ΔE9 transgenic mice (here abbreviated hAPP) strain was obtained from Dr. Philip Wong. hAPP mice with single copy of transgene were crossed with NPTX2$^{-/-}$ to generate hAPP/NPTX2$^{-/-}$, which were then crossed with NPTX2$^{-/-}$ to generate hAPP/NPTX2$^{-/-}$. Similarly, WT (C57BL/6J) were crossed to hAPP mice to generate hAPP/WT, which were crossed to WT to generate cohort. For both WT and NPTX2 deletion mice cohorts, ~50% of progeny of the final cross were expected to carry the hAPP transgene, and this assured that mice carry a single copy of the transgene. All procedures involving animals were under the guidelines of JHMI Institutional Animal Care and Use Committee.

Human Specimens. Human brain tissue of Alzheimer's disease (AD) and asymptomatic AD (ASYMAD) was obtained from the Johns Hopkins Brain Resource Center, which includes subjects from the Baltimore Longitudinal Study of Aging. Subjects were recruited by the Clinical Core at Johns Hopkins Alzheimer's Disease Research Center (ADRC) from the community or from the cohort already enrolled in the Baltimore Longitudinal Study on Aging. The assessment procedures have been coordinated by Joint Clinical Core meetings that assure standardization of diagnostic procedures for annual medical, neurologic, psychiatric and neuropsychological evaluations of all subjects. The Neuropathology Core arranges and performs autopsies on clinically well-characterized participants who agreed to autopsy. Results of neuropathological autopsies are then discussed on clinical-pathological conferences attended by members of the Clinical and Neuropathology Cores. Human Down syndrome (DS) brain tissue was obtained from the NICHD brain and tissue bank for developmental disorders. Brain samples were lysed in RIPA buffer plus protease inhibitor cocktail at a dilution factor 1:50 for Western blot analysis.

Human cerebrospinal fluid (CSF) samples were obtained under IRB-approved protocols from participants in the UCSD Alzheimer's Disease Research Center. All participants gave informed consent before taking part in the study. CSF samples were dissolved with SDS loading buffer, and 12 µl of CSF were loaded to SDS-PAGE and subsequent Western blot. All CSF samples were frozen at collection and assayed after 1st thaw. We noted that NPTX protein levels decreased with multiple freeze thaw cycles.

Reagents. Rabbit anti-NPTX1, anti-NPTX2 and anti-NPTXR were described previously. Mouse anti-NPTX2 monoclonal antibody was made against GST NPTX2 N-terminus (a.a. 1-220) fusion protein. Antibody specificity was confirmed with the brain tissue of NPTX2$^{-/-}$ mice. Mouse anti-Arc monoclonal antibody was described previously. All other antibodies are from commercial companies. Mouse anti-Beta Amyloid monoclonal antibody 6E10 is from COVANCE (Cat. Number: SIG-39320); Mouse anti-APP N-terminus monoclonal antibody 22C11 is from Millipore (Cat. Number: MAB348); Rabbit ant-Egr1 (C-19) is from Santa Cruz (Cat. Number: sc-189); Mouse anti-actin monoclonal antibody is from Sigma (Cat. Number: A 2066); ECLTM anti-mouse IgG HRP is from GE Healthcare (Cat. Number: NA931V); ECLTM anti-rabbit IgG HRP is from GE Healthcare (Cat. Number: NA934V). ImmunoPure Metal Enhanced DAB substrate kit is from Pierce (Cat. Number: 34065); Western blot substrate SuperSignal West Pico Luminol Enhancer Solution (Cat. Number: 1859675) and SuperSignal West Pico Stable Peroxide Solution (Cat. Number: 1859674) are from Thermo Scientific.

Western Blot. Cultured cells or brain tissue were lysed with a modified RIPA buffer containing 1% Triton, 0.5% Na-deoxycholate, 0.1% SDS, 50 mM NaF, 10 mM Na4P2O7, 2 mM Na3VO4, and protease inhibitor cocktail in PBS, pH7.4. Protein extracts were separated by 4-12% SDS-PAGE, transferred to PVDF membranes, blocked with 5% non-fat milk, and then probed with primary antibodies for overnight at 4° C. After washes with TBST (TBS with 0.1% Tween-20), membranes were incubated with HRP-conjugated secondary antibodies for 1 hr at room temperature (RT). Immunoreactive bands were visualized by the enhanced chemiluminescent substrate (ECL, Pierce) on X-ray film and quantified using the image software TINA. Actin and PSD95 are used as loading controls. Proteins migrating similarly in SDS-PAGE gel are assayed on different blots without stripping.

NPTX2 ELISA. Preparation of His-tagged NPTX2 Standard protein: Full length NPTX2-myc in pRK5 vector is used as a template. The N terminal fragment encoding amino acid 1 to 201 was amplified with primers 5' GCAAGGATCCCAAGCCCAGGATAACCC 3' (SEQ ID NO:19) and 5' CATGTCGACT-CATGCACTGTTGCCTCTCTC 3' (SEQ ID NO:20), and then cloned into pQE30 vector (Qiagen) at the polylinker sites of BamH1 and SalI. The protein was expressed in XL1-blue host cells induced with 1 mM IPTG. The expressed NPTX2 fragment was purified with NI-NTA agarose column (Qiagen), and the protein concentration was quantified with BCA kit (Thermo Scientific).

ELISA assay: Basically, the operation follows the regular process of ELISA. Briefly, 0.5 of rabbit anti-NPTX2 antibody in 50 mM Na2CO3 buffer (pH9.5) was coated to the ELISA plate (Nunc) at 4° C. for overnight. Next day, after blocking with blocking solution (5% BSA in PBS) for 1 hr at RT, 100 µl of the series of diluted NPTX2 standard protein as well as CSF samples were added into wells and incubated at RT for 1 hr with constant shaking. After washing with TBS, 100 µl of biotinylated mouse anti-NPTX2 antibody was applied and incubated at RT for 1 hr. Then, 100 ul of HRP conjugated streptavidin (Biolegend) was added and incubated for 1 hr. After washing with TBS, 100 ul of DAB substrate (Biolegend) was applied and incubated for half hour at RT in dark. In the end, 100 µl of 4 M $H_2SO_4$ stopping solution was added and the absorbance was measured at 450 nm. The absolute levels of NPTX2 in CSF were determined by the calculation based on standard curve.

Aβ Assay in Brain. Brain was homogenized with homogenize buffer (PBS with complete proteinase inhibitor cocktail and 1 mM PMSF, pH7.4) at a tissue to buffer volume ratio of 1:10. Lysates were centrifuged at 100,000 g for 30 min at 4° C. Supernatant was collected for PBS soluble AO measurement. The pellet was solubilized with 70% formic acid for 1 hr on ice. After 100,000 g centrifugation for 1 hr at 4° C., the supernatant was neutralized with 1 M Tris-base according to the ratio of Tris-base/sample=16/1. AO levels were determined with ELISA kit (human A1340 kit, Cat. Number KHB3482 and human Aβ42 kit, Cat. No. KHB3441 from Invitrogen).

Plaque Staining. Mouse brain (sagittal hemi forebrain) was fixed by immersion in 10% formaldehyde in PBS (pH7.4) and embedded in paraffin and sectioned to 5 µm thickness on slides. Sections were deparaffinized and hydrated by incubating slides at 60° C. for 30 min and then transferred into Xylene. The paraffin was removed after 3 changes of Xylene for 5 min. Then, slides were treated 3 min with sequential changes of 100%, 95%, and 70% ethanol and ddH2O for 3 times. Slides were then processed further for immunohistostaining or silver staining.

Tissue immunohistostaining. Protein antigenicity was unmasked by the treatment with 88% formic acid for 5 min. Slides were washed with ddH$_2$O 3 times for 5 min each. The endogenous peroxidase activity was inhibited with 1.5% hydrogen peroxide in methanol for 5 min. Sections were treated with blocking solution (4% horse serum, 0.4% Triton in TBS) for 1 hr at RT and incubated with primary mouse anti-Aβ antibody at RT for overnight. Slides were washed with TBS 3 times and incubated with biotinylated goat anti-mouse IgG for 1 hr at RT. After 3 washes with TBS, tissue sections were incubated with Avidin/Biotin mixture at RT for 1 hr. Then, they were developed in 3,3'-Diaminobenzidine (DAB) at RT for 10 to 20 min to achieve optimal contrast (monitoring under microscope). Reaction was stopped with ddH2O wash. The slides were dehydrated and mounted.

Silver staining. Slides were immersed in 20% AgNO3 solution for 30 min at RT and washed with ddH2O for 3 times. Then, slides were transferred to ammonium hydroxide titrated 20% AgNO$_3$ for 20 min in dark. After wash 5 times with ddH$_2$O, slides were transferred into ammonium ddH2O (3 drops of ammonium hydroxide in 250 ml of ddH2O) for 1 min, and then transferred into ammonium hydroxide titrated 20% AgNO$_3$ solution with 2 drops of the developer (20 ml of 37% formaldehyde, 0.5 g of citric acid and one drop of nitric acid in 100 ml ddH$_2$O). Slides were allowed to develop in dark with constant shaking until tissue turned dark with a tan to golden background. The staining solution was washed away with running tap water for 5 to 10 min. The reaction was stopped with 5% sodium thiosulfate for 5 min. Stained slides were dehydrated and mounted.

RNA Extraction and Quantitative PCR. Total RNA and small RNA were extracted by mirVana miRNA isolation kit (Ambion) according to the manufacturer's protocol. Isolated RNA was treated with DNase to remove DNA (Turbo DNA-free kit, Ambion). One µg of isolated total RNA was then immediately reverse-transcribed into cDNA using the SuperScript First-Strand Synthesis System for RT-PCR (Invitrogen). Quantitative PCR was performed with a StepOne Plus machine (Applied Biosystem) using SYBR green ROX qPCR mastermix in a 96-well optical plate. PCR cycling consists of 95° C. for 10 min, followed by 40 cycles of 95° C. for 30 sec, 64° C. for 30 sec and 72° C. for 30 sec. A melt curve was conducted to determine the specificity of PCR amplification. GAPDH was served as an internal control to nomalize data. To assay the direct transcripts pre-mRNA, primers were designed to bind with the intron of genes. For analysis of miRNA abundance, 30 ng of isolated samll RNA was reverse-transcribed using Taqman micoRNA reverse transcription kit (Applied Biosystems), and then subjected to Taqman microRNA assays according to manufacturer's protocol (Applied Biosystems) in StepOne Plus machine. PCR cycling consists of 95° C. for 10 min, followed by 40 cycles of 95° C. for 15 sec, 60° C. for 60 sec. RNU48 was served as an internal control to nomalize data.

Lentivirus Preparation. Precursors of miR-96, miR-1271 and miR-182 were amplified by PCR from genomic DNA, and inserted into PacI and NheI sites of lentiviral vector pSME2. Constructs were verified by sequencing. The lentiviral production plasmids contain four constructs: the pSME2 lentiviral backbone plasmid and three packaging plasmids pCMV-VSVG, pLP1 and pLP2. All constructs were transformed into stbl3 competent cells (Life Technologies) and then prepared using a standard protocol of Qiagen Maxiprep columns. Lentivirus was produced in HEK293T cells. Cells were grown in 175 cm$^2$ flasks that were pre-coated with 0.01% poly L-lysine (PLL) solution and maintained with DMEM containing 10% FBS. To improve transfection efficiency, 25 µM chloroquine was added to the medium of cultured HEK293T cells when 50% confluency, and transfection was performed one hour later. Cells were transfected using FuGene6 (Roche) with the ratio of 1 µg plasmid DNA: 3 µl FuGene6. 10 µM sodium butyrate was added to the medium 8 hr after transfection to improve transfection efficiency. Culture media were changed at 24 hr after transfection and collected at 48 hr after medium change (the transfection efficiency was monitored by GFP fluorescence). Virus particles were pelleted by centrifugation at 25,000 rpm for 2 hr at 4° C. (Beckman SW 28 rotor). Virus was aliquot and stored at −80° C. for future use.

Neuronal Culture. Primary neuronal cultures from embryonic day 17.5 (E17.5) mouse pups were prepared as described previously. Cells were plated on 0.02% PLL-coated wells at a density of 50×10$^4$ per well of 12-well plate, and infected with miRNA-expressing lentivirus immediately after plating. Seven days later, cells were harvested for RNA extraction or Western Blot assay.

DNA Methylation Assay—Pyrosequencing. DNA from postmortem brains of AD patients and healthy control was extracted using QIAamp DNA mini kit (Qiagen), then treated with bisulfite to convert cytosine residues to uracil, but leave methylated cytosine unaffected (EpiTect bisulfite kit, Qiagen). Bisulfite-treated DNA was amplified by PCR using Qiagen DNA methylation assay PM00126406, then subjected to pyrosequencing to determine the DNA methylation at Johns Hopkins University Genetic Resources Core Facility.

Luciferase Reporter Assay. NPTX2 3'UTR was amplified by PCR and inserted downstream of firefly luciferase in a reporter vector pmirGLO (Promega), which contains another luciferase, renilla luciferase as an internal reference control. Mutation of miR binding site on NPTX2 3'UTR was generated by QuickChange site-directed mutagenesis kit using primers containing mutated nucleotides (Agilent Technologies). Constructs were verified by sequencing. HEK293 cells were co-transfected with pmirGLO/WT or Mut NPTX2 3'UTR and miR mimics or negative control siRNA (Qiagen) by Lipofectamine 2000 (Life Technologies). One day later, cells were lysed and activities of firefly luciferase and renilla luciferase were assayed by Dual-luciferase reporter assay system (Promega). The ratio of firefly luciferase to renilla luciferase activity represented the effects of miR mimics on NPTX2 3'UTR.

Behavioral Testing. Overview: NPTX2$^{-/-}$ mice in congenic C57BL/6J background and their wild type controls were transferred from JHU breeding facilities to a mouse holding facilities adjacent to our behavioral lab. Mice were checked for general health and weighted. Only male mice were used in behavioral testing. Before start of the behavioral testing, each mouse was handled once a day for 3 days 5 min each. Open field tests were run first, followed by plus, and Y mazes with the most stressful procedures at the end of testing (fear conditioning). Before each test, mice were moved to the testing room and allowed to habituate to the new location for at least 1 hr before behavioral testing. All dry mazes and apparatuses were cleaned between subjects and trials with 30% ethanol. Behaviors in the plus maze, open field, and Y maze were recorded by computer-based video tracking systems (Any Maze™ 4.72, Stoelting Co, Wood Dale, Ill.). Each behavioral test was separated by at least 1 week.

Novelty-induced exploration testing: Novelty-induced hyperactivity was tested by placing the mouse in a novel environment such as the open field, plus maze, or Y maze. All tests were 5 min (unless noted otherwise) and have been described in detail elsewhere.

Anxiety levels in the open field: Open field testing was carried out as previously described. The squired white open-field arena 55×55 cm had 40 cm high sidewalls. The same illumination as in other tasks was used, consisting of indirect diffuse room light (eight 40 W bulbs, 12 1×). Each subject was released near the wall and observed for 15 min. Performance was recorded by a computer-based video tracking system (Any Maze™ 4.72, Stoelting Co, Wood Dale, Ill.). Activity measures included distance travelled, percent time spent in active exploration (episodes of movement≥5 cm/s), and speed of movement during active exploration. To analyze anxiety levels, the activity measures were broken down into two zones: central and periphery. The number of entries and time spent in the zones of the Open field was calculated. Percent of time spent in periphery (thigmotaxis) was used as a measure of anxiety.

Plus maze: Plus maze was carried out as previously described and consisted of four arms (63×6 cm) extended from a central platform (6×6 cm). Two opposing arms were open and two other arms were enclosed (40 cm-high side and end walls). The maze was elevated on four supporting metal poles 70 cm above the floor. Each mouse was placed in the center of the maze and the following measures were recorded during a single 5-min trial: (1) number of visits into the open and closed arms, (2) time spent in open and closed arms.

Spontaneous alternation: Spontaneous alternation task was carried out on a Y-shaped maze as previously described. Mice were placed at the end of one arm and allowed to explore freely for 5 min. The sequence of arm entries was recorded. The spontaneous alternation behavior was calculated as the number of triads containing entries into all three arms divided by the maximum possible alternations.

Fear conditioning: Cued and contextual fear conditioning was conducted as described before with some modifications. Conditioning was done in a mouse training chamber (Stoelting Co., Wood Dale, Ill.) with a shock grid floor and a contextual striped and checkered pattern on three of the walls. Testing and data collection were automated by ANY-Maze 4.72 software (Stoelting Co., Wood Dale, Ill.) according to the following protocol parameters: Light in the chamber 1.5 visible+1.5 Infrared, background noise 65 dB, smell 30% Ethanol, Minimum Freezing Duration=1000 msec. Mice were habituated to the training context for 2 min, during which the level of "pretraining" freezing was measured. Then, a delayed conditioning paradigm was used consisting of three presentations of conditioned stimulus (CS: white noise, 15 sec duration, 76 dB intensity) co-terminated with an unconditioned stimulus (1 sec-long scrambled footshock). Mice of both genotypes were randomly divided into two subgroups with mild (0.32 mA) or relatively strong (0.5 mA) shock intensity. Interstimulus intervals (ITI) lasted 2 min and, after the 3rd presentation of CS-US pairing, mice remained in the context for additional 45 sec to measure the final levels of freezing. Context-dependent fear behavior was analyzed 24 hrs later. Mice were placed in the same test chamber for 4 minutes without any CS or US administration, and freezias measured throughout the test. Mice were tested for CS-dependent freezing behavior 2 hrs later. Mice were placed in a novel test chamber with plain white walls on all sides and a solid floor. Fresh bedding was placed on the floor of this new chamber. Mice were allowed to explore the chamber for 120 seconds, then CSs were delivered as during training session. No US stimulus was presented. Levels of freezing were measured throughout all sessions and averaged over blocks of 15 sec.

Statistical Analysis. We used GraphPad PRISM version 5 to perform statistical analyses. Two-tailed t-test was employed to analyze difference between two groups. Behavioral tests of NPTX2$^{-/-}$ mice were analyzed by one way ANOVA with post hoc tests. Correlation analysis were performed by Pearson or Spearman's rank correlation. To evaluate the diagnostic value of CSF biomarkers, receiver operating characteristic (ROC) curve analysis were performed. Cut-off points were determined using sensitivity and specificity values that maximized Youden index.

Results

Figure 17A:
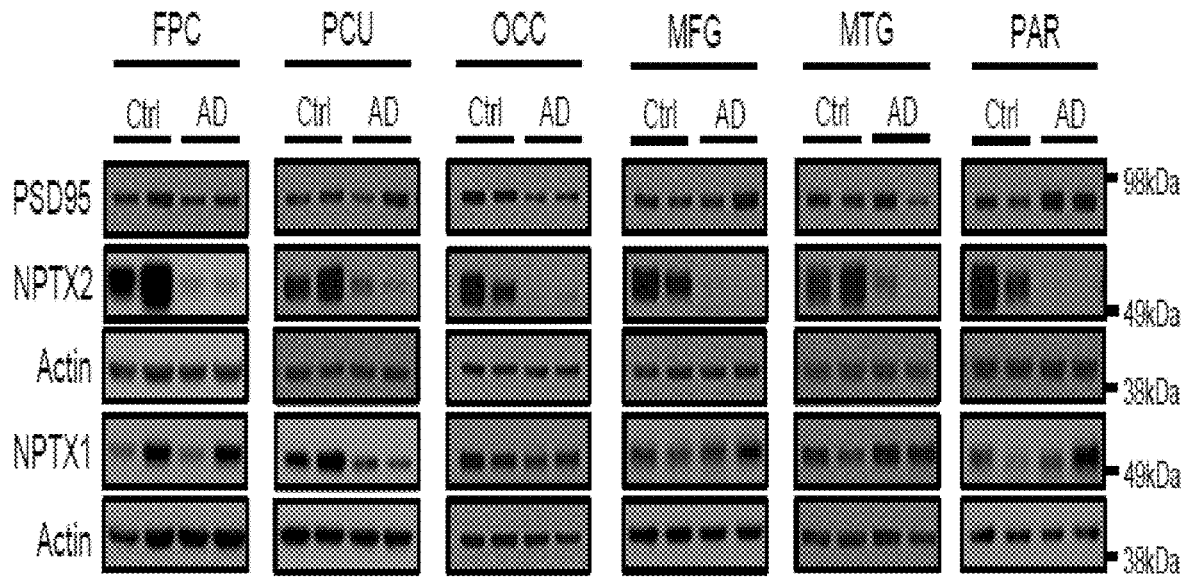
Figure 17B:
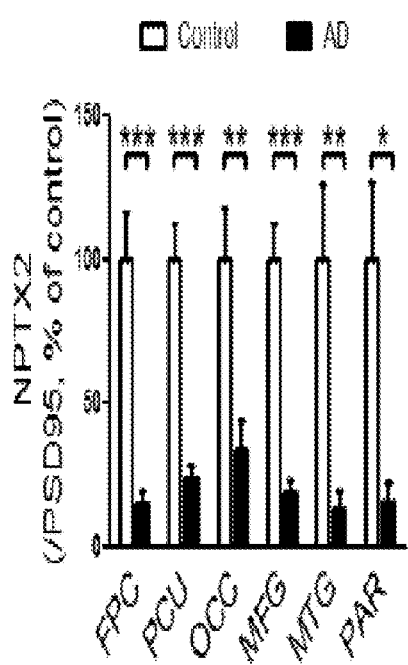
Figure 17C:
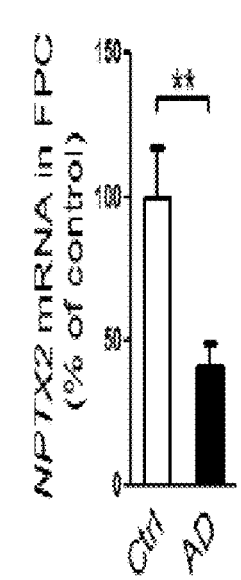
Figure 17D:
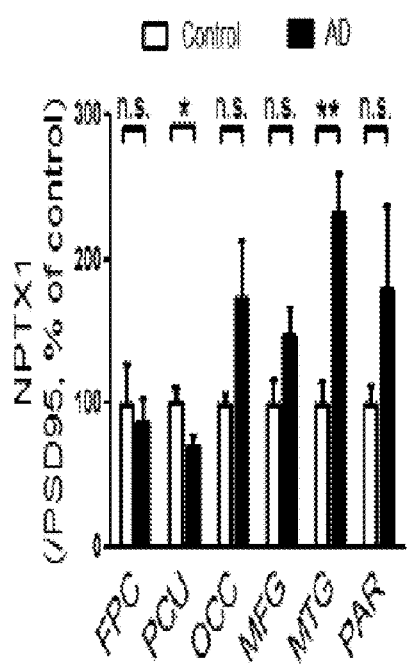
Figure 18A:
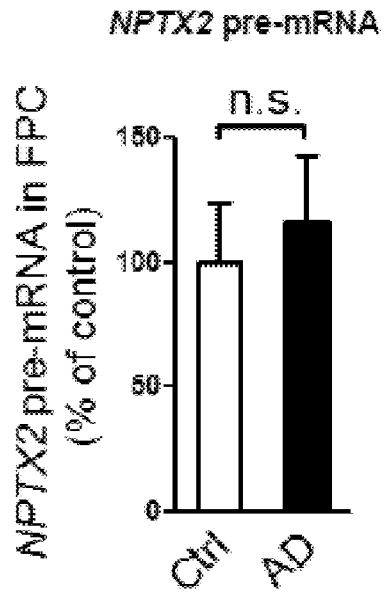
FIG. 18A-18I. miRNAs dysregulation in AD brains.
Figure 18B:
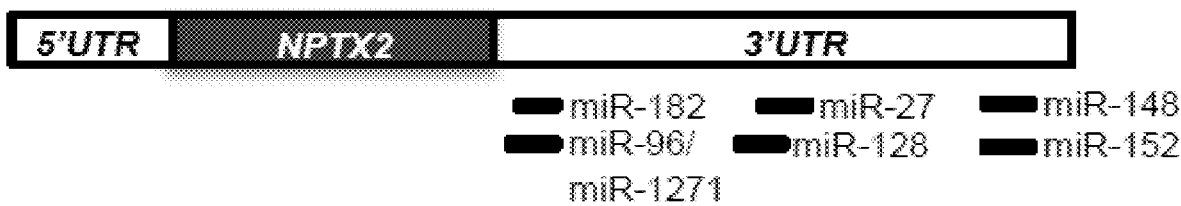
Figure 18C:
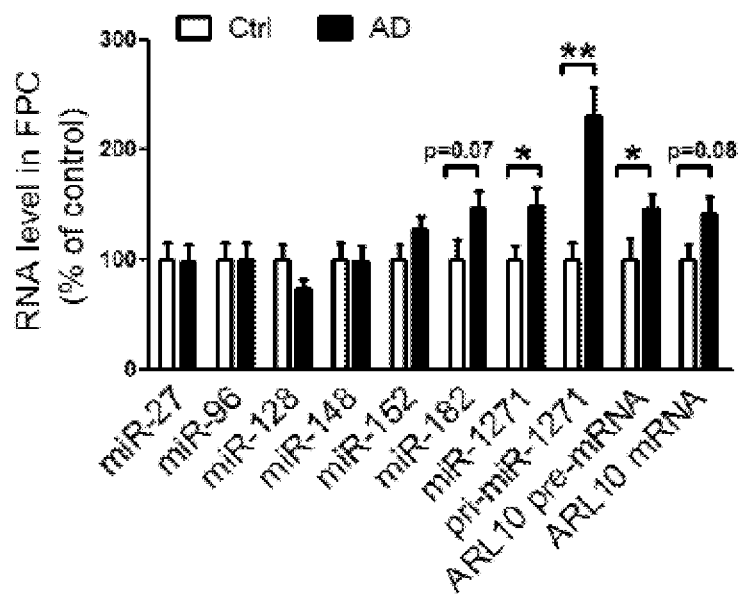
Figure 18D:
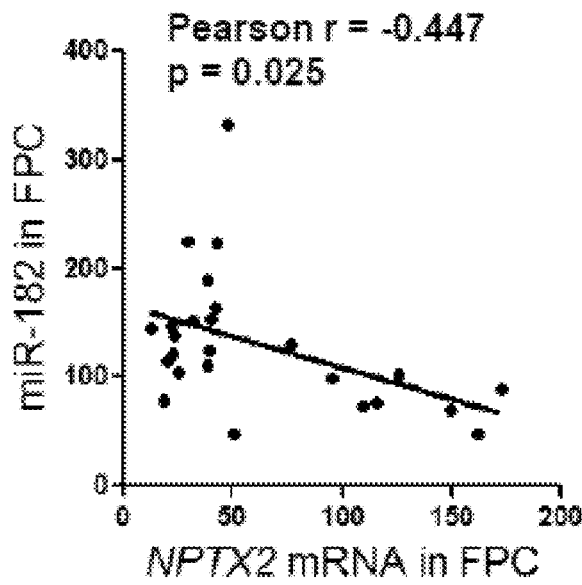
Figure 18E:
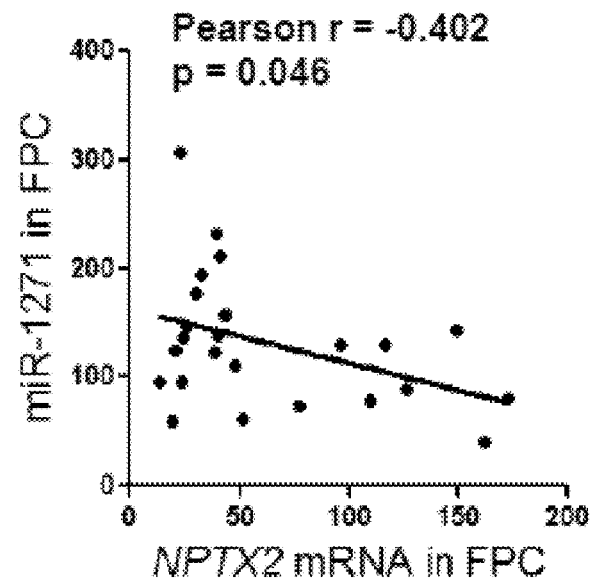
Figure 18F:
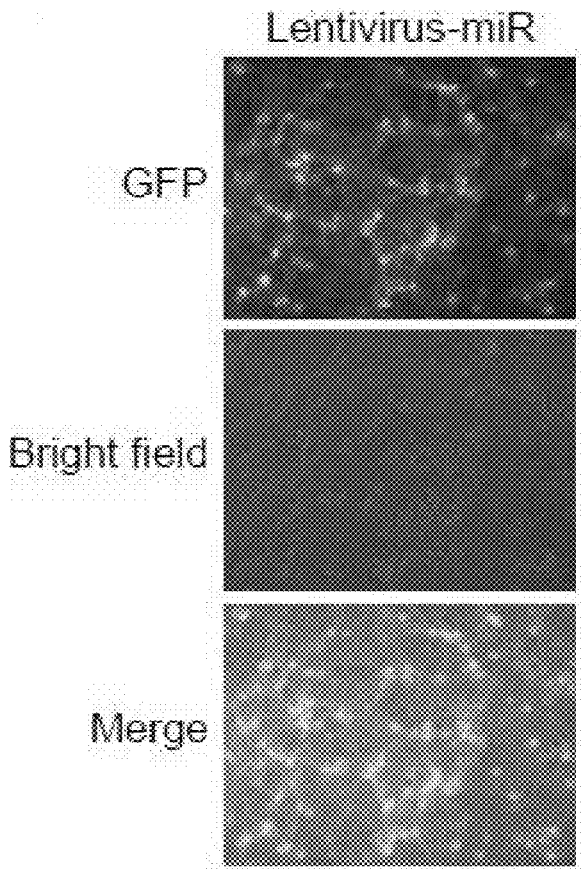
Figure 18G:
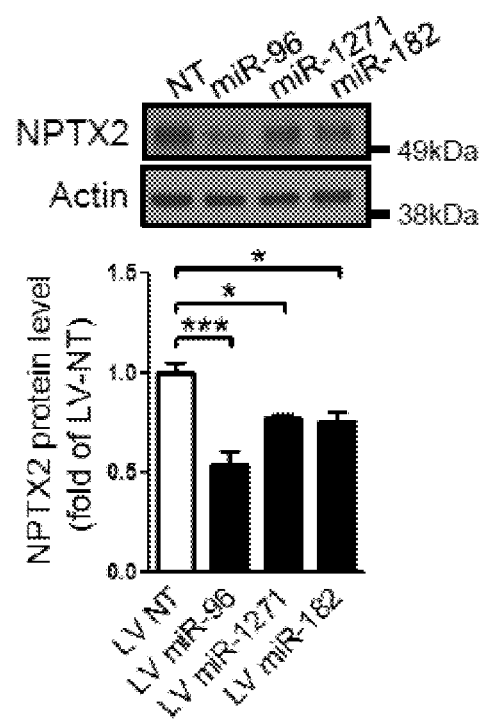
Figure 18H:
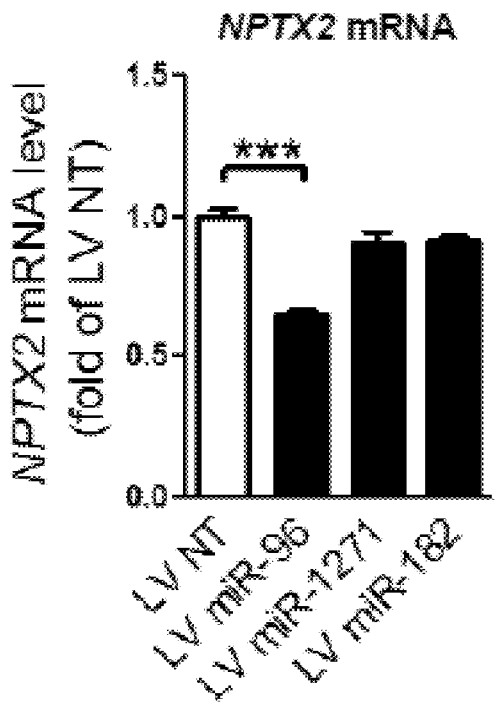
Figure 18I:
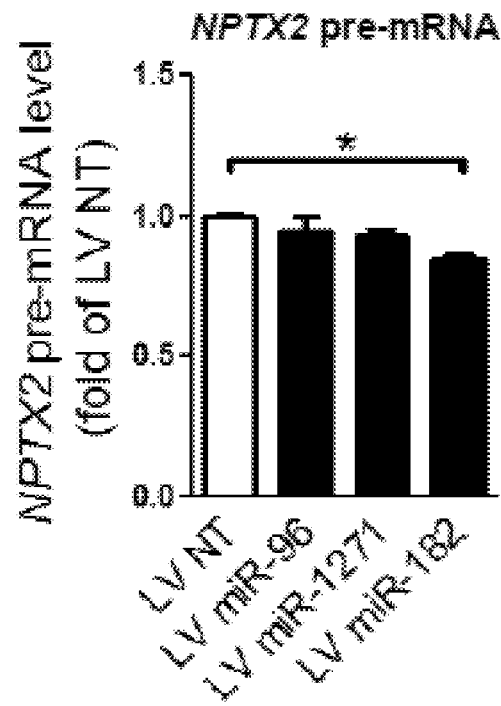
Figure 22A:
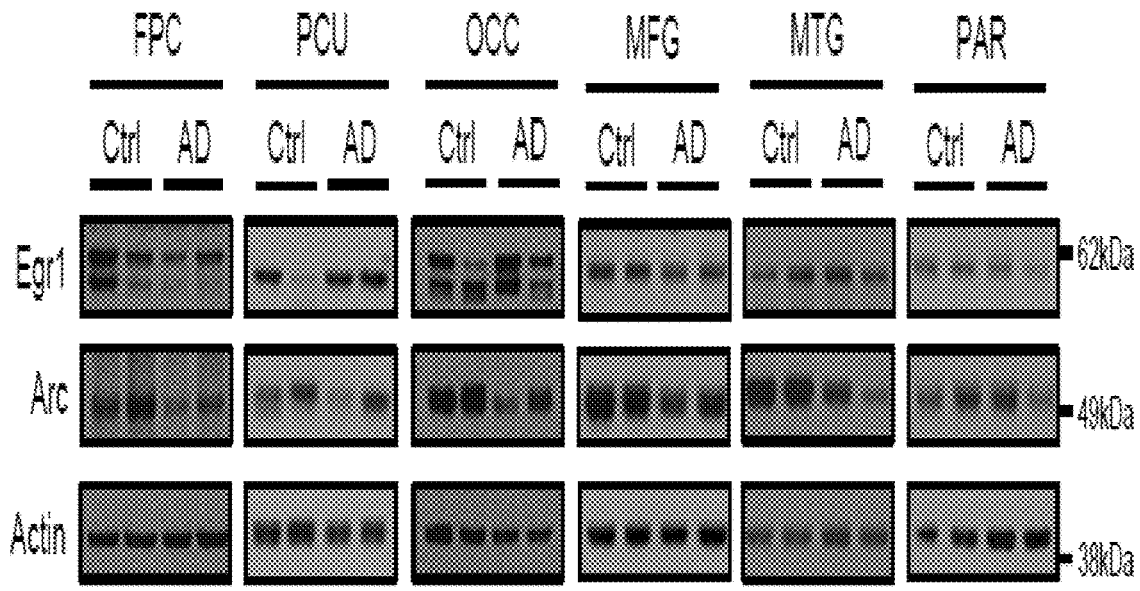
FIG. 22A-22B. Egr1 and Arc expression in different brain regions of control and AD subjects.
Figure 22B:
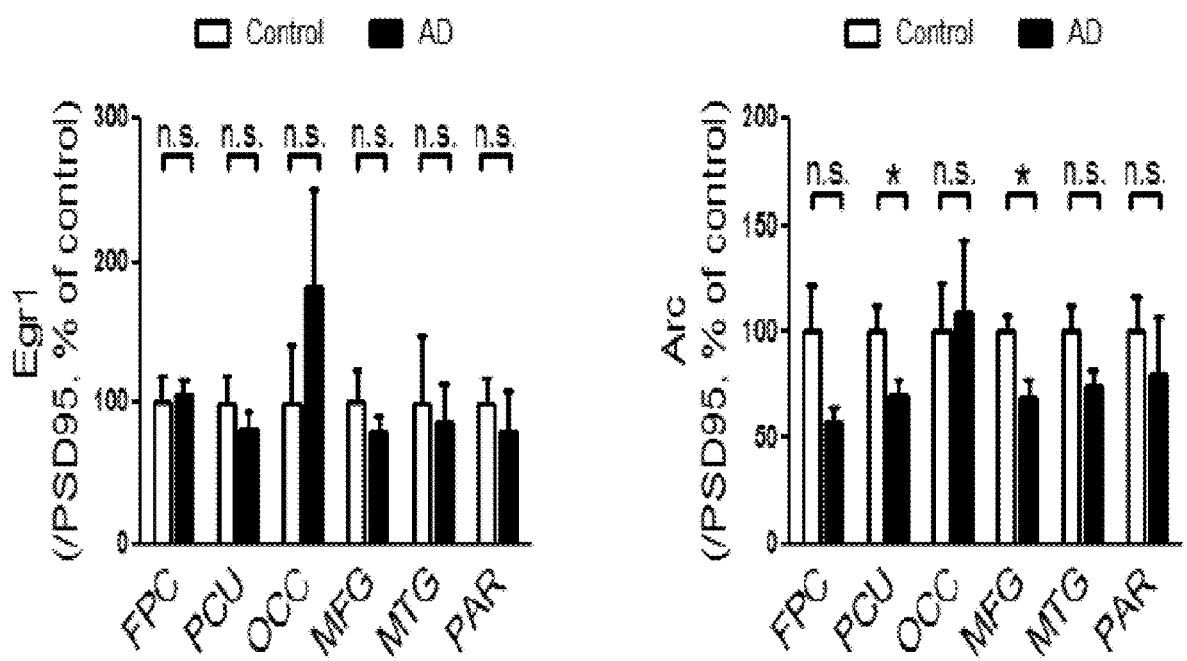
Figure 23A:
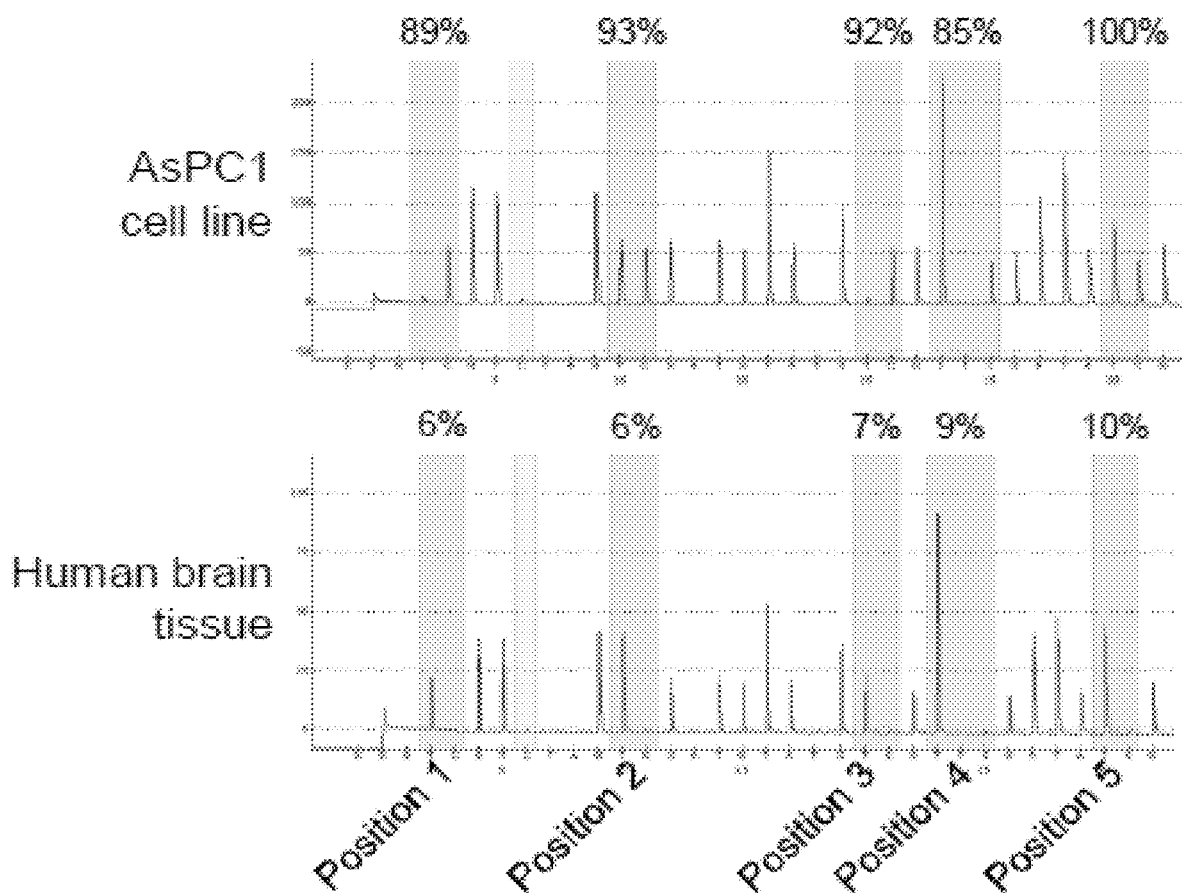
FIG. 23A-23B. Methylation of NPTX2 promoter in human brain.
Figure 23B:
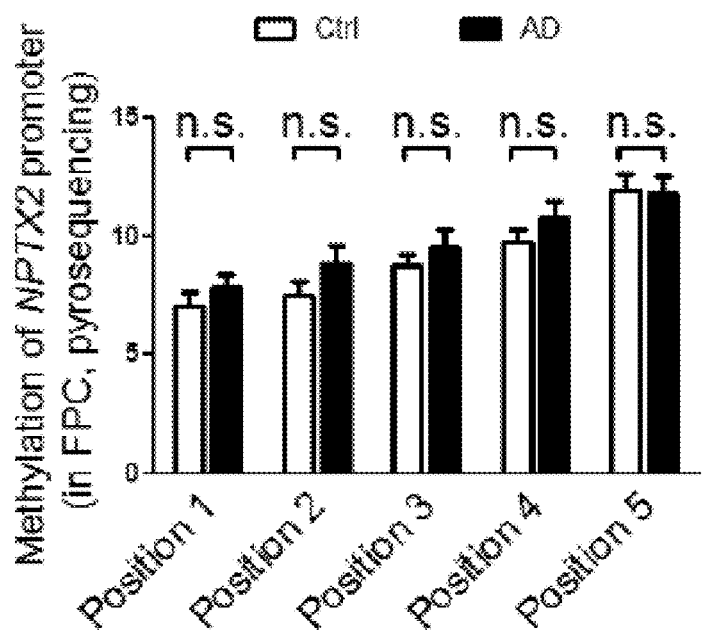
Figure 24A:
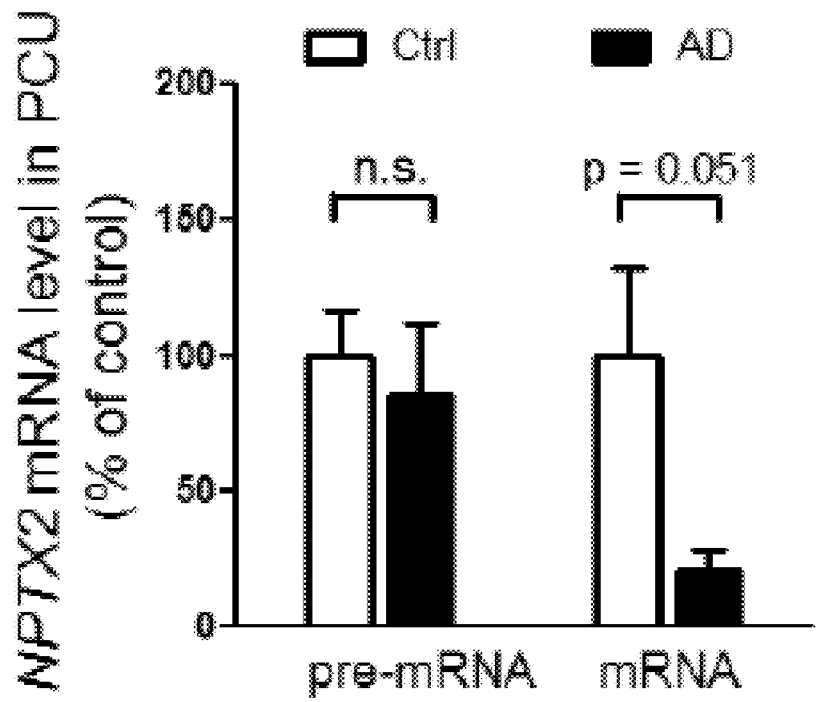
FIG. 24A-24B. Assays of NPTX2 mRNA and miRNA in AD PCU region.
Figure 24B:
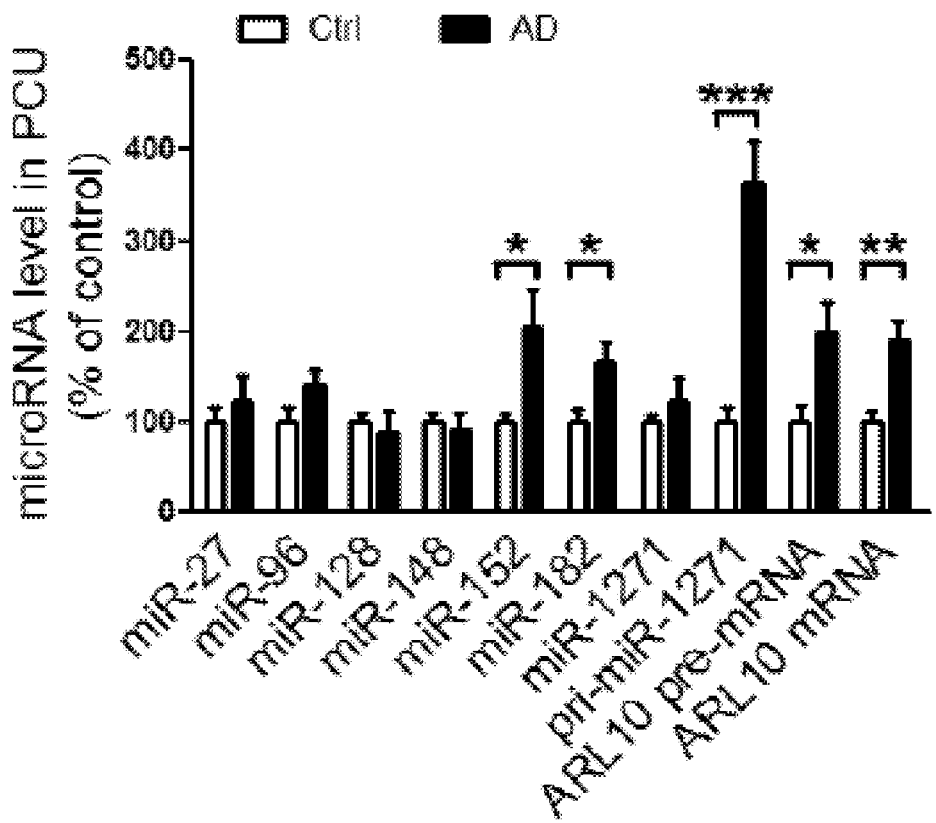
Figure 25A:
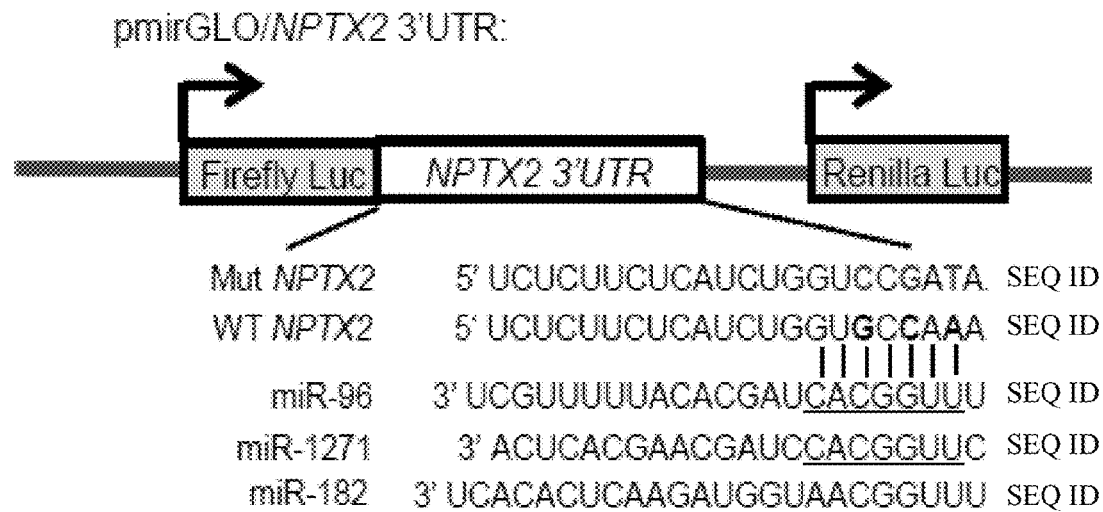
FIG. 25A-25B. miRNAs directly target NPTX2 3'UTR.
Figure 25B:
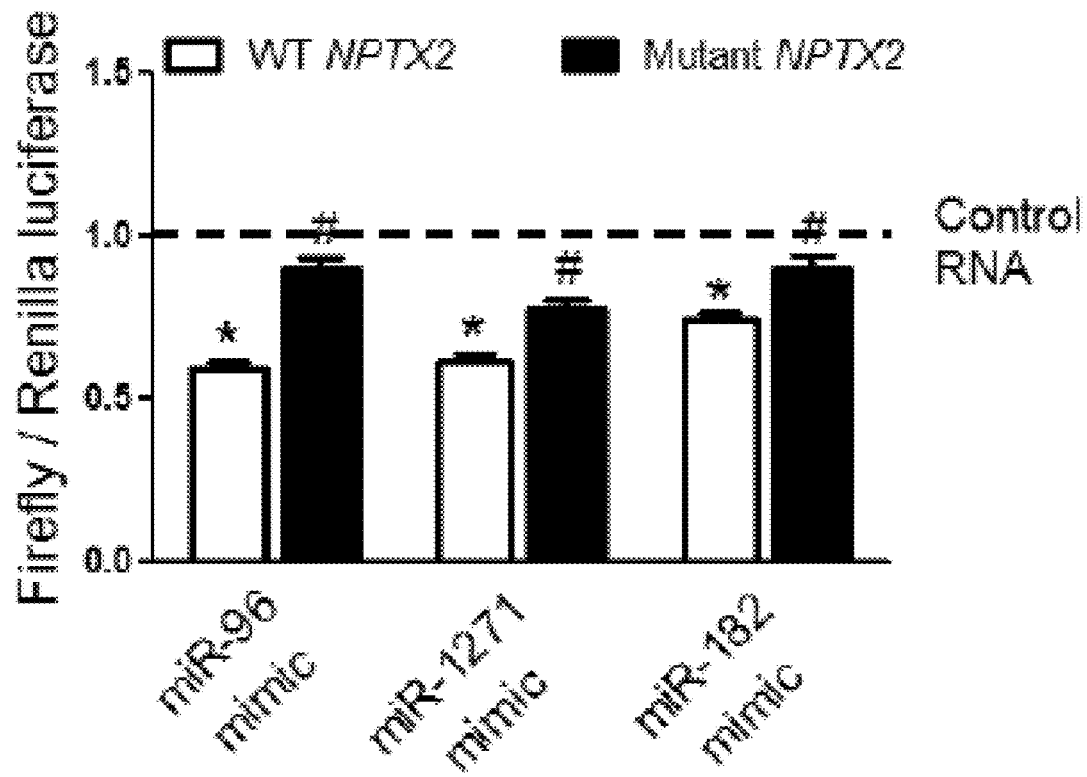

NPTX2 is reduced in AD brain. NPTX2 protein was assayed by western blot (WB) in human brain from cases with pathologically confirmed late onset Alzheimer's disease (AD) versus age-matched controls (FIG. 17A, 17B). NPTX2 was reduced in all assayed regions of AD forebrain. NPTX2 mRNA was also reduced (FIG. 17C). NPTX2 is co-functional with Neuronal Pentraxin family members Neuronal Pentraxin 1 (NPTX1; also termed NP1) and Neuronal Pentraxin receptor (NPTXR). However, NPTX1 (FIGS. 17A,17D) and NPTXR (not shown) were not reduced; nor were other IEGs including Arc and Egr-1 (FIG. 22A,22B). NPTX2 is not reduced in brain of subjects who were cognitively normal at death but whose brains exhibit pathological criteria typical of AD-dementia including Aβ plaque and tangles; termed asymptomatic AD (ASYMAD) or preAD (FIG. 17E,17F). These observations suggest an association of NPTX2 expression with cognitive performance in AD. NPTX2 protein and mRNA were also reduced in middle frontal gyrus of Down syndrome subjects aged 19 y/o to 46 y/o compared to age matched controls (FIG. 17G-17I) indicating that NPTX2 down-regulation occurs in neurological diseases in addition to AD. miRNA and NPTX-2 down regulation in human brain. We examined the mechanism of NPTX2 down-regulation in human AD brain and considered transcriptional dysregulation since NPTX2 mRNA is reduced. In pancreatic cancer cells NPTX2 transcription is regulated by methylation of flanking genomic sequences, however NPTX2 methylation assayed by pyrosequencing is low in human brain and not different between control and AD subjects (FIG. 23). Moreover, NPTX2 pre-mRNA expression is not different between control and AD subjects (FIG. 18A). This suggests NPTX2 transcription is maintained in AD and that reduced mRNA is consequent to reduced pre-mRNA processing (ex. splicing) or mRNA stability. Immediate early genes (IEGs) are targets of miRNA control, and TargetScan predicts several candidate miRNAs that target NPTX2 3' UTR (FIG. 18B). We determined that two of these (miR-182 and miR-1271) are increased in human AD brain in association with reduced NPTX2 mRNA (FIG. 18C-18E and FIG. 24). Neither has previously been reported increased in AD. Both miRs target the same sequence in NPTX2 3'UTR near the end of the ORF. miR-182 is expressed from an independent promoter (miRBASE) while miR-1271 is generated from an intron of human (but not mouse) ARL10 (ADP-ribosylation factor-like 10), which encodes an uncharacterized small GTP binding protein (miRBASE). Both the ARL10 intron (pri-miR-1271) and ARL10 mRNA are increased in prefrontal cortex of AD subjects (FIG. 18C). We confirmed in heterologous cells that miRs that target this sequence (including miR-96, a paralog of miR-1271 that is abundant in mouse) reduce expression of a luciferase fusion encoding NPTX2 3'UTR compared to a point mutant 3' UTR that prevents miR targeting (FIG. 25). miRs expressed in cultured mouse cortical neurons reduce NPTX2 protein expression (FIG. 18F-2I). miR-96 is most effective and additionally reduces NPTX2 mRNA but not pre-mRNA. These studies define parameters of NPTX2 dysregulation in AD and suggest a role for miR mechanisms.

Figure 19A:
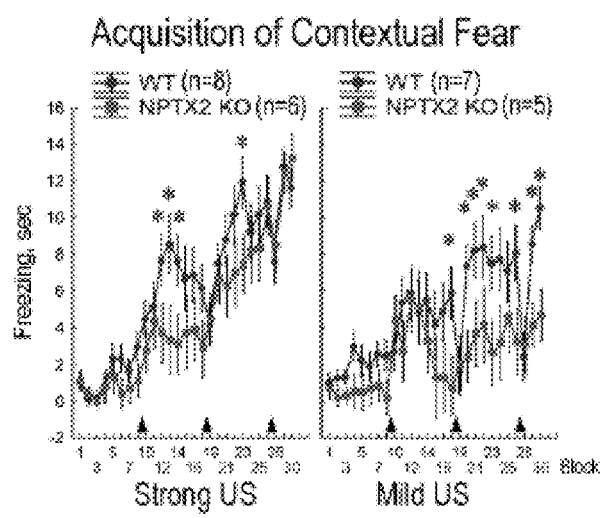
FIG. 19A-19I. Genetic deletion of NPTX2 results in deficits in acquisition of fear to context and elevated Aβ plaque.
Figure 19B:
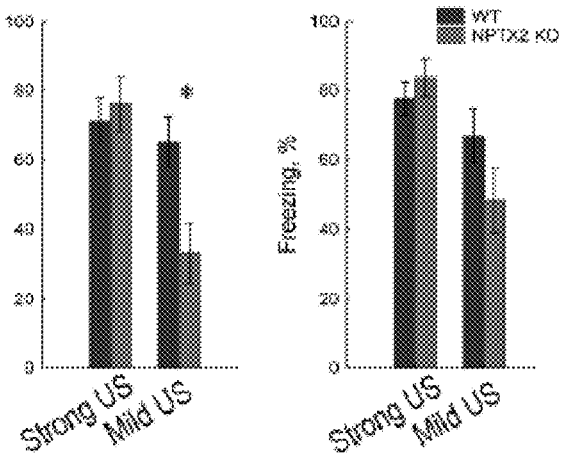
Figure 19C:
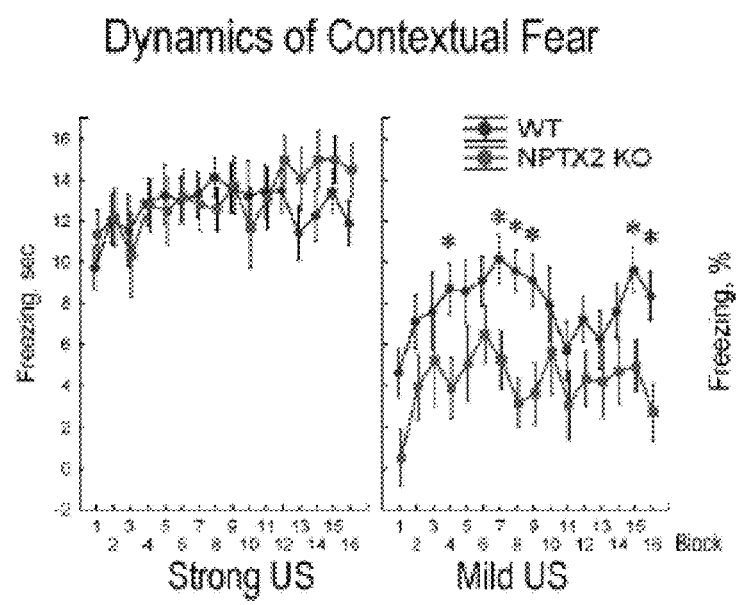
Figure 19D:
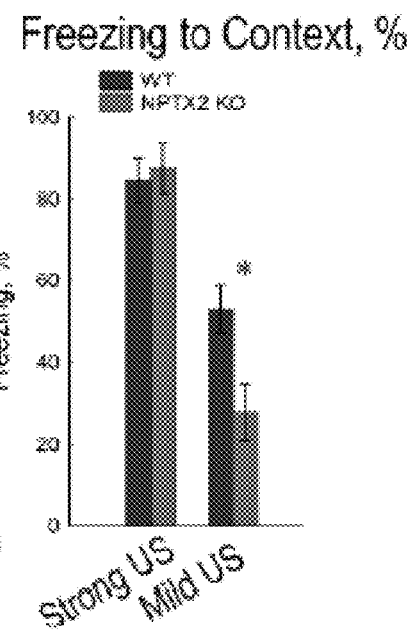
Figure 19E:
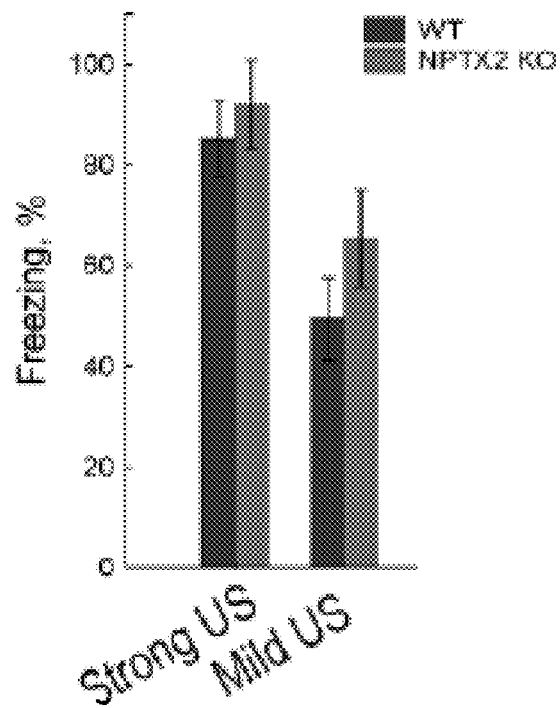
Figure 19F:
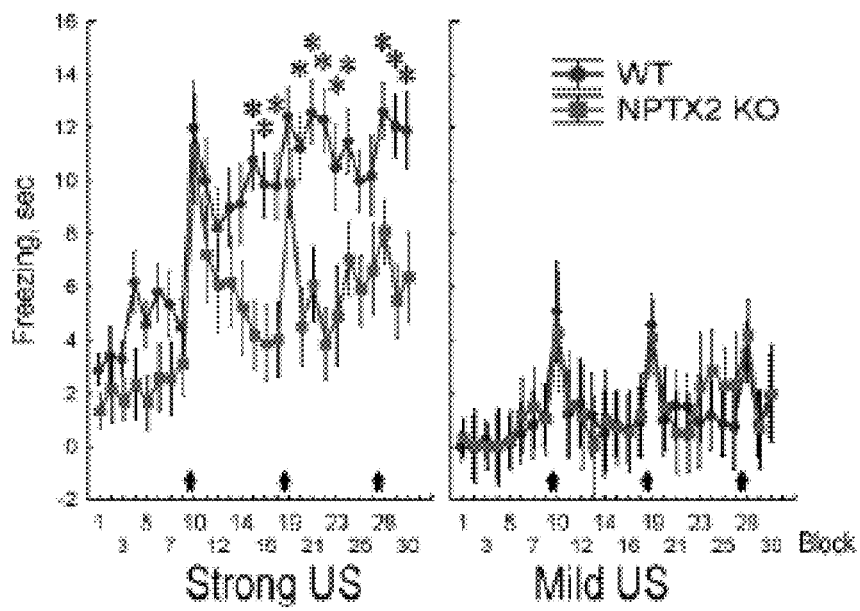
Figure 19G:
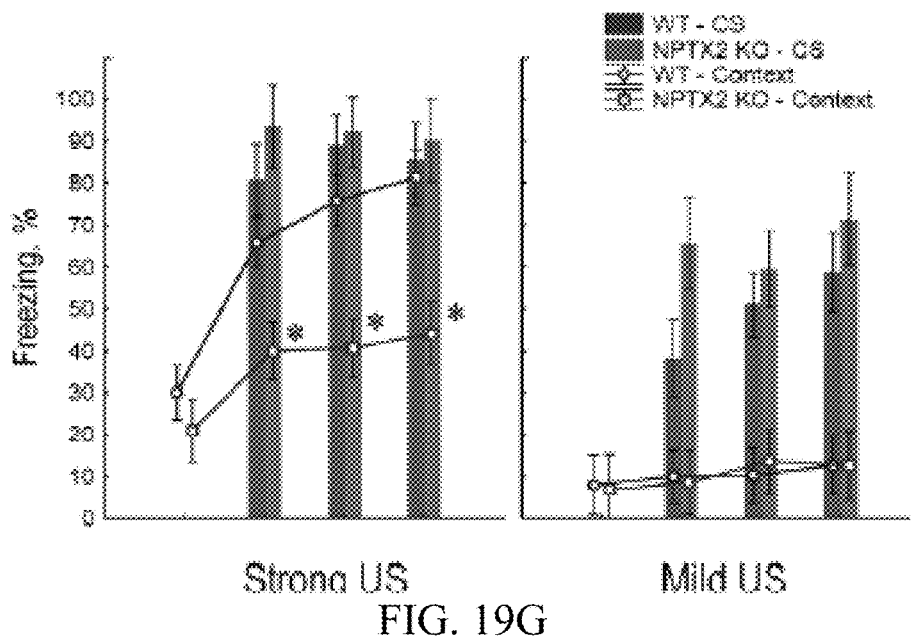

NPTX2 and hippocampus-dependent memory. We sought to identify phenotypes that might be attributable to down-regulation of NPTX2 in human AD/MCI. We first examined the hypothesized role in memory. NPTX2$^{-/-}$ mice have normal sensitivity in an array of tests assessing nociception and anxiety (FIG. 26) but show deficits in acquisition of fear to context as judged by development of the freezing response during intertrial intervals (FIG. 19A). This learning deficit is specific for context, not conditioning stimulus (CS; FIG. 19B), consistent with a requirement for the hippocampus in encoding contextual information but not discrete cues. When this deficit is overcome using an unconditioned stimulus (US) of higher intensity long-term memory for context and cued-memory are normal (FIG. 19C-19E). NPTX2$^{-/-}$ mice also exhibit a deficit in acquisition of second-order context conditioning that involves association of a learned source of danger (CS) with new context (FIG. 19F, 19G). Considering that NPTX2$^{-/-}$ mice are normal when tested in various multi-trial paradigms of gradual learning, their selective deficits in acquisition of contextual fear indicate that genetic deletion of NPTX2 deteriorates rapid encoding of hippocampus-dependent contextual memories. Such deficits would impede forming representations of events necessary for episodic memory, the deterioration of which is common as a presenting symptom in human AD. NPTX2 is abundant in the hippocampus and particularly in the trisynaptic pathway (DG-CA3-CA1) that is crucial for rapid learning of contextual information.

Figure 19H:
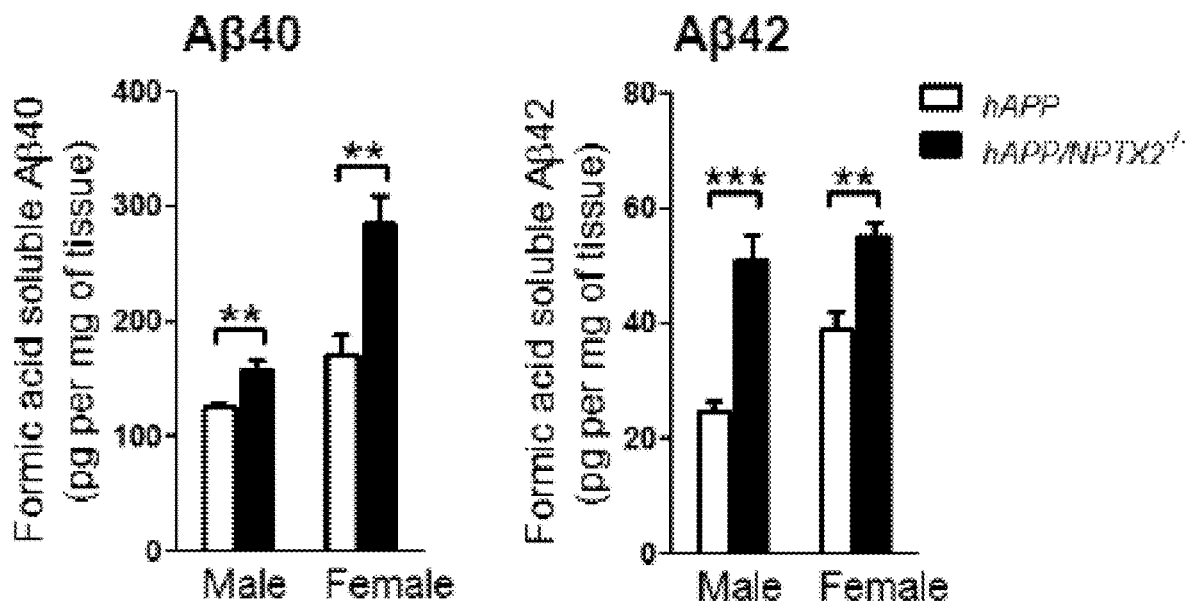
Figure 19I:
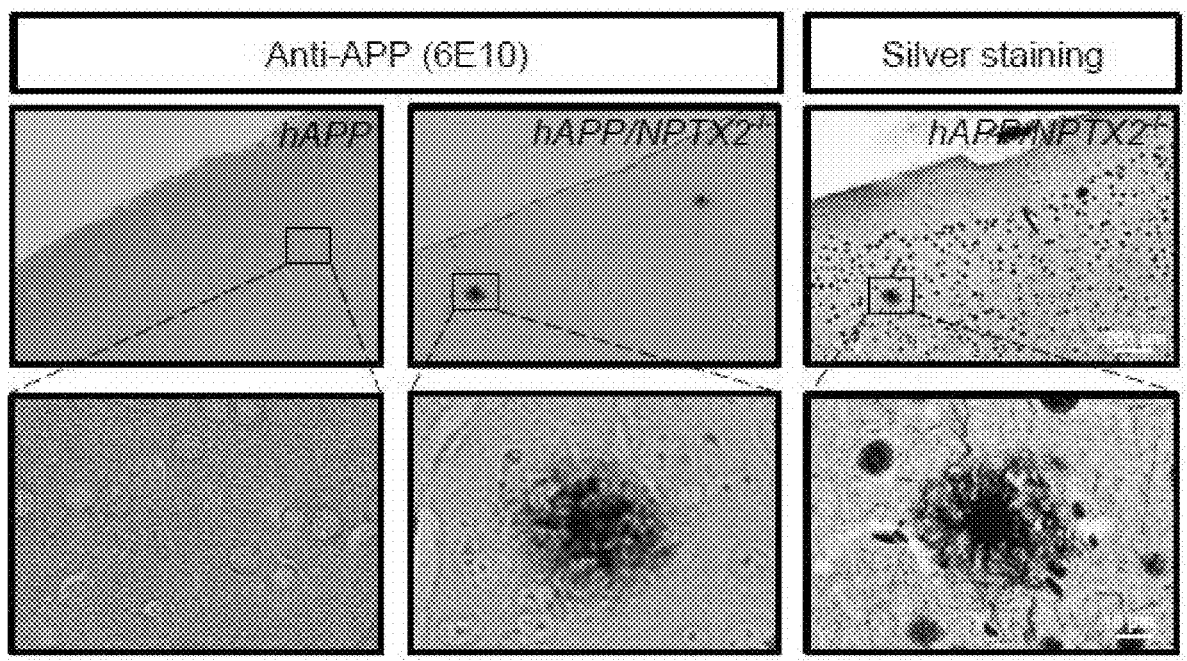

NPTX2 and Aβ amyloid. In its role as a mediator of homeostatic adaptation to activity, NPTX2 strengthens excitatory synapses to increase interneuron firing. NPTX2 mice show increased vulnerability to induced seizures and deficits of ocular dominance plasticity that are rescued by GABAA agonist. Since Aβ generation increases with neural activity, reduced NPTX2 in human AD brain could result in increased Aβ generation. To examine this prediction, we crossed NPTX2 mice with APPswe/PS1ΔE9 transgenic mice (here abbreviated hAPP) and examined brain at 3 months of age. Formic acid soluble Aβ40 and Aβ12 increased 30-50% in hAPP/NPTX2$^{-/-}$ male and female mice (FIG. 19H). As reported, hAPP mice did not show Aβ plaque at 3 months (0 of 7 males and 8 females), while plaque was evident in 4 of 6 male and 7 of 10 female hAPP/NPTX2$^{-/-}$ mice (FIG. 19I). These observations indicate that NPTX2 down-regulation can amplify pathological effects of familial mutations affecting Aβ generation and plaque formation.

Figure 20A:
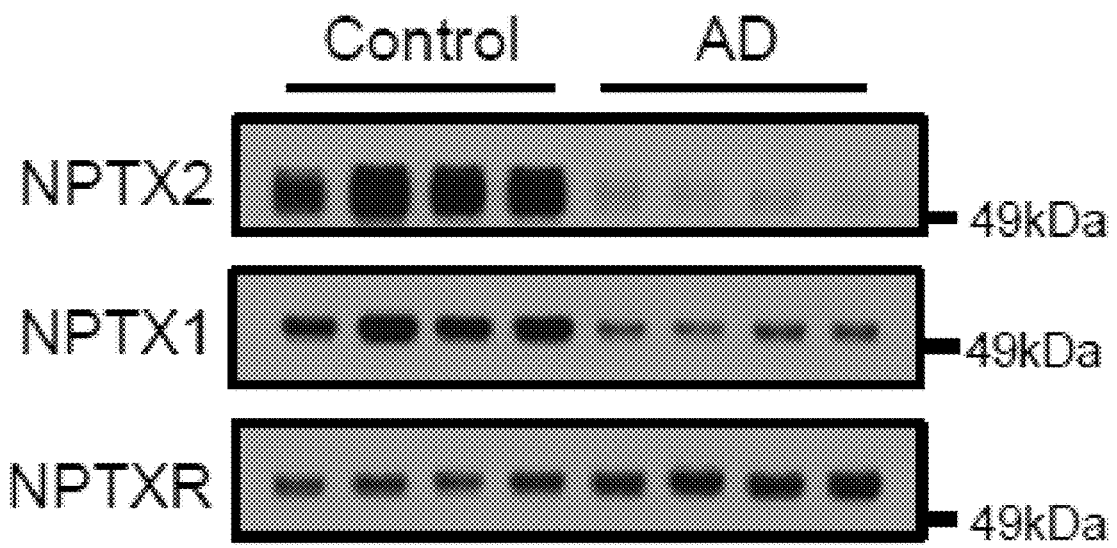
FIG. 20A-20G. NPTX levels are reduced in CSF from individuals with clinical diagnosed AD.
Figure 20B:
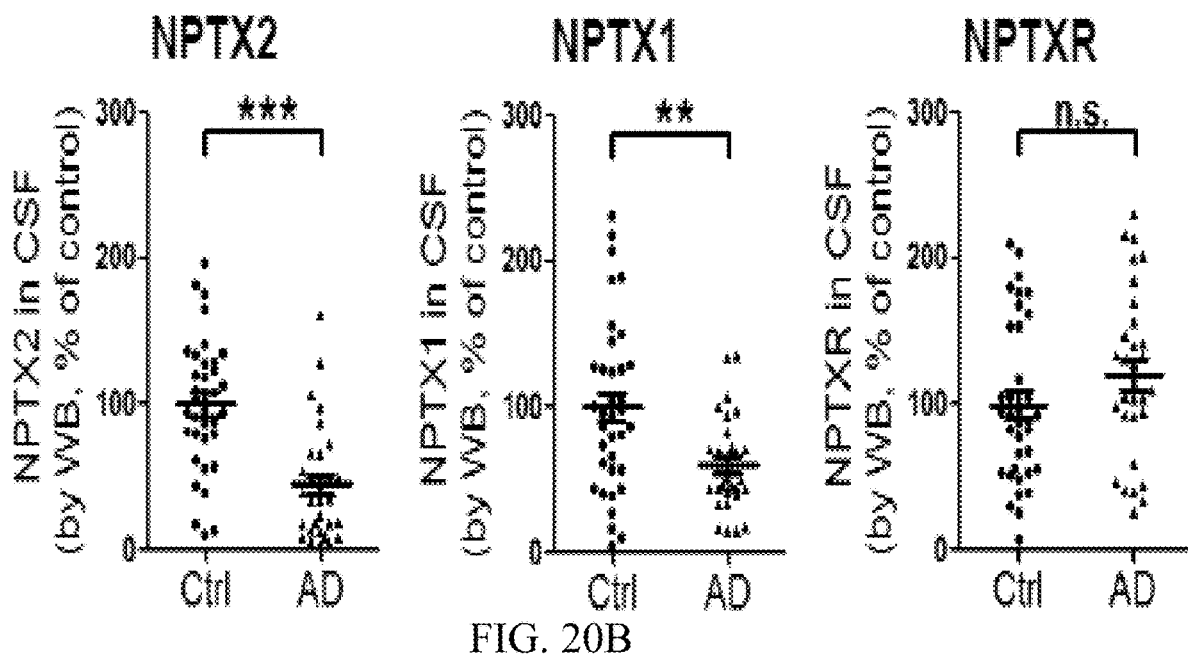
Figure 20C:
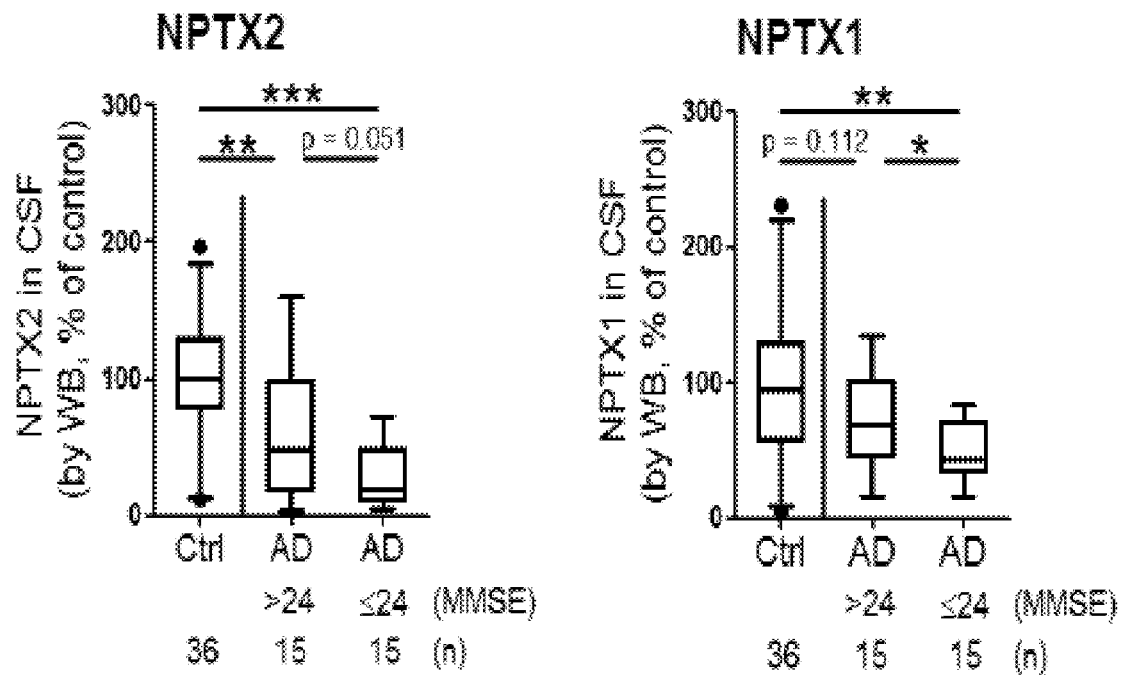
Figure 20D:
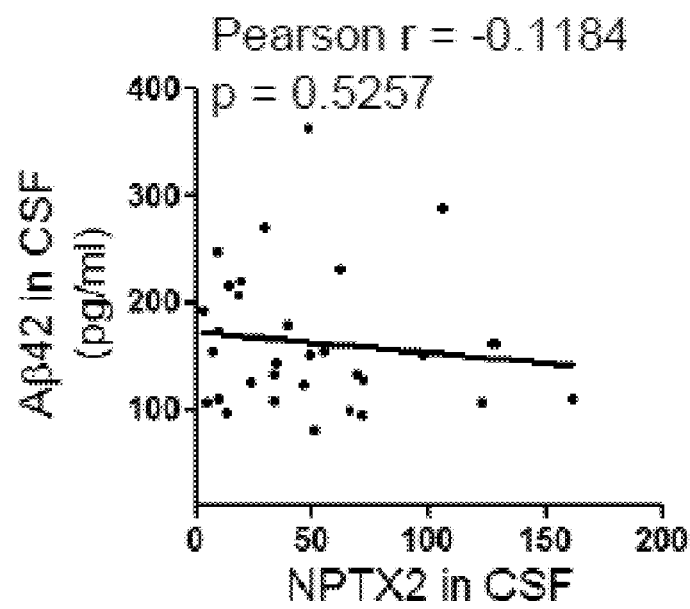
Figure 27A:
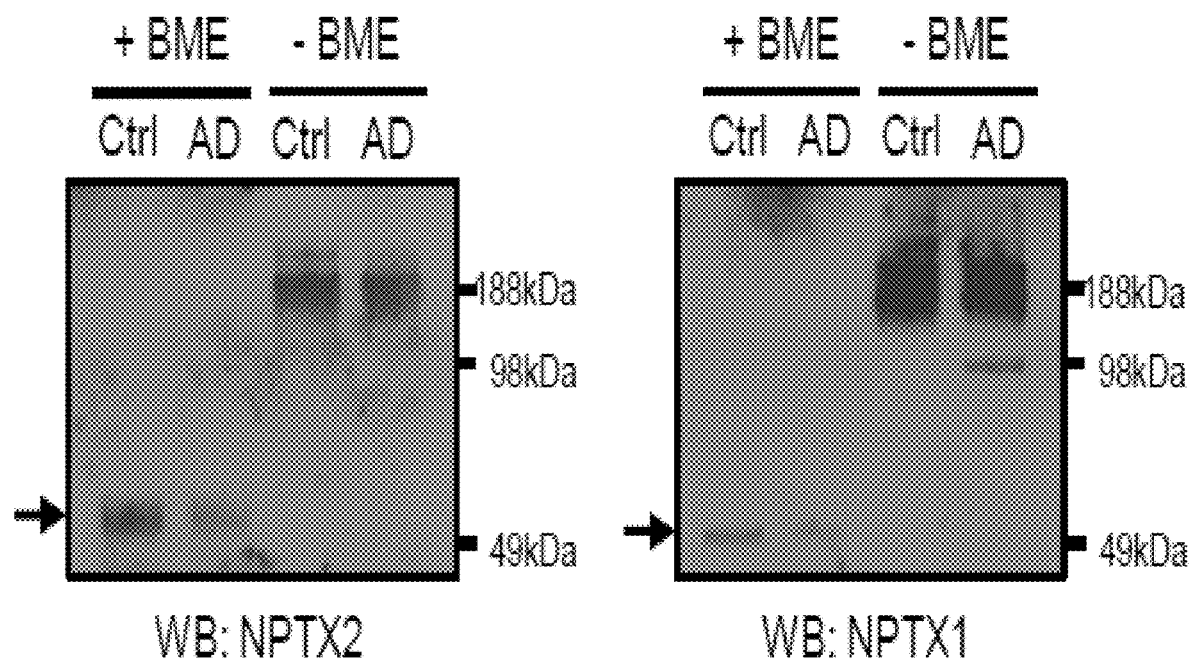
FIG. 27A-27B. Detection of NPTX2 and NPTX1 in human lumbar CSF.
Figure 27B:
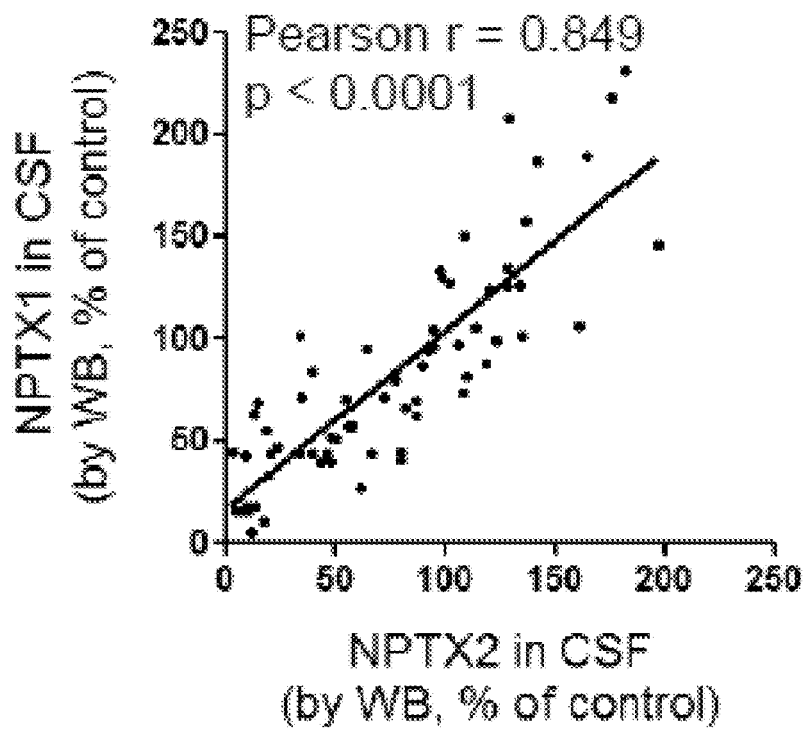
Figure 28A:
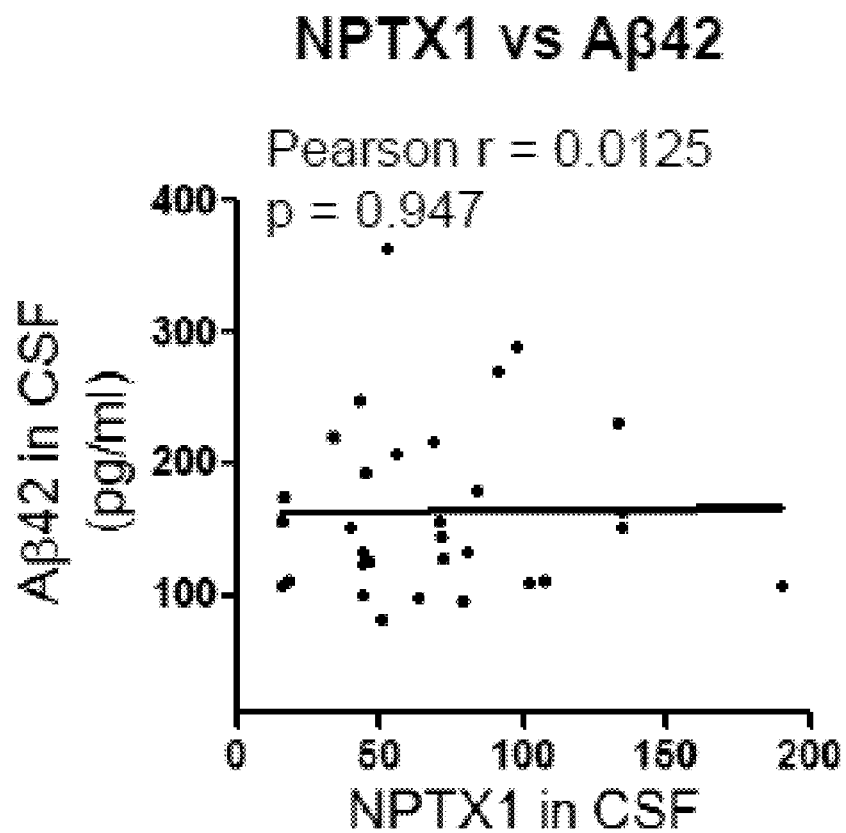
FIG. 28A-28E. Correlation between CSF NPTX and other known CSF biomarkers in AD patients.
Figure 28B:
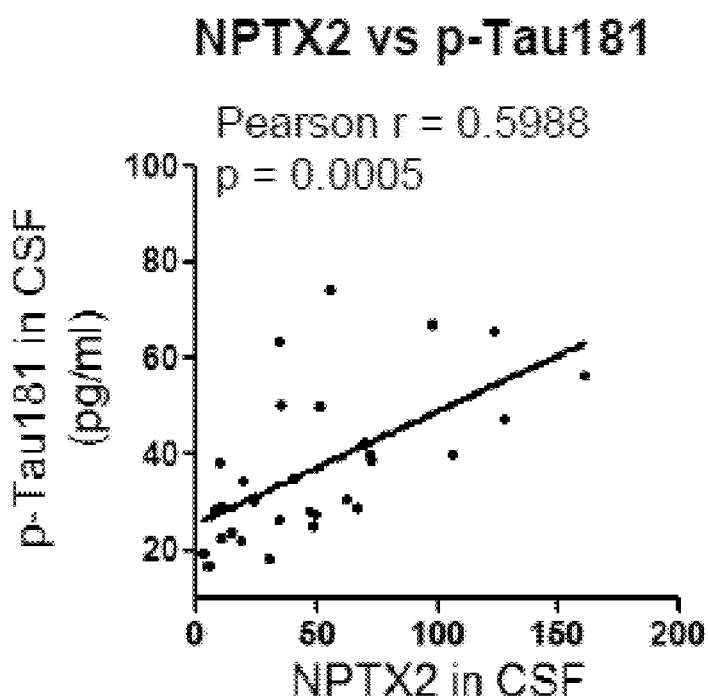
Figure 28C:
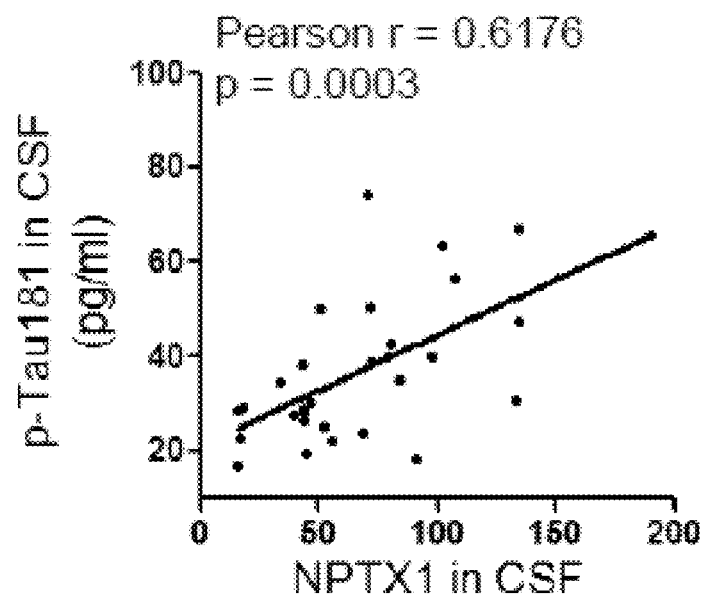
Figure 28D:
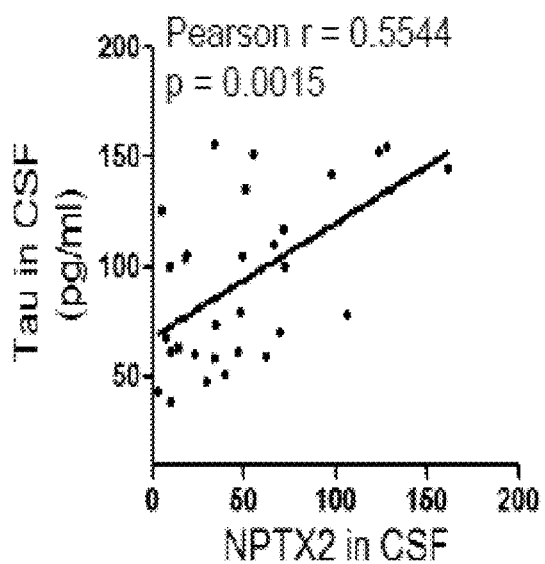
Figure 28E:
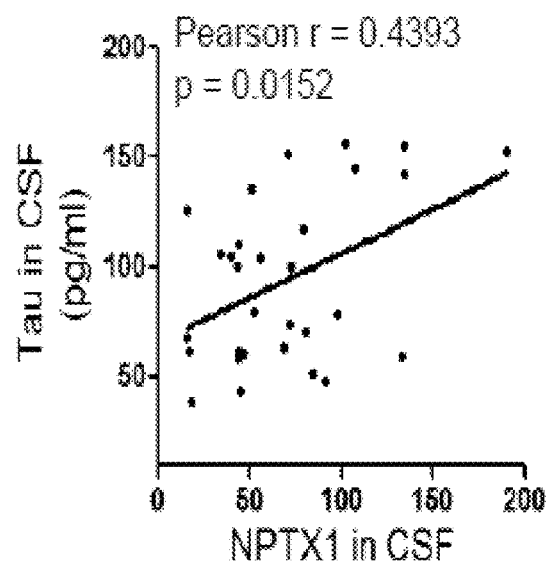
Figure 29A:
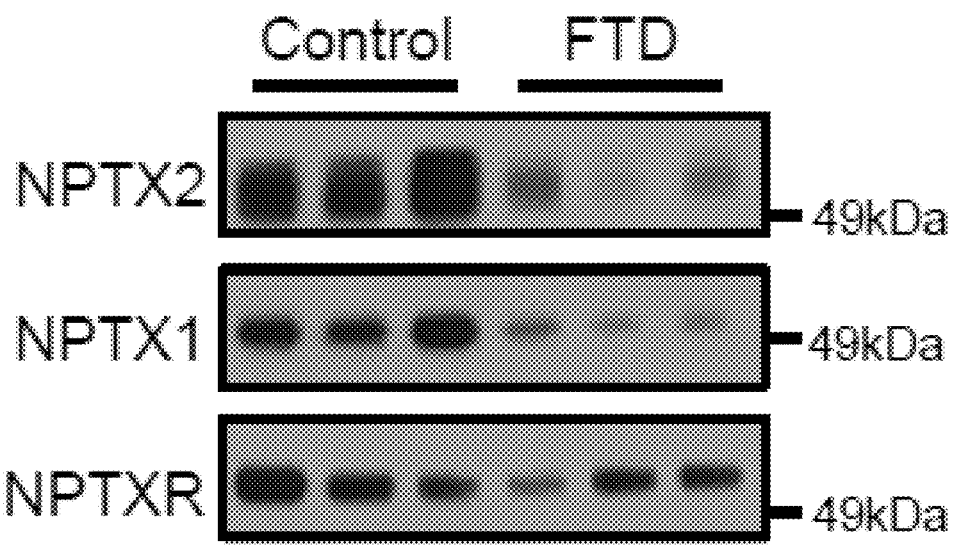
FIG. 29A-29D. NPTX levels are reduced in CSF from individuals with non-AD dementia.
Figure 29B:
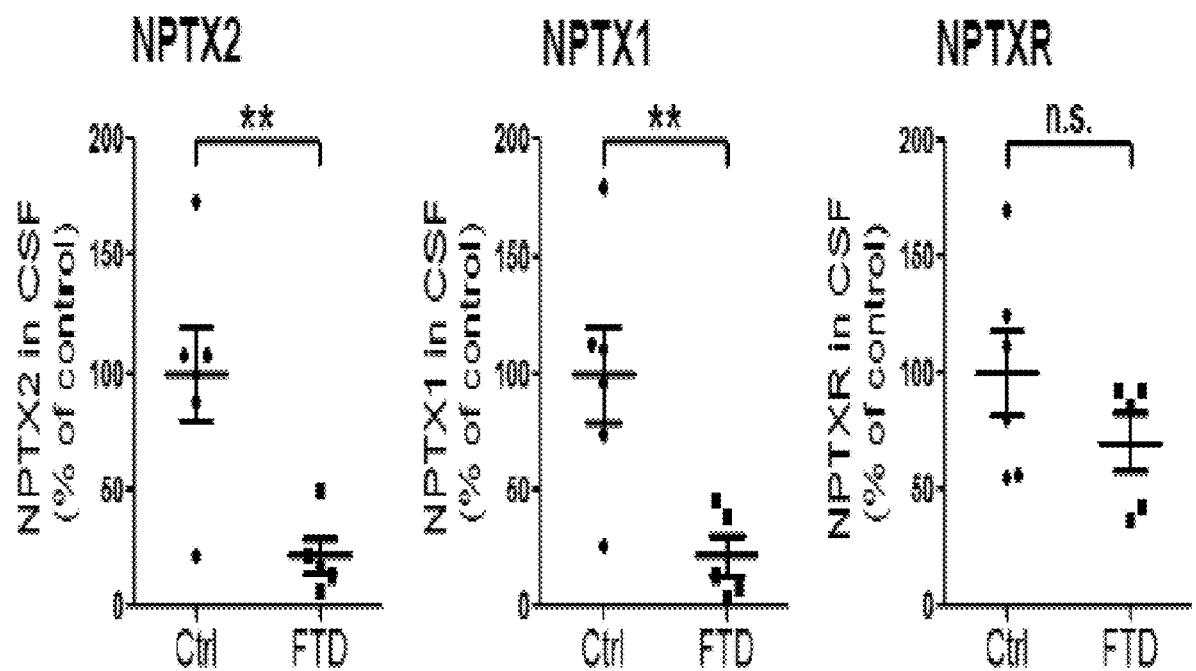
Figure 29C:
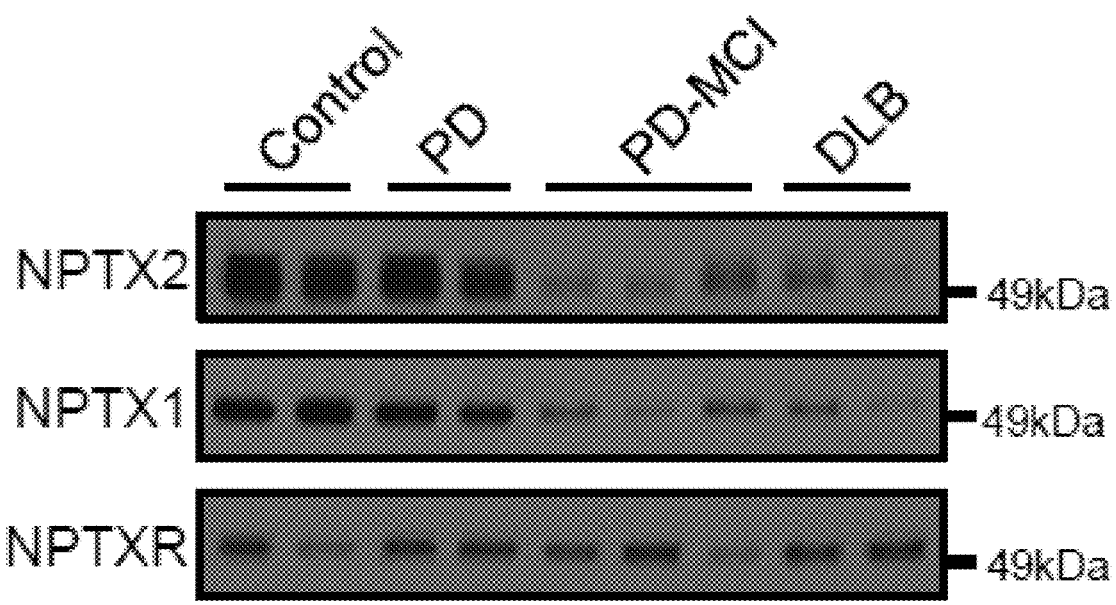
Figure 29D:
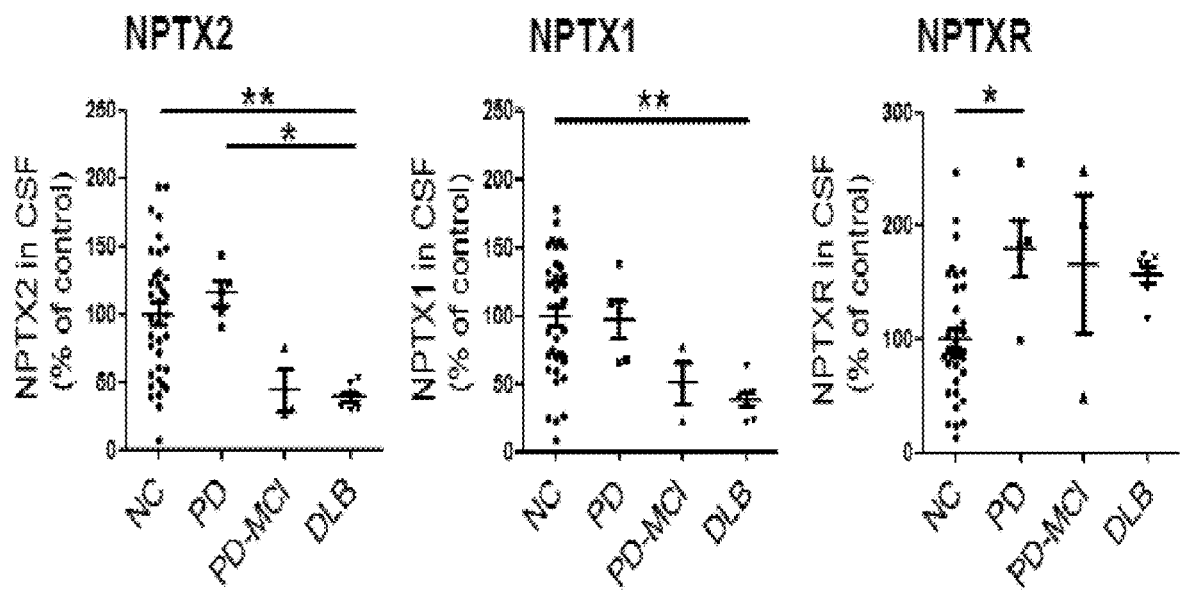

NPTX2 provides a CSF biomarker of cognitive failure in human AD and MCI. Consistent with their expression on the cell surface, NPTX1/2/R are detected in lumbar CSF of human subjects (FIG. 27A). NPTXR levels were not significantly different between AD and age-matched control patients (FIG. 20A, 20B). By contrast, NPTX1 and NPTX2 were significantly reduced in AD patients, and levels closely correlated within samples (FIG. 27B). The reduction of NPTX2 in CSF is consistent with global reduction in AD brain. Reduction of NPTX1 in CSF despite normal levels in AD brain is consistent with its CSF origin from a subset of excitatory synapses where it is co-functional with NPTX2. Levels of NPTX1 and NPTX2 correlate with cognitive performance assessed by mini mental status exam (MMSE) in AD (FIG. 20C). Aβ42 assayed in these samples did not correlate with NPTX1/2 (FIG. 20D and FIG. 28) suggesting CSF levels of NPTX and Aβ42 peptides assay different aspects of AD pathophysiology. We also detect reduced NPTX2 in CSF of a small group of patients with dementia resulting from Frontotemporal Dementia (FTD) and Dementia with Lewy body (DLB) (FIG. 29).

Figure 20E:
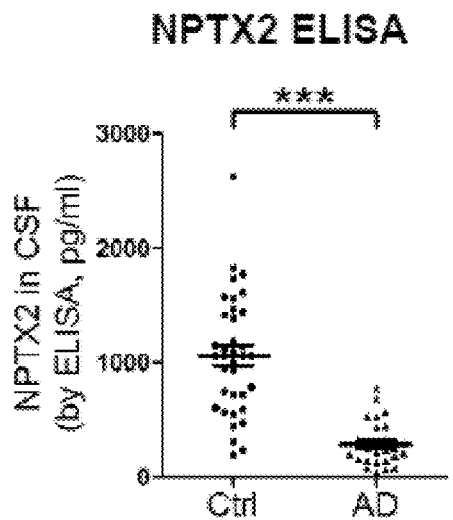
Figure 20F:
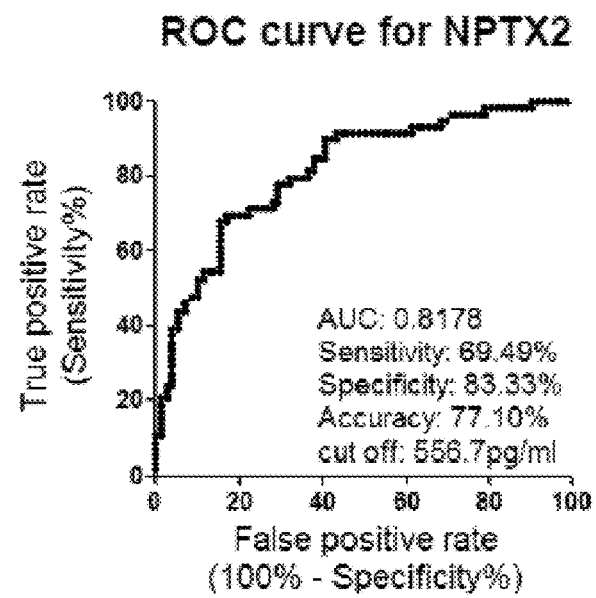
Figure 20G:
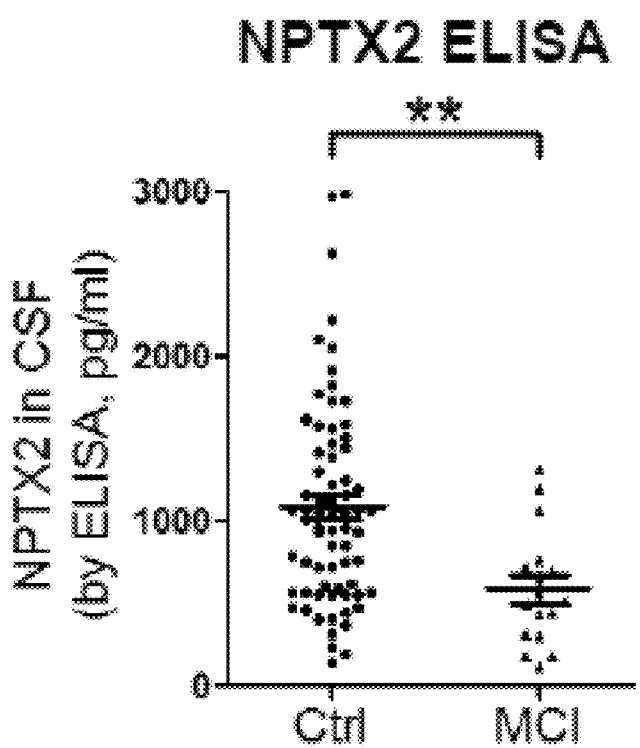
Figure 21:
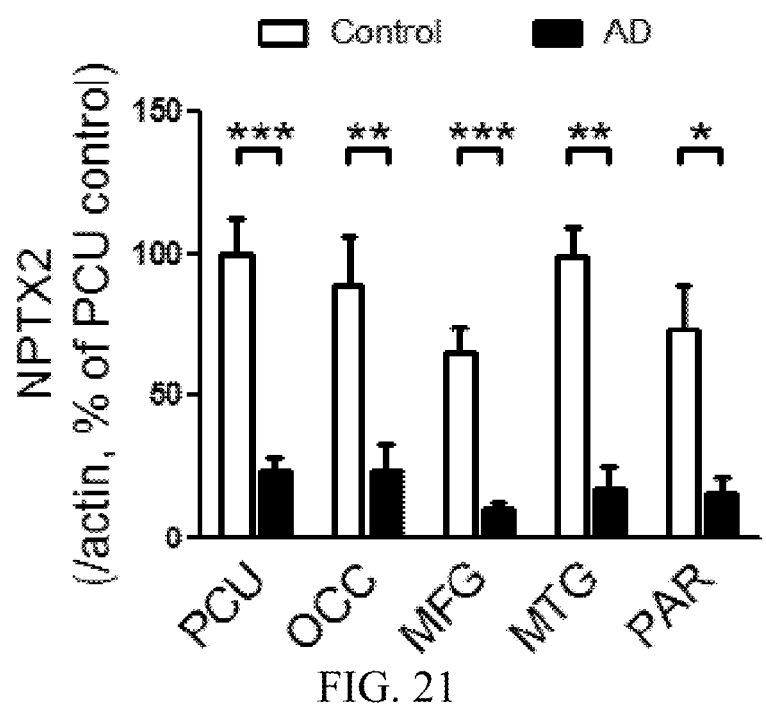
FIG. 21. Relative NPTX2 expression in different brain regions of control and AD subjects. Quantification of relative NPTX2 levels in FIG. 17A from different brain regions, including precuneus (PCU), occipital gyrus (OCC), middle frontal gyms (MFG), middle temporal gyms (MTG) and parietal gyms (PAR) in controls and AD subjects. NPTX2 is down regulated in all assayed brain regions of AD individuals when actin was served as loading control. The average of PCU control group was set to 100%. FPC: n=7 for control and n=8 for AD; PCU: n=15 for control and n=19 for AD; OCC: n=7 for control and n=7 for AD; MFG: n=6 for control and n=11 for AD; MTG: n=4 for control and n=5 for AD; PAR: n=5 for control and n=5 for AD. *p<0.05, p<0.01, *p<0.001 by two-tailed t test. Data represent mean±SEM.
Figure 30A:
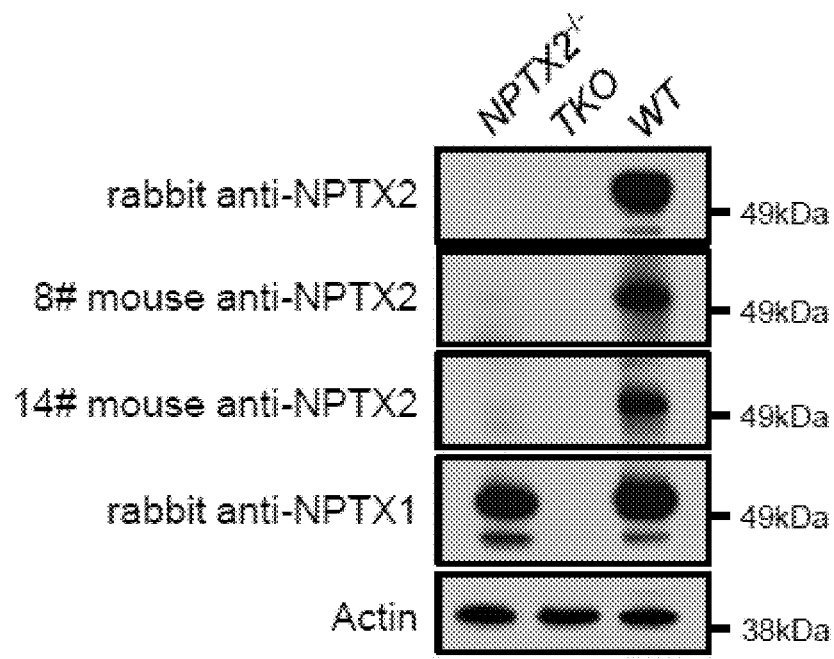
FIG. 30A-30C. Establishment of NPTX2 ELISA assay to quantitate NPTX2 level in CSF.
Figure 30B:
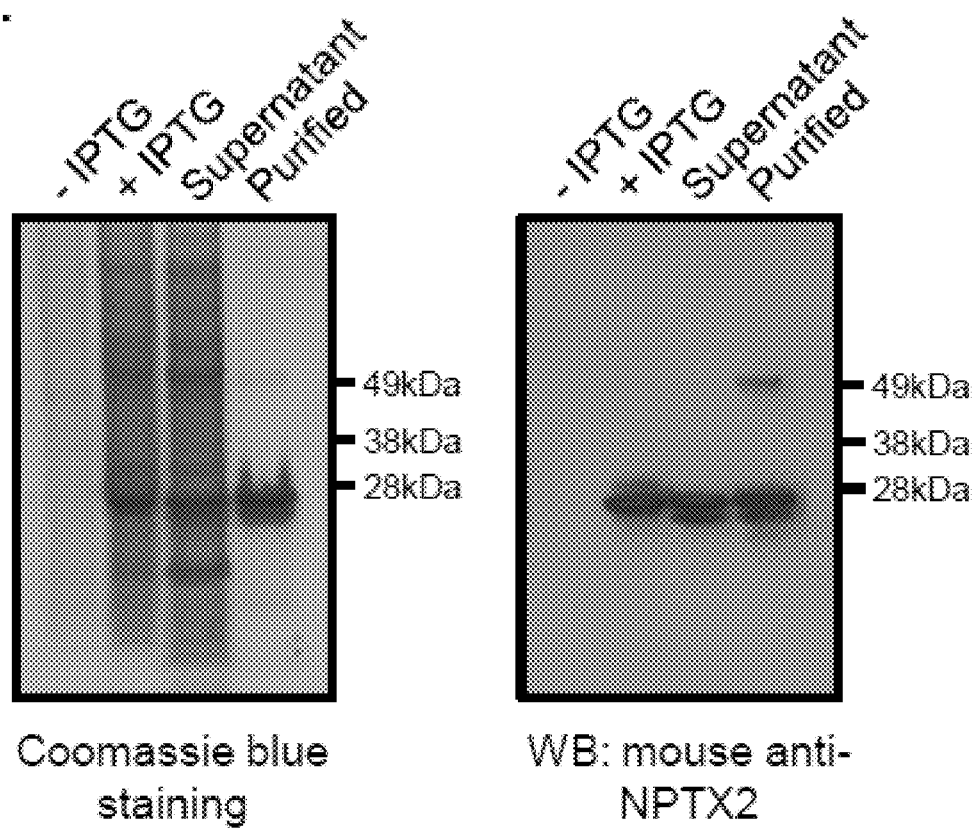
Figure 30C:
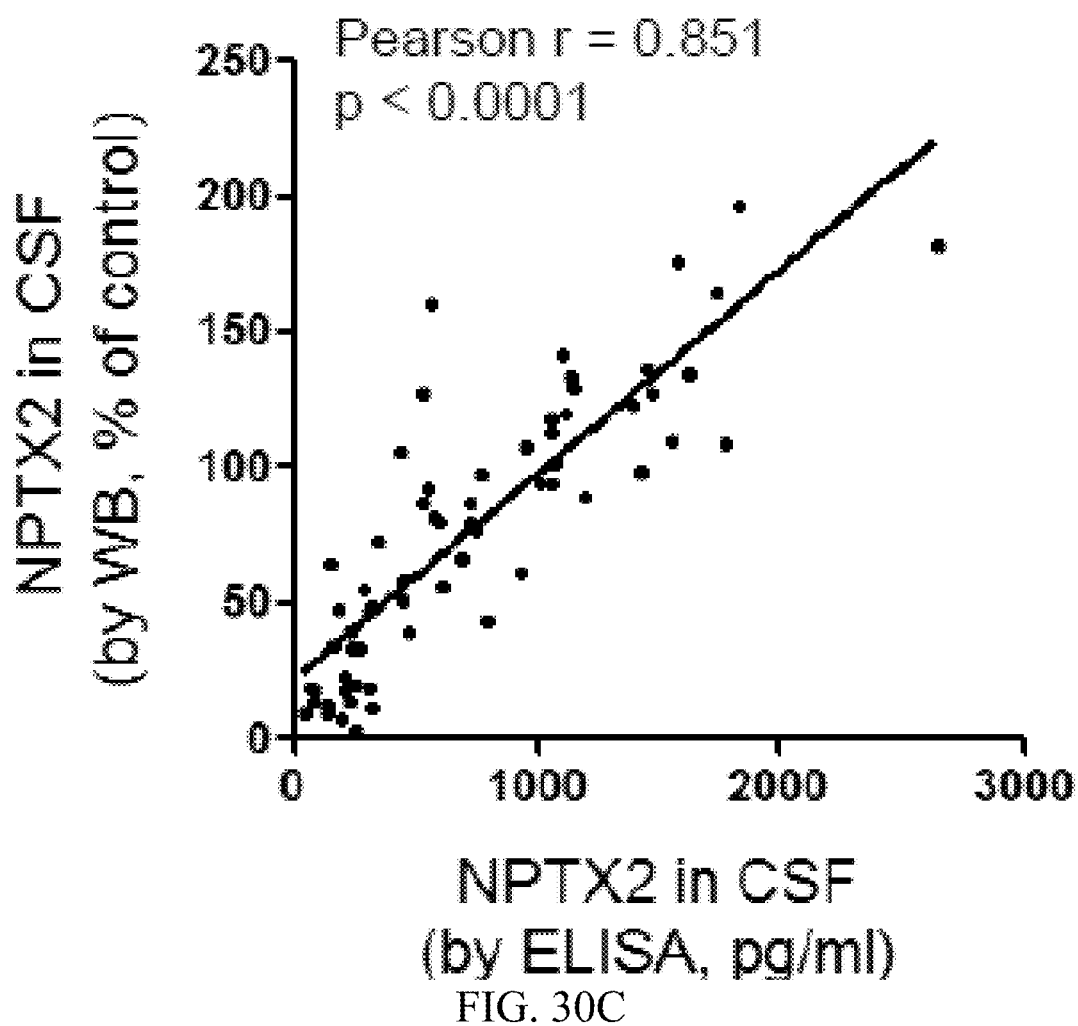
Figure 31A:
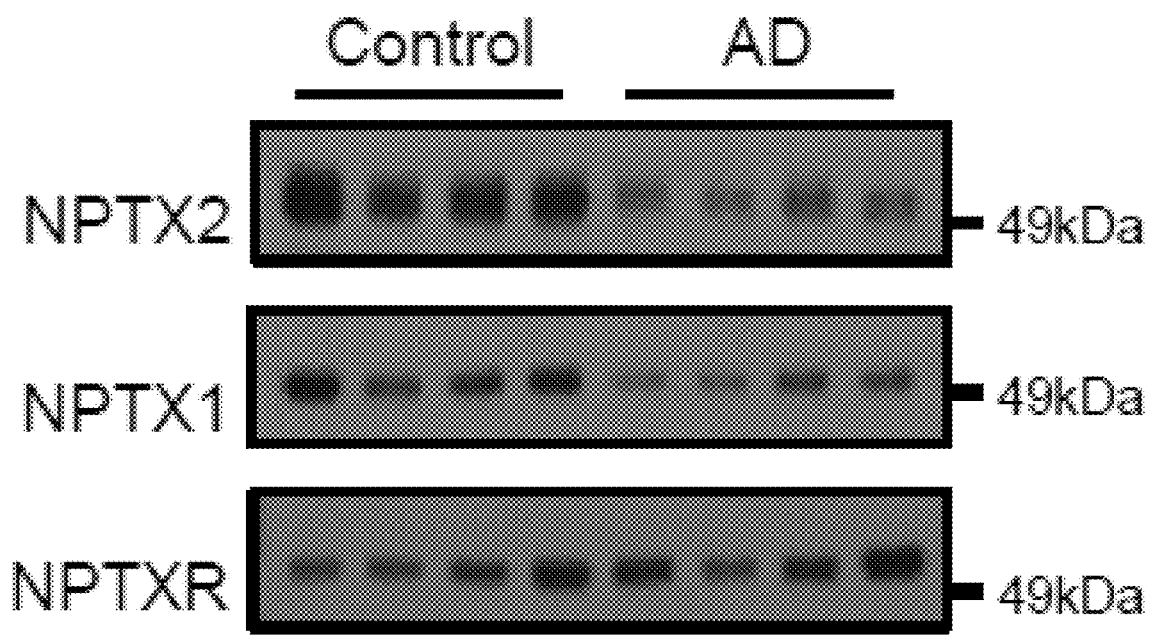
FIG. 31A-31E. NPTX levels are reduced in CSF from individuals with clinical diagnosed AD.
Figure 31B:
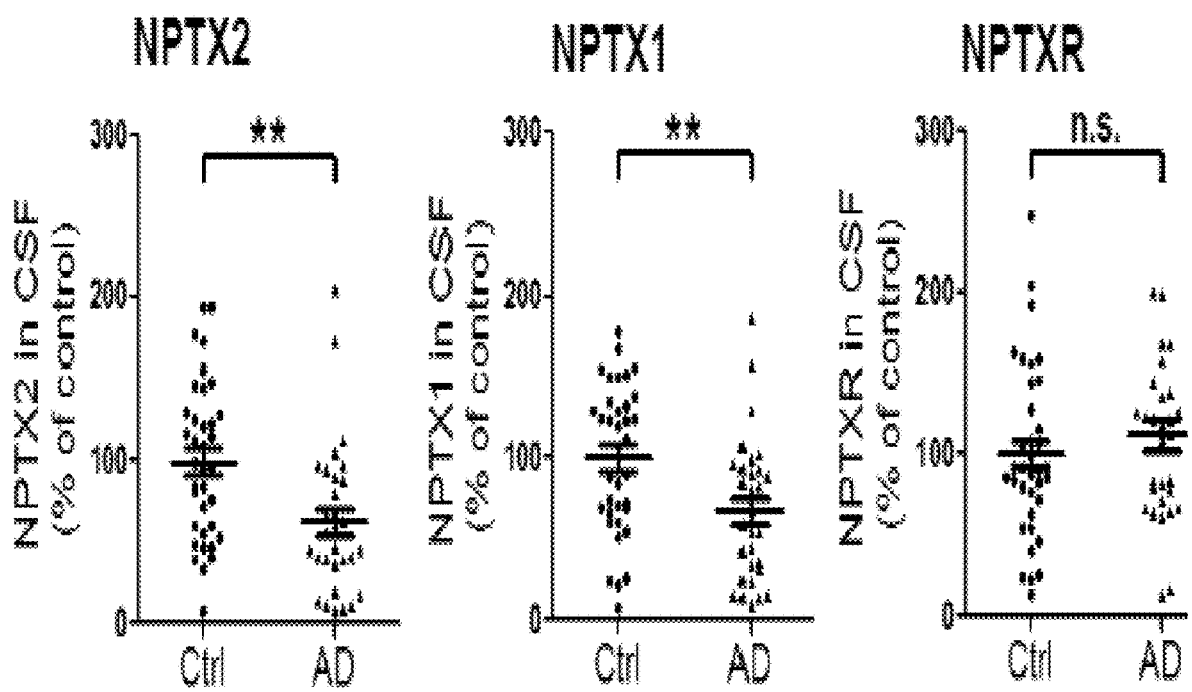
Figure 31C:
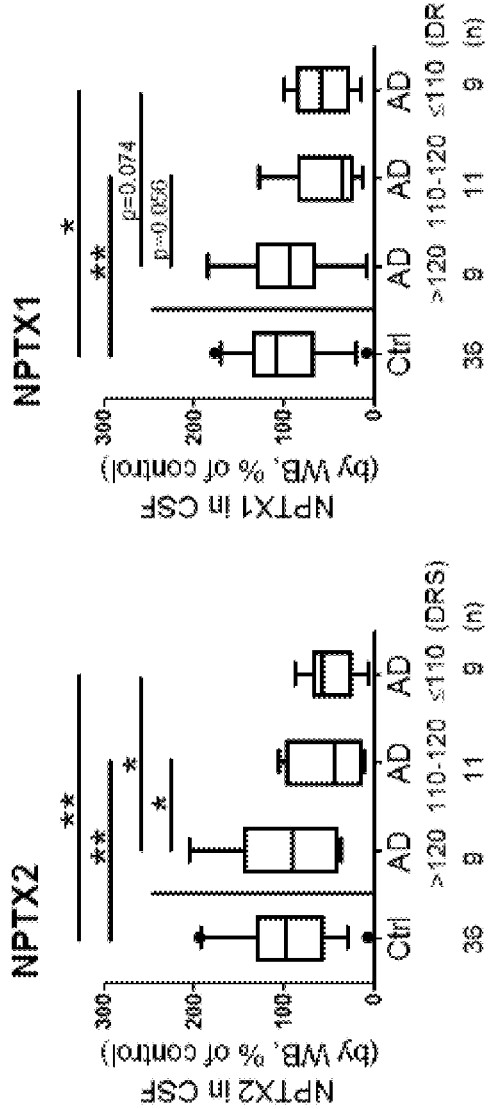
Figure 31E:
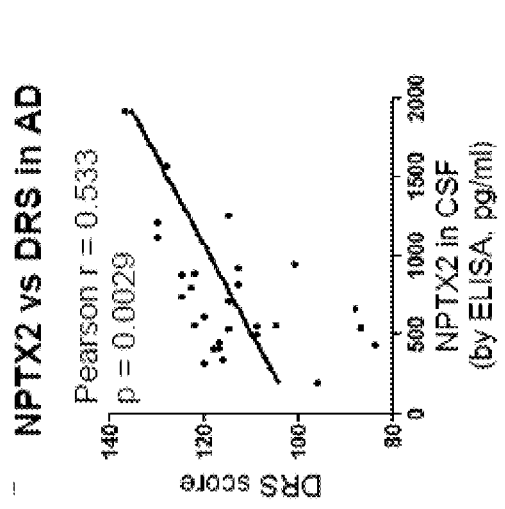
Figure 31D:
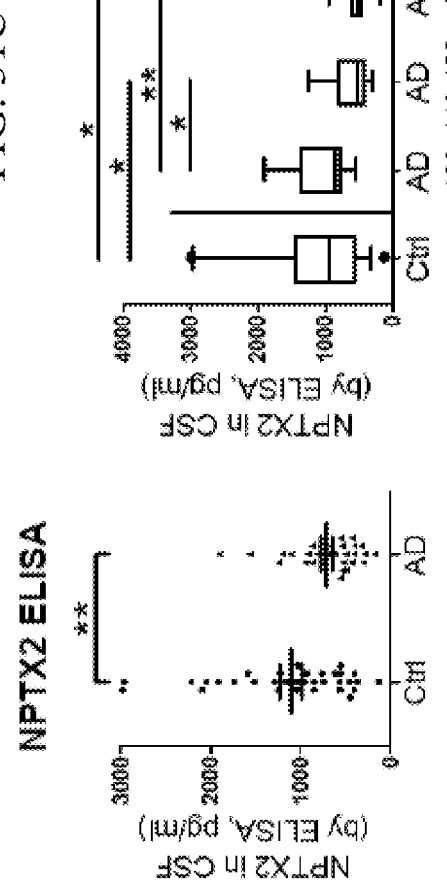
Figures 32A, 32B, 32C:
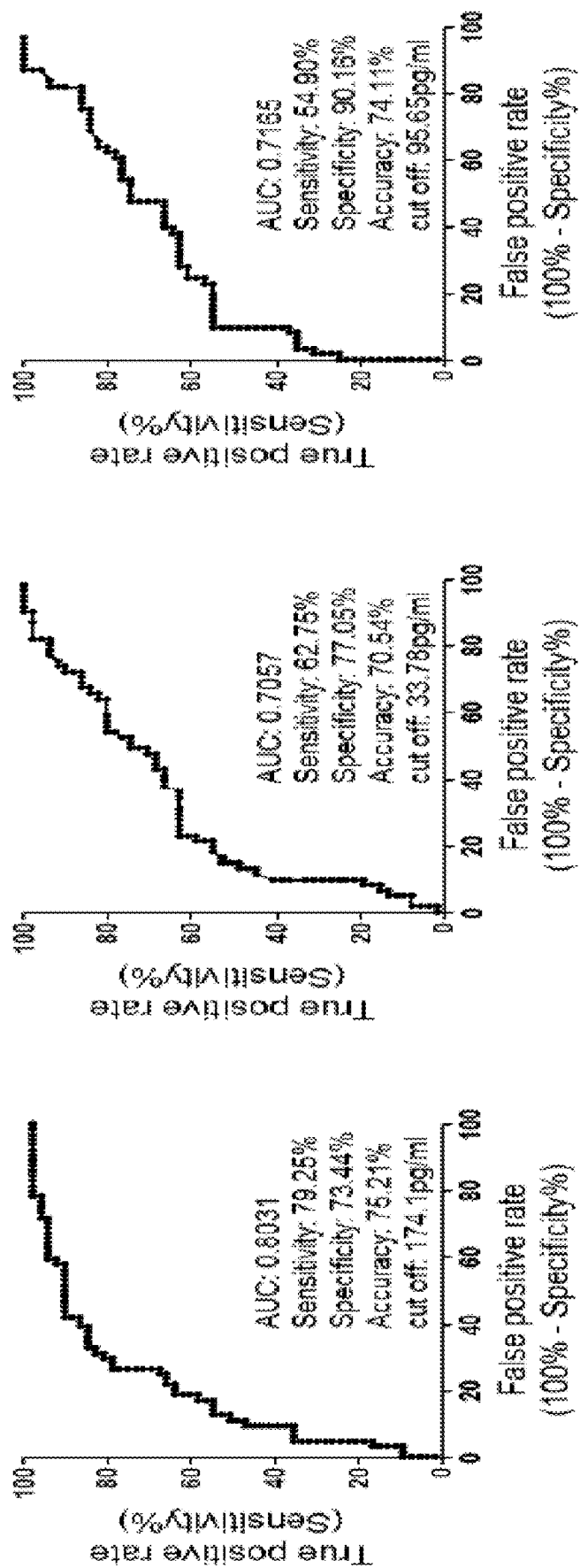
FIG. 32A-32C. Receiver operating characteristic (ROC) curve analysis of CSF Aβ42 (32A), p-Tau181 (32B) and Tau (32C) as diagnostic biomarkers for AD. "Cut-off" point was determined by maximizing Youden index value. n=64 for control, n=53 for AD.

We developed an ELISA to quantitate NPTX2 protein in CSF (FIG. 10) and confirmed close correlation with WB detection (FIG. 30C). The median NPTX2 level in control CSF was 1067 pg/ml compared to 295 pg/ml in AD (FIG. 20E). Consistent with current standards to document a new biomarker we screened a second independent set of patient CSF samples by WB and ELISA and confirmed consistency of levels in controls and reduction of NPTX2 in AD (FIG. 31). Detailed cognitive data for the second set of subjects revealed NPTX2 reduction in subjects with Dementia Rating Scale (DRS)<120 (FIG. 31C). DRS scores correlated with NPTX2 levels in AD subjects (FIG. 31E). The diagnostic value of NPTX2 in distinguishing control from AD subjects was comparable to Aβ42, tau or p-tau (FIG. 20F and FIG. 32). ELISA analysis of samples from patients with MCI demonstrated reduction of NPTX2 compared to controls (FIG. 20G).

Discussion

AD pathogenesis prominently impacts mechanisms of de novo protein synthesis-dependent memory suggesting a new model to understand cognitive dysfunction. The Arc mechanism reduces synaptic weights and includes a feed forward pathway for Aβ activation of mGluR5. Accordingly, dysregulation of Aβ generation from diverse causes can corrupt this pathway. The NPTX2 mechanism is disrupted as a consequence of reduced mRNA expression, possibly due to miRNAs. Arc and NPTX2 pathways are understood to normally act in concert to store information as their primary function, but their effect to reduce neural activity also contributes non-redundant mechanisms for homeostatic control. In absence of the NPTX2 neurons fail to achieve excitatory homeostasis resulting in a persistent drive on other homeostatic mechanisms, including Arc. Thus, down-regulation of NPTX2 corrupts an important mechanism of information storage and accentuates activity-dependent mechanisms that enhance Aβ generation. As indirect support of this model, human subjects experiencing amnestic mild cognitive impairment respond to GABAA agonist with reversal of elevated hippocampal activity and improved memory function. This understanding of NPTX2 rationalizes several clinical aspects of AD including increased vulnerability to seizures, persistence of aberrant activity, and early onset episodic memory loss.

Figure 33A:
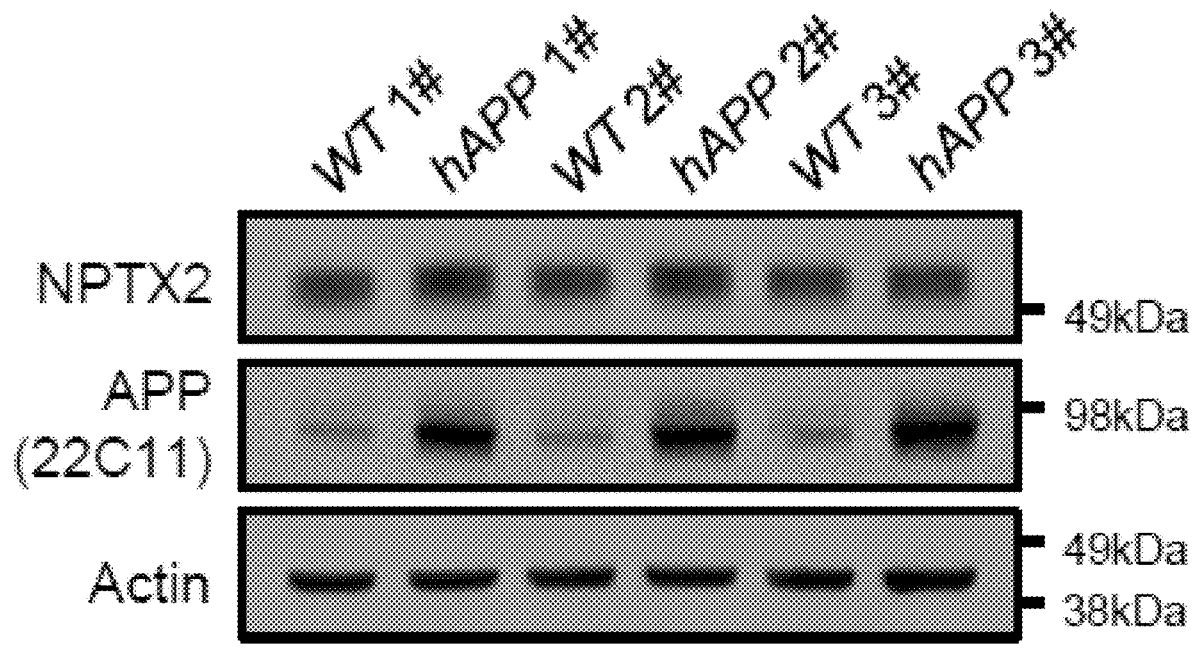
FIG. 33. NPTX2 expression in AD mouse model. NPTX2 expression in cortex is not significantly changed in 6 month-old APPswe/PS1ΔE9 (here abbreviated hAPP) mice when compared with wildtype (WT). n=6. Two-tailed t-test. Data represent mean±SEM.
Figure 33B:
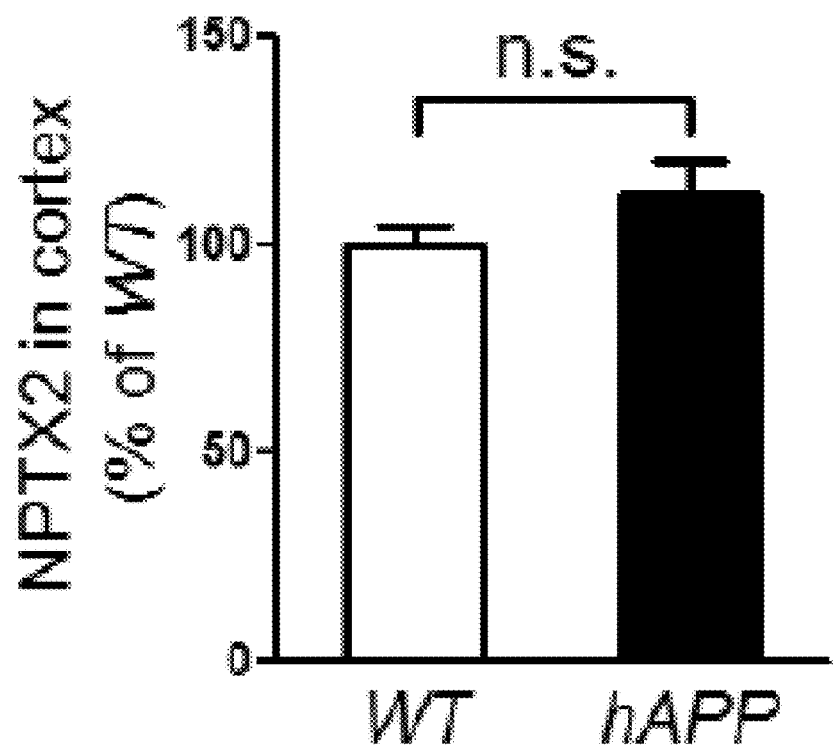
Figure 34:
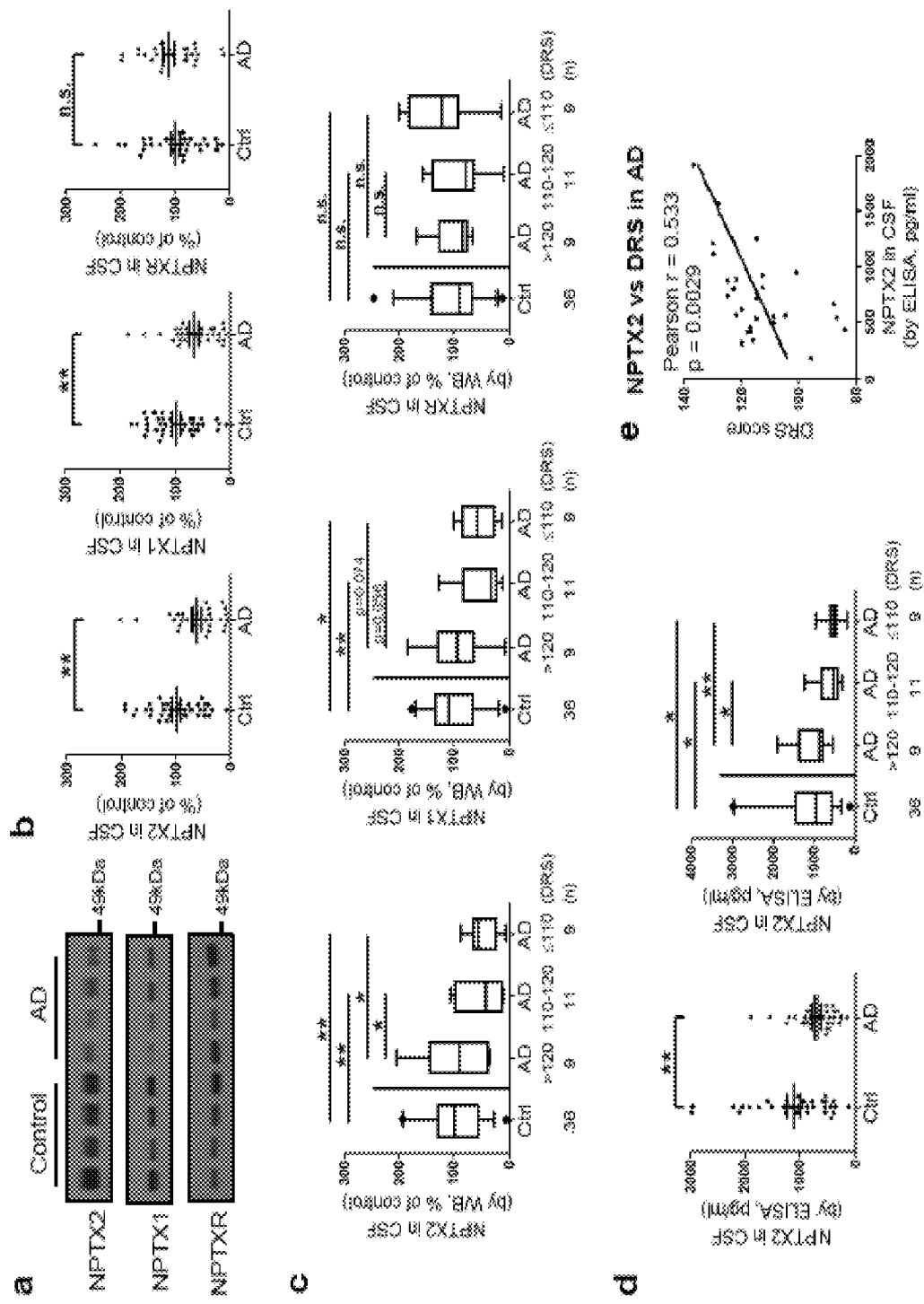
FIG. 34A-34E. NPTX levels are reduced in CSF from individuals with clinical diagnosed AD.

The role of miRs in NPTX2 downregulation remains hypothetical but compelling. miR-182 expression is induced by β catenin and in cancer cells contributes to invasiveness by down-regulation of RECK, an inhibitor of extracellular metalloproteases. miR-1271 is human specific and targets multiple synaptic genes including GABA synaptic protein gephyrin. ARL10 protein is predicted to play a role in vesicular trafficking similar to ARFs that are implicated in trafficking synaptic proteins including BACE1 and APOE receptor LRP1. miRs have been successfully targeted in the CNS for therapeutics. Relevant animal models will be important to establish; NPTX2 is not down-regulated in the hAPP mouse (FIG. 33).

NPTX2 down-regulation is not limited to AD but is consistently associated with cognitive dysfunction. Down-regulation in DS is consistent with the present model since APP is a triploid gene. NPTX2 down-regulation is not restricted to aged DS individuals suggesting it represents a developmental adaptation contributing to mental impairment. DLB and FTD do not exhibit prominent amyloid pathology, but loss of inhibitory circuit adaptation may nevertheless contribute to cognitive failure. This initial survey suggests NPTX2 expression is especially vulnerability in diseases that impact human cognition. The ability to assay NPTX2 in CSF provides an opportunity to define clinical associations and potential therapeutic responses in AD and other neuropsychiatric diseases.

We claim:

1. A kit comprising: (a) an antibody that specifically binds NPTX2, wherein the NPTX2 antibody has a heavy chain comprising SEQ ID NO: 28 and a light chain comprising SEQ ID NO: 29, or a heavy chain comprising SEQ ID NO: 30 and a light chain comprising SEQ ID NO: 31; (b) an agent for reducing heterocomplexes comprising NPTX1 and NPTX2 present in a biological sample obtained from a patient into NPTX1 and NPTX2 monomers; and (c) an agent for covalently modifying thiol groups of the NPTX1 and NPTX2 monomers.

2. The kit of claim 1, further comprising instructions on using the kit to detect NPTX2 by testing a biological sample obtained from a patient suspected of having, having or at risk of having cognitive dysfunction.

3. The kit of claim 1, further comprising a substrate.

4. The kit of claim 1, further comprising a positive control.

5. The kit of claim 4, wherein the positive control comprises a standard protein comprising the amino acid sequence of SEQ ID NO: 11.

6. The kit of claim 1, further comprising a detection reagent.

7. The kit of claim 1, further comprising a secondary antibody.

8. The kit of claim 7, wherein the secondary antibody is conjugated to a detection agent.

9. The kit of claim 1, wherein the antibody comprises an antibody produced by the hybridoma deposited under ATCC Accession No. PTA-122270.

10. The kit of claim 1, wherein the antibody comprises an antibody produced by the hybridoma deposited under ATCC Accession No. PT A-122271.

11. The kit of claim 1, comprising an antibody that specifically binds an epitope of NPTX2, wherein the epitope is set forth in SEQ ID NO: 17.

12. The kit of claim 1, further comprising an antibody that binds to NPTX1 and the NPTX1 antibody has a heavy chain comprising SEQ ID NO: 26 and a light chain comprising SEQ ID NO: 27.

13. The kit of claim 12 comprising an antibody that specifically binds to an epitope comprising SEQ ID NO: 18 of NPTX1.

14. The kit of claim 12, wherein the NPTX1 antibody comprises an antibody produced by the hybridoma deposited under ATCC Accession No. PT A-122269.

15. The kit of claim 1, wherein the agent of step (b) comprises dithiothreitol (DTT).

16. The kit of claim 1, wherein the agent of step (c) comprises N-ethylmaleimide (NEM).

17. A method for assessing cognitive dysfunction in a patient comprising the steps of:

(a) reducing heterocomplexes comprising NPTX1 and NPTX2 present in a biological sample obtained from the patient into NPTX1 and NPTX2 monomers;

(b) covalently modifying the thiol groups of the NPTX1 and NPTX2 monomers;

(c) detecting NPTX2 in the sample; and (d) assessing cognitive function in the patient by comparing NPTX2 detected in the sample to a control wherein the NPTX2 is detected by the NPTX2 antibody that has a heavy chain comprising SEQ ID NO: 28 and a light chain comprising SEQ ID NO: 29, or a heavy chain comprising SEQ ID NO: 30 and a light chain comprising SEQ ID NO: 31.

18. The method of claim 17, wherein detection step (c) further comprises detecting NPTX1 in the sample and assessment step (d) further comprises assessing cognitive function in the patient by comparing NPTX1 and NPTX2 detected in the sample to a control.

19. The method of claim 17, wherein reducing step (a) comprises incubating the biological sample with DTT.

20. The method of claim 17, wherein covalent modification step (b) comprises incubating the biological sample with NEM.

21. The method of claim 17, wherein detection step (c) comprises an enzyme linked immunosorbent assay (ELISA).

22. The method of claim 17, wherein the biological sample is a cerebrospinal fluid (CSF), blood or plasma sample.

23. The method of claim 21, wherein the ELISA comprises using the anti-NPTX2 monoclonal antibody produced by the hybridoma deposited under ATCC Accession No. PT A-122270.

24. The method of claim 21, wherein the ELISA comprises using the anti-NPTX2 monoclonal antibody produced by the hybridoma deposited under ATCC Accession No. PT A-122271.

25. The method of claim 21, wherein the ELISA comprises using the anti-NPTX1 monoclonal antibody produced by the hybridoma deposited under ATCC Accession No. PT A-122269.

26. The method of claim 21, wherein the ELISA comprises using a standard protein having the amino acid sequence shown in SEQ ID NO: 11.

27. The method of claim 21, wherein the ELISA comprises using an antibody that recognizes an epitope of NPTX2, wherein the epitope comprises SEQ ID NO: 17.

28. The method of claim 21, wherein the ELISA comprises using an antibody that binds to NPTX1 and the NPTX1 antibody has a heavy chain comprising SEQ ID NO: 26 and a light chain comprising SEQ ID NO: 27.

29. The method of claim 28, wherein the ELISA comprises using an antibody that recognizes an epitope of NPTX1, wherein the epitope comprises SEQ ID NO: 18.

* * * * *